US012758542B2

(12) United States Patent
Alahmari et al.

(10) Patent No.: US 12,758,542 B2
(45) Date of Patent: Oct. 13, 2026

(54) METHODS FOR TREATING PANCREATIC DUCTAL ADENOCARCINOMA

(71) Applicant: HEALTH RESEARCH, INC., Buffalo, NY (US)

(72) Inventors: Abdulrahman A. Alahmari, Buffalo, NY (US); Michael Feigin, Buffalo, NY (US)

(73) Assignee: HEALTH RESEARCH, INC., Buffalo, NY (US)

( * ) Notice: Subject to any disclaimer, the term of this patent is extended or adjusted under 35 U.S.C. 154(b) by 265 days.

(21) Appl. No.: 18/314,015

(22) Filed: May 8, 2023

(65) Prior Publication Data

US 2023/0355613 A1 Nov. 9, 2023

Related U.S. Application Data

(60) Provisional application No. 63/338,997, filed on May 6, 2022.

(51) Int. Cl.
*A61K 31/495* (2006.01)
*A61K 45/06* (2006.01)

(52) U.S. Cl.
CPC ............ *A61K 31/495* (2013.01); *A61K 45/06* (2013.01)

(58) Field of Classification Search
CPC ................................ A61K 31/45; A61K 45/06
See application file for complete search history.

(56) References Cited

PUBLICATIONS

Seebacher et al. Clinical development of targeted and immune based anti-cancer therapies, Journal of Experimental & Clinical Cancer Research (2019) 38:156 (Year: 2019).*
Burkhart, et. al. Curaxin CBL0137 eradicates drug resistant cancer stem cells and potentiates efficacy of gemcitabine in preclinical models of pancreatic cancer, Oncotarget, vol. 5, No. 22, Nov. 6, 2014 (Year: 2014).*
Berge, et. al., Pharmaceutical Salts, Journal of Pharmaceutical Sciences, Jan. 1977, vol. 66, No. 1. (Year: 1977).*
Bennouna, et. al. Afatinib-based combination regimens for the treatment of solid tumors: rationale, emerging strategies and recent progress, (Future Oncology, 12:3, 355-372) (Year: 2016).*
Erb, Phenotypic screening is an engine of discovery for bioactive small molecules and can unravel novel mechanisms and pathways controlling cellular physiology . . . ,Nature Chemical Biology, vol. 16, Jan. 2020 (Year: 2020).*
Liu, et.al., Synergy between vinorelbine and afatinib in the inhibition of non-small cell lung cancer progression by EGFR and p53 signaling pathways (Biomedicine & Pharmacotherapy 134 (2021) 111144) (Year: 2021).*
Remington: The Science and Practice of Pharmacy (2012) 22nd Edition, Philadelphia, PA. Lippincott Williams & Wilkins (Year: 2012).*
Bayat, Combination therapy in combating cancer, Oncotarget, 2017, vol. 8, (No. 23), pp. 38022-38043 (Year: 2017).*
Luo et al. Journal of Experimental & Clinical Cancer Research (2019) 38:249 (Year: 2019).*

* cited by examiner

*Primary Examiner* — Jeffrey S Lundgren
*Assistant Examiner* — Paul Randall Gauger
(74) *Attorney, Agent, or Firm* — Hodgson Russ LLP

(57) ABSTRACT

Provided are methods for treating individuals suspected of having or having Cleavage and Polyadenylation Specificity Factor 3 (CPSF3) associated cancer via administration of a CPSF3 inhibitor. Such cancers include pancreatic ductal adenocarcinoma (PDAC). The CPSF3 inhibitor may further attenuate PDAC cell proliferation and colony formation. The CPSF3 inhibitor may be JTE-607, which has the following structure:

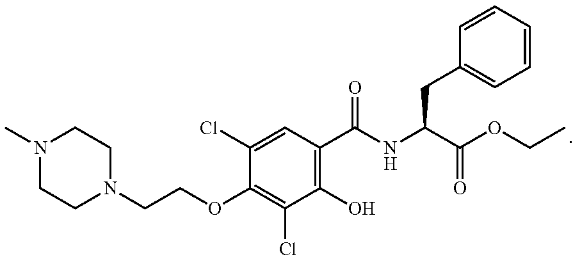

3 Claims, 50 Drawing Sheets

Specification includes a Sequence Listing.

E

Unique 3'UTR shortening genes

F

Unique 3'UTR lengthening genes

A

B

F

G

H

A

| Cell line | IC50 (μM) | Doubling time (h) |
|---|---|---|
| HPNE | 130.4 | 48.41 |
| HPDE | 60.11 | 59.31 |
| Suit2 | 23.33 | 19.765 |
| MiaPaCa2 | 6.96 | 15.345 |
| Panc1 | 2.163 | 29.475 |

B

E

F

E

F

C

A

| Term | P-value | FDR | Odds ratio | Combined Score | Genes |
|---|---|---|---|---|---|
| Chromatin assembly (GO:0031497) | 7.36E-06 | 0.006693444 | 11.07631874 | 130.922877 | H1-5; H2BC13; H2BC14; H2BC5; H2BC10; H2BC11; H3C1 |
| Nucleosome assembly (GO:0006334) | 2.17E-05 | 0.00884124 | 11.9951417 | 128.7851932 | H2BC13; H2BC14; H2BC5; H2BC10; H2BC11; H3C1 |
| Mitochondrial cytochrome c oxidase assembly (GO:0033617) | 3.83E-05 | 0.00884124 | 25.765625 | 262.0222728 | SURF1; SCO2; BCS1L; COX20 |
| Nucleosome organization (GO:0034728) | 3.89E-05 | 0.00884124 | 8.393784589 | 85.24289775 | H1-5; H2BC13; H2BC14; H2BC5; H2BC10; H2BC11; H3C1 |
| Establishment of protein localization to chromatin (GO:0071168) | 5.01E-05 | 0.009110558 | 61.55129534 | 609.5011178 | H1-5; RUVBL2; LRWD1 |

Figure 14

| | Gefitinib | Lapatinib | Osimertinib | Lazertinib | Afatinib | BLU-945 | LN6222 | LN6223 | JTE-607 |
|---|---|---|---|---|---|---|---|---|---|
| [Inhibitor] vs. normalized response -- Variable slope | | | | | | | | | |
| Best-fit values | | | | | | | | | |
| IC50 | 8.666 | 7.676 | 1.942 | 2.627 | 1.138 | 3.713 | 18.65 | 198.9 | 20.09 |
| HillSlope | -2.970 | -3.366 | -3.345 | -2.529 | -1.822 | -3.109 | -0.5481 | -1.396 | -0.5384 |
| logIC50 | 0.9378 | 0.8852 | 0.2882 | 0.4195 | 0.05615 | 0.5697 | 1.271 | 2.299 | 1.303 |

| | Gefitinib | Lapatinib | Osimertinib | Lazertinib | Afatinib | BLU-945 | LN6222 | LN6223 | JTE-607 |
|---|---|---|---|---|---|---|---|---|---|
| [Inhibitor] vs. normalized response -- Variable slope [2] | | | | | | | | | |
| Best-fit values | | | | | | | | | |
| IC50 | 20.84 | 11.37 | 3.286 | 3.066 | 1.543 | 4.843 | 115.2 | 65.29 | 43.97 |
| HillSlope | Unstable | -2.131 | -2.421 | -1.967 | -2.162 | -2.895 | -0.8974 | -6.019 | -0.6009 |
| logIC50 | 1.319 | 1.056 | 0.5167 | 0.4866 | 0.1883 | 0.6851 | 2.062 | 1.815 | 1.643 |

MiaPaCa2
Afatinib + JTE-607 Synergy

| Drug combination | Synergy score | Most synergistic area score | Method |
|---|---|---|---|
| JTE-607 - Afatinib | 5.88 | 10.57 | ZIP |

MiaPaCa2
Osimertinib + JTE-607 Synergy

| Drug combination | Synergy score | Most synergistic area score | Method |
|---|---|---|---|
| JTE-607 - Osimertinib | 4.00 | 5.89 | ZIP |

PANC-1
Afatinib + JTE-607 Synergy

| Drug combination | Synergy score | Most synergistic area score | Method |
|---|---|---|---|
| JTE-607 - Afatinib | 2.10 | 6.42 | ZIP |

PANC-1
Osimertinib + JTE-607 Synergy

| Drug combination | Synergy score | Most synergistic area score | Method |
|---|---|---|---|
| JTE-607 - Osimertinib | 1.65 | 4.10 | ZIP |

METHODS FOR TREATING PANCREATIC DUCTAL ADENOCARCINOMA

CROSS REFERENCE TO RELATED APPLICATION

This application claims priority to U.S. Provisional Patent Application No. 63/338,997, filed May 6, 2022, the disclosure of which is incorporated herein by reference.

STATEMENT REGARDING FEDERALLY SPONSORED RESEARCH

This invention was made with government support under contract no. CA016056 and CA181003 awarded by the National Institutes of Health. The government has certain rights in the invention.

SEQUENCE LISTING

The instant application contains a Sequence Listing, which is submitted in .xml format is hereby incorporated by reference in its entirety. Said .xml file is named "003551_01085_ST26.xml", was created on May 7, 2023, and is 22,205 bytes in size.

Large Tables

The instant application contains Tables S1, S2, and S3, all of which are submitted in .txt format and whose combined length would exceed 100 pages. All of these tables are hereby incorporated by reference in their entirety. Said .txt files are: "Table_S1.txt", created on May 7, 2023, and 2,151,341 bytes in size; "Table_S2.txt", created on May 7, 2023, and 745,431 bytes in size; and "Table_S3.txt", created on May 7, 2023, and 20,476 bytes in size.

One such gene regulatory process that has been implicated in cancer is processing of mRNAs, a step that is crucial for maturity of newly transcribed RNAs. For most human genes, nascent RNAs are cleaved and polyadenylated by a process called alternative polyadenylation, or APA. APA is a co-transcriptional mRNA processing mechanism that generates distinct transcript isoforms with different 3' untranslated region (UTR) lengths, ultimately affecting mRNA stability, localization and translation. This process is widely dysregulated in cancer. Recently, we identified widespread APA alterations in PDAC patients that are associated with functional changes in both gene and protein expression of growth-promoting genes. Interestingly, unlike polyadenylated genes, a class of histone genes are processed on the mRNA level by cleavage but not polyadenylation. These histones are replication-dependent and are crucial for cell proliferation. While APA and histone mRNA processing are regulated by two different complexes, some genes are in fact important regulators of both processes. One such gene is Cleavage and Polyadenylation Specificity Factor 3 (CPSF3), the endonuclease responsible for the cleavage of mRNAs. As a part of the APA complex, CPSF3 cooperates with other APA factors to cleave the mRNA prior to the addition of the poly(A) tail. As part of the histone cleavage complex (HCC), however, CPSF3 cleaves pre-mRNAs of replication-dependent core histones, but they do not get polyadenylated. Both APA and histone mRNA processing are important biological processes for cell proliferation and survival. The fact that CPSF3 is an enzyme opens the possibility of its pharmacological targeting.

LENGTHY TABLES

The patent contains a lengthy table section. A copy of the table is available in electronic form from the USPTO web site (https://seqdata.uspto.gov/docdetail?docId=US12758542B2). An electronic copy of the table will also be available from the USPTO upon request and payment of the fee set forth in 37 CFR 1.19(b)(3).

BACKGROUND OF THE DISCLOSURE

Pancreatic ductal adenocarcinoma (PDAC) is the third leading cause of cancer deaths with a five-year survival rate of 11%, due in part to the lack of effective treatment options. PDAC is primarily driven by mutations in the oncogene KRAS and several tumor suppressors, including TP53, CDKN2A and SMAD4. However, as clinically effective modulators of activity of these proteins are not currently available, identification of novel targets amenable to small molecule inhibition is a critical undertaking. Recently, large-scale RNA sequencing efforts of PDAC tumors have revealed widespread dysregulation of oncogenic gene expression, allowing the characterization of several PDAC subtypes and phenotypic states. These gene expression changes are critical for driving tumor phenotypes, including metastatic progression. While these gene expression changes have been extensively catalogued, the mechanisms underlying this transcriptional heterogeneity remain largely unknown.

SUMMARY OF THE DISCLOSURE

The present disclosure provides methods of treating individuals having or suspected of having cancers associated with Cleavage and Polyadenylation Specificity Factor 3 (CPSF3) or treating cancers via administering one or more agents capable of disrupting alternative polyadenylation. Also provided are compositions suitable for the methods of the present disclosure.

In an aspect, the present disclosure provides a method of treating an individual having or suspected of having a cancer associated with CPSF3. Further, the methods of the present disclosure may be used to inhibit cell growth of malignant cells and/or hyperplastic cells.

In aspect, the present disclosure provides compositions. The compositions comprise JTE-607:

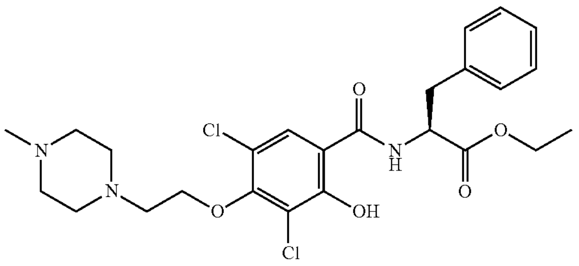 [SMILES: CCOC(=O)[C@H](Cc1ccccc1)NC(=O)c1cc(Cl)c(OCCN2CCN(C)CC2)c(Cl)c1O]

(or a pharmaceutically acceptable salt thereof, such as, for example, an HCl salt) and one or more cell checkpoint inhibitors, one or more chromatin modifying drugs, one or more chemotherapy drugs, or combinations thereof. In various embodiments, each of the one or more cell checkpoint inhibitors, one or more chromatin modifying drugs, one or more chemotherapy drugs may be administered at a therapeutically effective amount or at a concentration that would be typically considered a therapeutically effective amount when administered in the absence of JTE-607.

BRIEF DESCRIPTION OF THE FIGURES

For a fuller understanding of the nature and objects of the disclosure, reference should be made to the following detailed description taken in conjunction with the accompanying figures.

DETAILED DESCRIPTION OF THE DISCLOSURE

Figure 1:
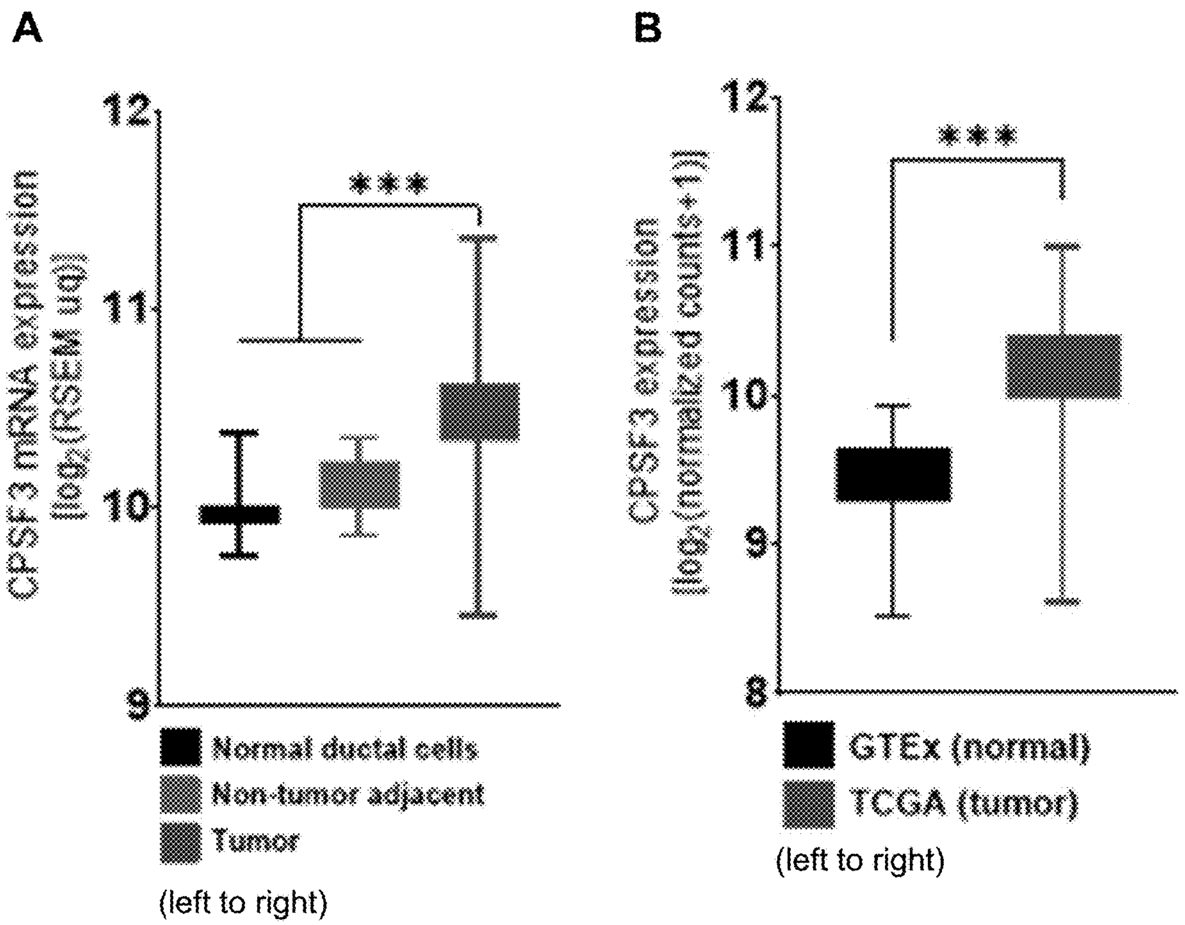
FIG. 1 shows CPSF3 is highly expressed in PDAC and is required for PDAC cell proliferation. (A) CPSF3 expression from CPTAC PDAC patient data. Whiskers indicate minimum and maximum data points. *, P<0.0001, Ordinary one-way ANOVA with Tukey multiple comparisons test. (B) CPSF3 expression from PDAC patient data (TCGA) as compared to normal pancreas (GTEx). Whiskers indicate minimum and maximum data points. *, P<0.0001, unpaired t test with Welch's correction. (C) Kaplan Meier survival curves of PDAC patients with high and low CPSF3 mRNA levels. Data were obtained from CPTAC database. (D) Immunoblot of CPSF3 in non-transformed pancreatic epithelial cells and PDAC cells. (E) Immunoblot of CPSF3 in shNTC, sh1 and sh2 CPSF3 knockdown cells. (F) Proliferation rates at days 0, 2, 4 and 6 of shNTC, sh1 and sh2 CPSF3 knockdown cells. , P<0.01; *, P<0.001; 2way ANOVA with Dunnett's multiple comparisons test. (G) Clonogenic growth assay of shNTC, sh1 and sh2 CPSF3 knockdown cells. (H) Volume of CPSF3-knockdown and control MiaPaCa2 tumors. ***, P<0.001, 2way ANOVA. (I) Gross images of shNTC (n=7) and shCPSF3 (n=6) dissected tumors. (J) Endpoint tumor weight. *, P<0.05, unpaired t test with Welch's correction. (K, L) IHC for CPSF3 and Ki67, respectively. Box and whisker plots indicate the percentage of CPSF3- and Ki67-positive areas in the tumors. , P<0.01; *, P<0.001; unpaired t test.
Figure 1:
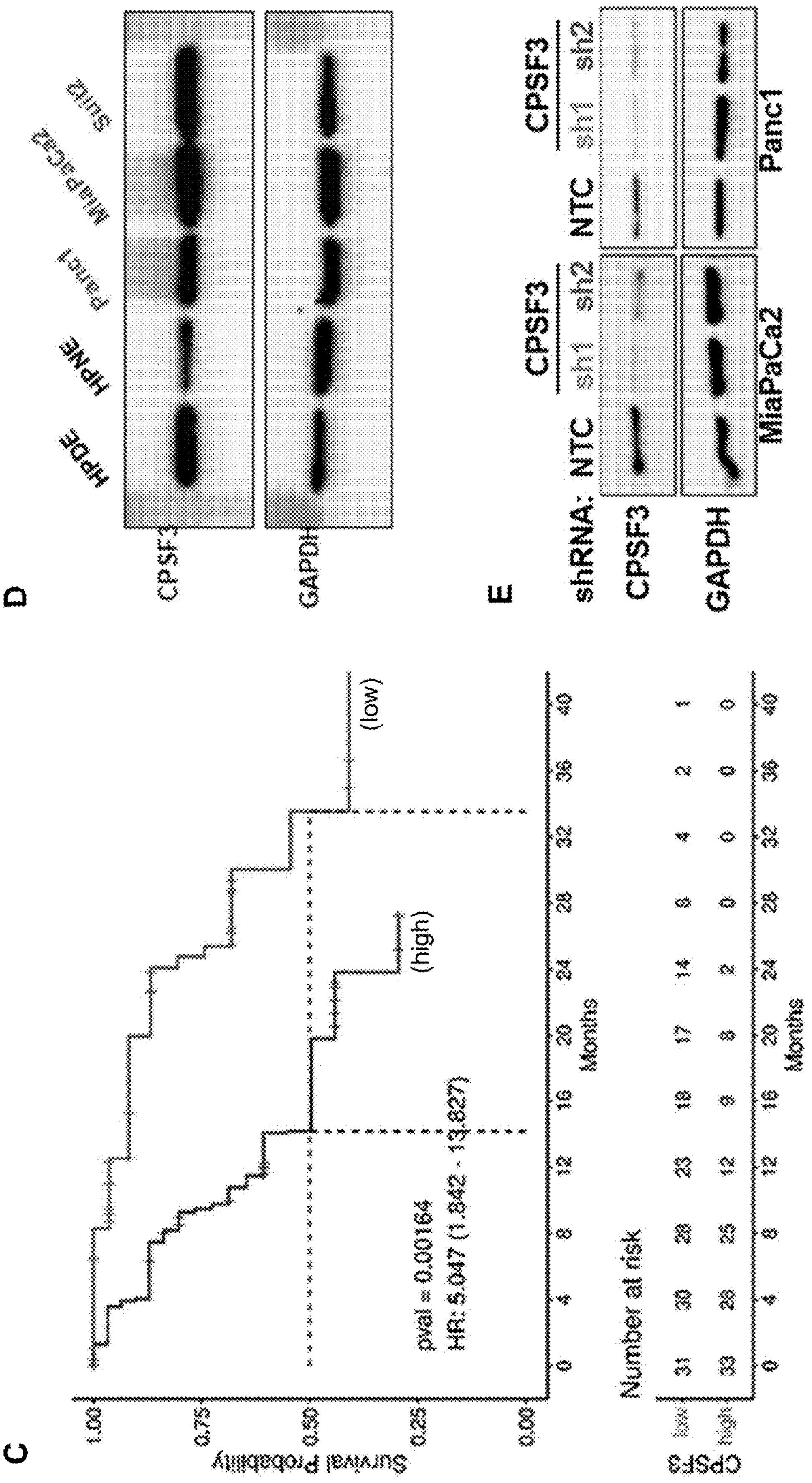
Figure 1:
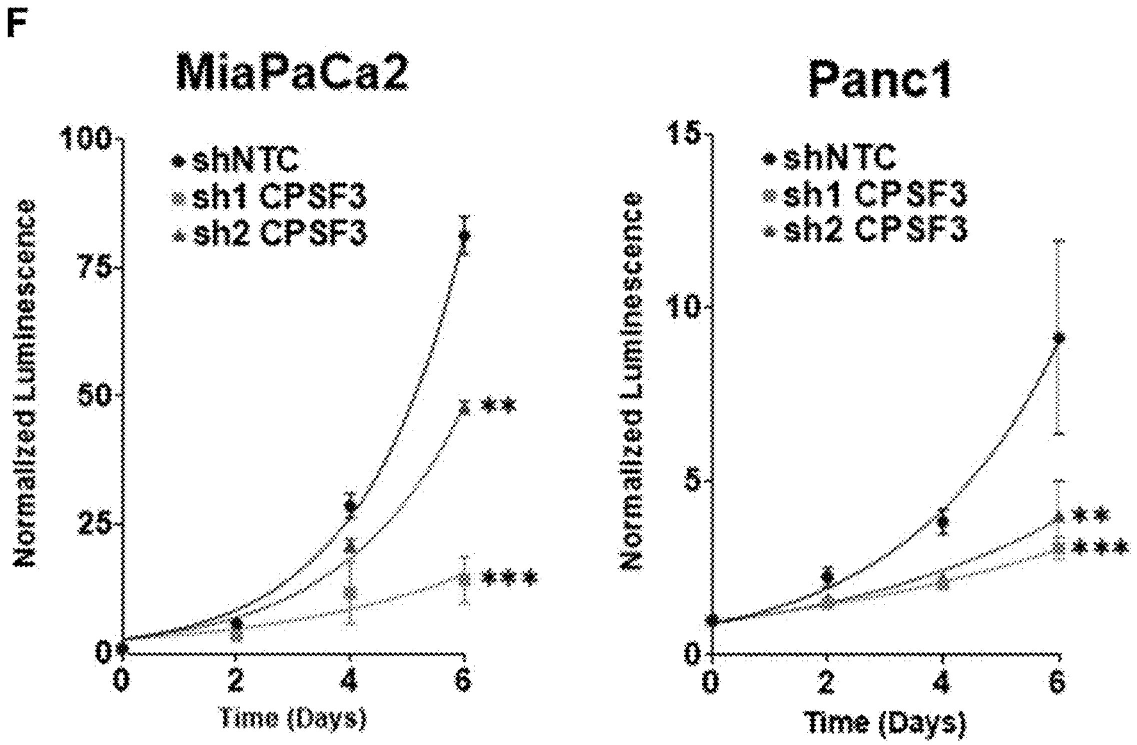
Figure 1:
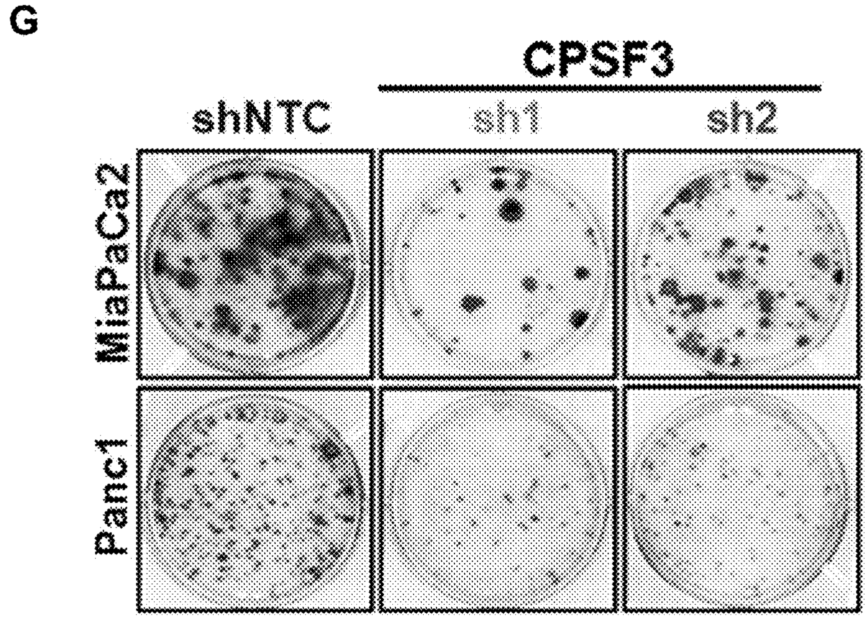
Figure 1:
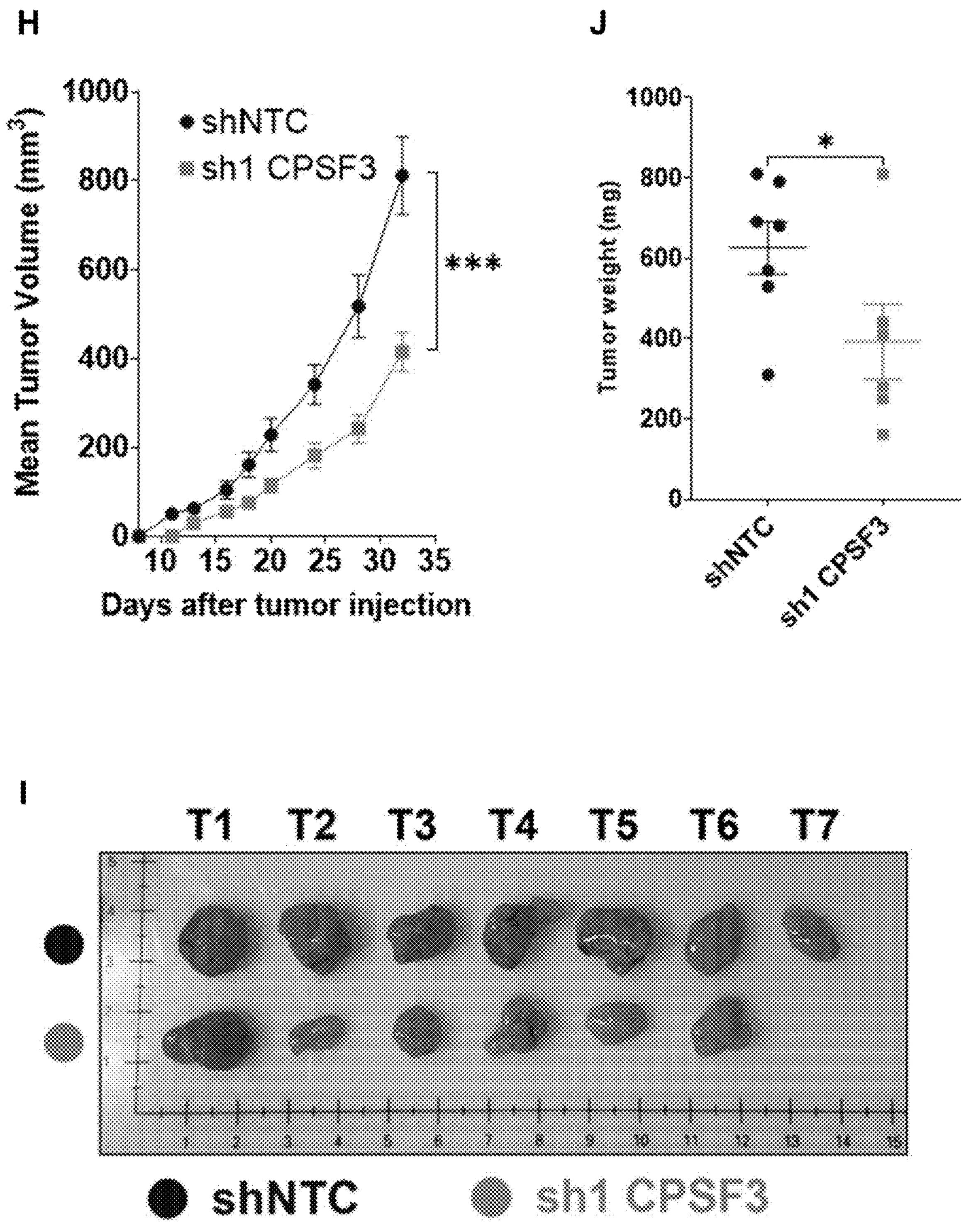
Figure 1:
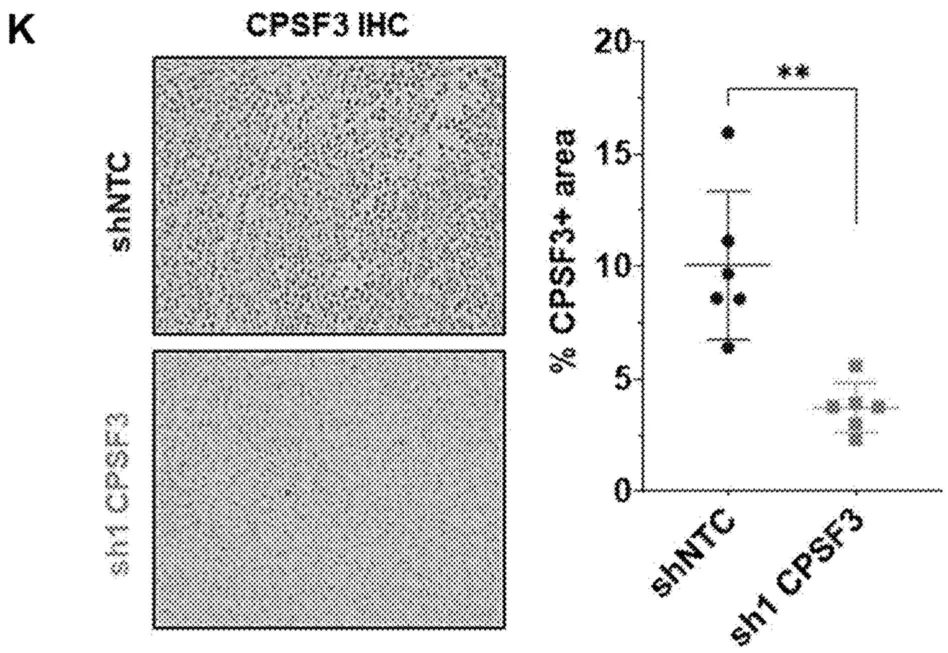
Figure 1:
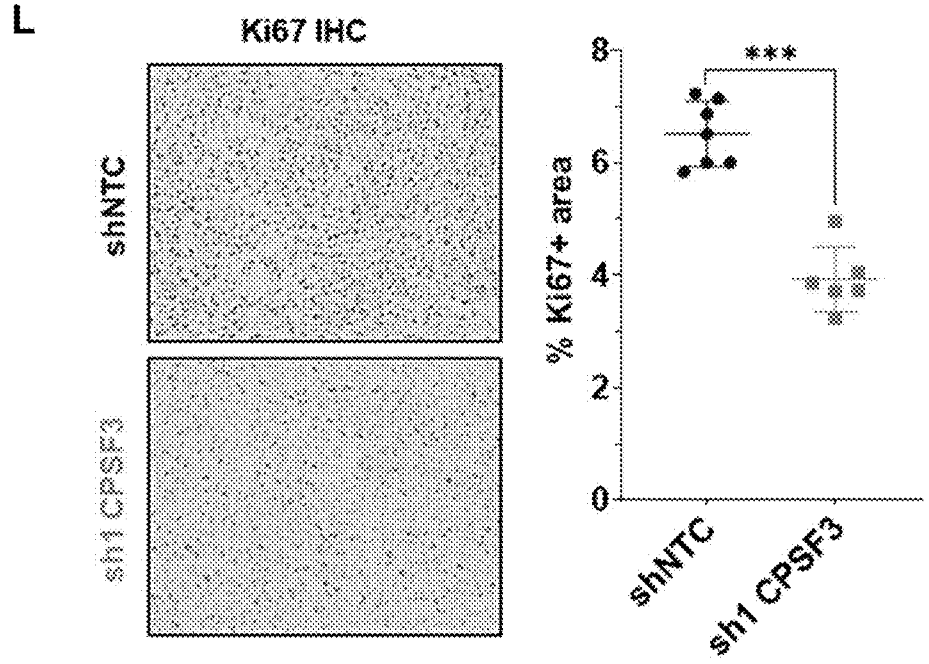

Although claimed subject matter will be described in terms of certain embodiments, other embodiments, including embodiments that do not provide all of the benefits and features set forth herein, are also within the scope of this disclosure. Various structural, logical, and process step changes may be made without departing from the scope of the disclosure.

All ranges provided herein include all values that fall within the ranges to the tenth decimal place, unless indicated otherwise.

Whenever a singular term is used in this disclosure, a plural term is also included. For example, “a”, or “an” also includes a plurality of the referenced items, unless otherwise indicated.

The term “therapeutically effective amount” as used herein refers to an amount of an agent sufficient to achieve, in a single or multiple doses, the intended purpose of treatment. Treatment does not have to lead to complete cure, although it may. Treatment can mean alleviation of one or more of the symptoms or markers of the indication. The exact amount desired or required will vary depending on the composition used, its mode of administration, patient specifics and the like. Appropriate effective amount can be determined by one of ordinary skill in the art informed by the instant disclosure using only routine experimentation. Treatment can be orientated symptomatically, for example, to suppress symptoms. It can be effected over a short period, over a medium term, or can be a long-term treatment, such as, for example within the context of a maintenance therapy. Treatment can be continuous or intermittent.

The present disclosure provides methods of treating individuals having or suspected of having cancers associated with Cleavage and Polyadenylation Specificity Factor 3 (CPSF3) or treating cancers via administering one or more agents capable of disrupting alternative polyadenylation. Also provided are compositions suitable for the methods of the present disclosure.

CPSF3 is a target of the small molecule JTE-607. JTE-607 is hydrolyzed into an active compound that directly interacts with the CPSF3 interfacial cavity. This interaction inhibits CPSF3 catalytic activity leading to accumulation of unprocessed newly synthesized pre-mRNAs. JTE-607 induces apoptosis of human acute myeloid leukemia (AML) and Ewing's sarcoma cells in vitro and prolongs survival of tumor-bearing mice in xenograft models in vivo. Also, JTE-607 inhibits migration, invasion and self-renewal of breast cancer cells. Notably, administration of JTE-607 in healthy volunteers demonstrated the safety of this compound in humans, with no severe adverse events reported. However, the role of CPSF3 and the effect of JTE-607 in epithelial cancers remains unknown.

In an aspect, the present disclosure provides a method of treating an individual having or suspected of having a cancer associated with CPSF3. Further, the methods of the present disclosure may be used to inhibit cell growth of malignant cells and/or hyperplastic cells.

A method of the present disclosure may be used to treat various types of cancers associated with CPSF3, such as, for example, adenocarcinomas. Non-limiting examples of adenocarcinomas include esophageal cancers, pancreatic cancers, prostate cancers, cervical cancers, stomach cancers, colorectal cancers, breast cancers, lung cancers, bile duct cancers, and the like. In various examples, the cancer is pancreatic ductal adenocarcinoma.

Without intending to be bound by any particular theory, it is considered that administration of a CPSF3 inhibitor (e.g., JTE-607), which attenuates cell proliferation of certain malignant cells (e.g., PDAC cells) and further inhibits expression of replication-dependent histones.

In various examples, one or more compounds and/or one or more compositions comprising one or more compounds described herein are be administered to a subject in need of treatment using any known method and route, including oral, parenteral, subcutaneous, intraperitoneal, intrapulmonary, intranasal and intracranial injections. Parenteral infusions include intramuscular, intravenous, intraarterial, intraperitoneal, and subcutaneous administration. Topical and/or transdermal administrations are also encompassed.

Various CPSF3 inhibitors may be used. In various embodiments, the CPSF3 inhibitor is JTE-607, which has the following structure:

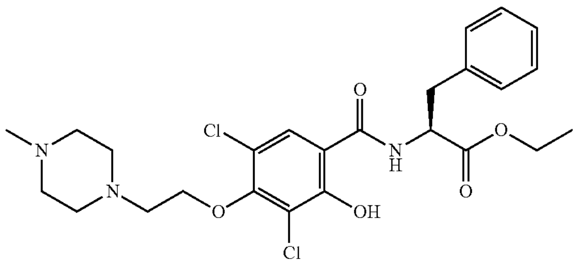 [SMILES: CCOC(=O)[C@H](Cc1ccccc1)NC(=O)c1cc(Cl)c(OCCN2CCN(C)CC2)c(Cl)c1O]

(or a pharmaceutically acceptable salt, such as, for example, an HCl salt). The composition may further comprise one or more cell checkpoint inhibitors, one or more chromatin modifying drugs, one or more chemotherapy drugs, or combinations thereof. Examples of cell checkpoint inhibitors, chromatin modifying drugs, and chemotherapy drugs are provided herein.

Methods of the present disclosure may be used on various individuals. In various examples, an individual is a human or non-human mammal. Examples of non-human mammals include, but are not limited to, farm animals, such as, for example, cows, hogs, sheep, and the like, as well as pet or sport animals such as, for example, horses, dogs, cats, and the like. Additional non-limiting examples of individuals include, but are not limited to, rabbits, rats, mice, and the like.

In aspect, the present disclosure provides compositions. The compositions comprise JTE-607:

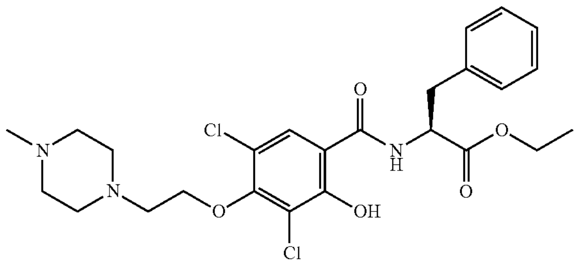 [SMILES: CCOC(=O)[C@H](Cc1ccccc1)NC(=O)c1cc(Cl)c(OCCN2CCN(C)CC2)c(Cl)c1O]

(or a pharmaceutically acceptable salt thereof, such as, for example, an HCl salt) and one or more cell cycle checkpoint inhibitors, one or more chromatin modifying drugs, one or more chemotherapy drugs, one or more EGFR inhibitors, or combinations thereof. In various embodiments, each of the one or more cell cycle checkpoint inhibitors, one or more chromatin modifying drugs, one or more chemotherapy drugs, and/or one or more EGFR inhibitors may be administered at a therapeutically effective amount or at a concentration that would be typically considered a therapeutically effective amount when administered in the absence of JTE-607.

Various cell cycle checkpoint inhibitors may be used. Examples of cell cycle checkpoint inhibitors include, but are not limited to, abemaciclib, palbociclib, and ribociclib, and the like, and combinations thereof.

Various chromatin modifying drugs may be used. Examples of chromatin modifying drugs include, but are not limited to, HDAC inhibitors, HAT inhibitors, HMT inhibitors, and HDM inhibitors. Examples of HDAC inhibitors include, but are not limited to, trichostatin A, panobinostat, belinostat, suberoylanilide hydroxamic acid, valproic acid, sodium butyrate, and the like, and combinations thereof. HAT inhibitors include, but are not limited, to garcinol, curcumin, C646, and the like, and combinations thereof. HMT inhibitors include, but are not limited to, GSK126 (GSK2816126), BIX01294 (diazepin-quinazolin-amine derivative), EPZ004777, EPZ5676, and the like, and combinations thereof. HDM inhibitors include, but are not limited to, GSK-J4 and the like, and combinations thereof. Additional examples of chromatin modifying drugs include, but are not limited to, CBL0137 (which has the following structure:

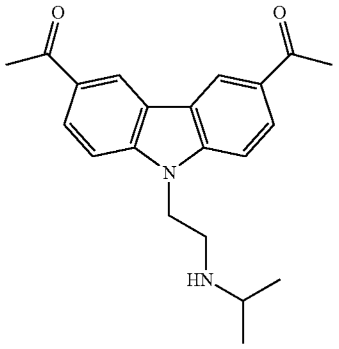 [SMILES: CC(=O)c1ccc2c(c1)c1cc(C(C)=O)ccc1n2CCNC(C)C]

and pharmaceutically acceptable salts thereof (e.g., a CLB0137 HCl salt).

Various chemotherapy agents (e.g., chemotherapy drugs) can be used. Any FDA approved chemotherapy agents (e.g., chemotherapy drugs) can be used. Combinations of chemotherapy agents can be used. Non-limiting examples of chemotherapy agents and combinations include abemaciclib, abiraterone acetate, ABITREXATE® (methotrexate), ABVD (doxorubicin, bleomycin, vinblastine, and dacarbazine), ABVE (doxorubicin, bleomycin, vincristine sulfate, etoposide phosphate), ABVE-PC (doxorubicin, bleomycin, vincristine sulfate, etoposide phosphate, prednisone, cyclophosphamide), AC (doxorubicin and cyclophosphamide), acalabrutinib, AC-T (doxorubicin, cyclophosphamide, paclitaxel), ADE (cytarabine, daunorubicin, etoposide), ADRIAMYCIN® (doxorubicin hydrochloride), afatinib dimaleate, AFINITOR® (everolimus), AKYNZEO® (netupitant and palonosetron hydrochloride), ALDARA® (imiquimod), aldesleukin, ALECENSA® (alectinib), alectinib, ALIMTA® (pemetrexed disodium), ALIQOPA® (copanlisib hydrochloride), ALKERAN® for injection (melphalan hydrochloride), ALKERAN® tablets (melphalan), ALOXI® (palonosetron hydrochloride), ALUNBRIG™ (brigatinib), ambochlorin (chlorambucil), amboclorin (chlorambucil), amifostine, aminolevulinic acid, anastrozole, aprepitant, AREDIA® (pamidronate disodium), ARIMIDEX® (anastrozole), AROMASIN® (exemestane), ARRANON® (nelarabine), arsenic trioxide, asparaginase *Erwinia chrysanthemi*, axicabtagene ciloleucel, axitinib, azacitidine, BEACOPP (bleomycin, etoposide, doxorubicin, cyclophosphamide, vincristine, procarbazine, prednisone), Becenum® (carmustine), Beleodaq® (belinostat), belinostat, bendamustine hydrochloride, BEP (bleomycin, etoposide, cisplatin), bexarotene, bicalutamide, BICNU® (carmustine), bleomycin, bortezomib, Bosulif® (bosutinib), bosutinib, brigatinib, BuMel (busulfan, melphalan hydrochloride), busulfan, BUSULFEX® (busulfan), cabazitaxel, CABOMETYX™ (cabozantinib-S-malate), cabozantinib-S-malate, CAF (cyclophosphamide, doxorubicin, 5-fluorouracil), CALQUENCE® (acalabrutinib), CAMPTOSAR® (irinotecan hydrochloride), capecitabine, CAPDX, CARAC™ (fluorouracil—topical), carboplatin, carboplatin-TAXOL®, carfilzomib, carmubris (carmustine), carmustine, carmustine implant, CASODEX® (bicalutamide), CEM (carboplatin, etoposide, melphalan), ceritinib, CERUBIDINE® (daunorubicin hydrochloride), CEV (carboplatin, etoposide phosphate, vincristine sulfate), chlorambucil, chlorambucil-prednisone, CHOP (cyclophosphamide, doxorubicin, vincristine, prednisone), cisplatin, cladribine, CLAFEN® (cyclophosphamide), clofarabine, CLOFAREX® (clofarabine), CLOLAR® (clofarabine), CMF (cyclophosphamide, methotrexate, fluorouracil), cobimetinib, COMETRIQ® (cabozantinib-S-malate), copanlisib hydrochloride, COPDAC (cyclophosphamide, vincristine sulfate, prednisone, dacarbazine), COPP (cyclophosphamide, vincristine, procarbazine, prednisone), COPP-ABV (cyclophosphamide, vincristine, procarbazine, prednisone, doxorubicin, bleomycin, vinblastine sulfate), COSMEGEN® (dactinomycin), COTELLIC® (cobimetinib), crizotinib, CVP (cyclophosphamide, vincristine, prednisolone), cyclophosphamide, CYFOS® (ifosfamide), cytarabine, cytarabine liposome, CYTOSAR-U® (cytarabine), CYTOXAN® (cyclophosphamide), dabrafenib, dacarbazine, DACOGEN® (decitabine), dactinomycin, dasatinib, daunorubicin hydrochloride, daunorubicin hydrochloride and cytarabine liposome, decitabine, defibrotide sodium, DEFITELIO® (defibrotide sodium), degarelix, denileukin diftitox, dexamethasone, dexrazoxane hydrochloride, docetaxel, doxorubicin, doxorubicin hydrochloride, doxorubicin hydrochloride liposome, DOX-SL® (doxorubicin hydrochloride liposome), DTIC-DOME® (dacarbazine), ELITEK® (rasburicase), ELLENCE® (epirubicin hydrochloride), ELOXATIN®

(oxaliplatin), eltrombopag olamine, EMEND® (aprepitant), enasidenib mesylate, enzalutamide, epirubicin hydrochloride, EPOCH (etoposide, prednisone, vincristine, cyclophosphamide, and doxorubicin hydrochloride), eribulin mesylate, ERIVEDGE® (vismodegib), erlotinib hydrochloride, ERWINAZE® (asparaginase *Erwinia chrysanthemi*), ETHYOL® (amifostine), ETOPOPHOS® (etoposide phosphate), etoposide, etoposide phosphate, everolimus, EVISTA® (raloxifene hydrochloride), EVOMELA® (melphalan hydrochloride), exemestane, 5-FU (fluorouracil), FARESTON® (toremifene), FARYDAK® (panobinostat), FASLODEX® (fulvestrant), FEC (5-fluorouracil, epirubicin, cyclophosphamide), FEMARA® (letrozole), filgrastim, FLUDARA® (fludarabine phosphate), fludarabine phosphate, flutamide, FOLEX® (methotrexate), FOLEX PFS® (methotrexate), FOLFIRI (leucovorin calcium, fluorouracil, irinotecan hydrochloride), FOLFIRINOX (leucovorin calcium, fluorouracil, irinotecan hydrochloride, oxaliplatin), FOLFOX (leucovorin calcium, fluorouracil, oxaliplatin), FOLOTYN® (pralatrexate), FU-LV (fluorouracil, leucovorin calcium), fulvestrant, gefitinib, gemcitabine hydrochloride, gemcitabine-cisplatin, gemcitabine-oxaliplatin, GEMZAR® (gemcitabine hydrochloride), GILOTRIF® (afatinib dimaleate), GLEEVEC® (imatinib mesylate), GLIADEL® (carmustine implant), goserelin acetate, HALAVEN® (eribulin mesylate), HEMANGEOL® (propranolol hydrochloride), Hycamtin® (topotecan hydrochloride), HYDREA® (hydroxyurea), hydroxyurea, Hyper-CVAD (course A: cyclophosphamide, vincristine, doxorubicin, dexamethasone, cytarabine, mesna, methotrexate; and course B: methotrexate, leucovorin, sodium bicarbonate, cytarabine), IBRANCE® (palbociclib), ibrutinib, ICE (ifosfamide, mesna, carboplatin, etoposide), ICLUSIG® (ponatinib hydrochloride), IDAMYCIN® (idarubicin hydrochloride), idarubicin hydrochloride, idelalisib, IDHIFA® (enasidenib mesylate), IFEX® (ifosfamide), ifosfamide, IFOSFAMIDUM™ (ifosfamide), imatinib mesylate, IMBRUVICA® (ibrutinib), imiquimod, IMLYGIC® (talimogene laherparepvec), INLYTA® (axitinib), IRESSA® (gefitinib), irinotecan, irinotecan hydrochloride, irinotecan hydrochloride liposome, ISTODAX® (romidepsin), ixabepilone, ixazomib citrate, IXEMPRA® (ixabepilone), JAKAFI® (ruxolitinib phosphate), JEB (carboplatin, etoposide phosphate, bleomycin), JEVTANA® (cabazitaxel), KEOXIFENE™ (raloxifene hydrochloride), KEPIVANCE® (palifermin), KISQALI® (ribociclib), KYMRIAH™ (tisagenlecleucel), KYPROLIS® (carfilzomib), lanreotide acetate, lapatinib ditosylate, lenalidomide, lenvatinib mesylate, LENVIMA® (lenvatinib mesylate), letrozole, leucovorin calcium, LEUKERAN® (chlorambucil), leuprolide acetate, LEUSTATIN® (cladribine), LEVULAN® (aminolevulinic acid), LINFOLIZIN™ (chlorambucil), lomustine, LONSURF® (trifluridine and tipiracil hydrochloride), LUPRON® (leuprolide acetate), LUPRON DEPOT® (leuprolide acetate), LUPRON DEPOT-PED® (leuprolide acetate), LYNPARZA® (olaparib), MATULANE® (procarbazine hydrochloride), mechlorethamine hydrochloride, megestrol acetate, MEKINIST® (trametinib), melphalan, melphalan hydrochloride, mercaptopurine, mesna, MESNEX® (Mesna), METHAZOLASTONE™ (temozolomide), methotrexate, METHOTREXATE LPF™ (methotrexate), methylnaltrexone bromide, MEXATE® (methotrexate), MEXATE-AQ™ (methotrexate), midostaurin, mitomycin C, mitoxantrone hydrochloride, MITOZYTREX™ (mitomycin C), MOPP (mustargen, vincristine, procarbazine, prednisone), MOZOBIL™ (plerixafor), MUSTARGEN® (mechlorethamine hydrochloride), MUTAMYCIN™ (mitomycin C), MYLERAN® (busulfan), MYLOSAR® (azacitidine), NAVELBINE® (vinorelbine tartrate), nelarabine, NEOSAR® (cyclophosphamide), neratinib maleate, NERLYNX® (neratinib maleate), netupitant and palonosetron hydrochloride, NEULASTA® (pegfilgrastim), NEUPOGEN® (filgrastim), NEXAVAR® (sorafenib tosylate), NILANDRON® (nilutamide), nilotinib, nilutamide, NINLARO® (ixazomib citrate), niraparib tosylate monohydrate, NOLVADEX® (tamoxifen citrate), NPLATE® (romiplostim), ODOMZO® (sonidegib), OEPA (vincristine sulfate, etoposide phosphate, prednisone, doxorubicin hydrochloride), OFF (oxaliplatin, fluorouracil, leucovorin), olaparib, omacetaxine mepesuccinate, ondansetron hydrochloride, ONTAK® (denileukin diftitox), OPPA (vincristine sulfate, procarbazine hydrochloride, prednisone, doxorubicin hydrochloride), osimertinib, oxaliplatin, paclitaxel, PAD (bortezomib, doxorubicin hydrochloride, dexamethasone), palbociclib, palifermin, palonosetron hydrochloride, pamidronate disodium, panobinostat, paraplat (carboplatin), PARAPLATIN® (carboplatin), pazopanib hydrochloride, PCV (procarbazine hydrochloride, lomustine, vincristine sulfate), PEB (cisplatin, etoposide phosphate, bleomycin), pegfilgrastim, pemetrexed disodium, PLATINOL® (cisplatin), PLATINOL®-AQ (cisplatin), plerixafor, pomalidomide, POMALYST® (pomalidomide), ponatinib hydrochloride, pralatrexate, prednisone, procarbazine hydrochloride, PROMACTA® (eltrombopag olamine), propranolol hydrochloride, PURINETHOL® (mercaptopurine), PURIXAN® (mercaptopurine), radium 223 dichloride, raloxifene hydrochloride, rasburicase, regorafenib, RELISTOR® (methylnaltrexone bromide), REVLIMID® (lenalidomide), RHEUMATREX® (methotrexate), ribociclib, rolapitant hydrochloride, romidepsin, romiplostim, rubidomycin (daunorubicin hydrochloride), RUBRACA® (rucaparib camsylate), rucaparib camsylate, ruxolitinib phosphate, RYDAPT® (midostaurin), SCLEROSOL® Intrapleural Aerosol (Talc), sipuleucel-T, SOMATULINE® Depot (lanreotide acetate), sonidegib, sorafenib tosylate, SPRYCEL® (dasatinib), Stanford V (mechlorethamine hydrochloride, doxorubicin hydrochloride, vinblastine sulfate, vincristine sulfate, bleomycin, etoposide phosphate, prednisone), sterile talc powder (Talc), STERITALC® (Talc), STIVARGA® (regorafenib), sunitinib malate, SUTENT® (sunitinib malate), SYNRIBO™ (omacetaxine mepesuccinate), TABLOID® (thioguanine), TAC (docetaxel, doxorubicin hydrochloride, cyclophosphamide), TAFINLAR® (dabrafenib), TAGRISSO® (osimertinib), Talc, tamoxifen citrate, TARABINE PFS® (cytarabine), TARCEVA® (erlotinib hydrochloride), TARGRETIN® (bexarotene), TASIGNA® (nilotinib), TAXOL® (Paclitaxel), TAXOTERE® (docetaxel), TEMODAR® (temozolomide), temozolomide, temsirolimus, thalidomide, THALOMID® (thalidomide), thioguanine, thiotepa, TOTECT® (dexrazoxane hydrochloride), TPF (docetaxel, cisplatin, fluorouracil), trabectedin, trametinib, TREANDA® (bendamustine hydrochloride), trifluridine and tipiracil hydrochloride, TRISENOX® (arsenic trioxide), TYKERB® (lapatinib ditosylate), uridine triacetate, VAC (vincristine sulfate, dactinomycin, cyclophosphamide), valrubicin, VALSTAR® (valrubicin), vandetanib, VAMP (vincristine sulfate, doxorubicin hydrochloride, methotrexate, prednisone), VARUBI® (rolapitant hydrochloride), VeIP (vinblastine sulfate, ifosfamide, cisplatin), VELBAN® (vinblastine sulfate), VELCADE® (bortezomib), VELSAR® (vinblastine sulfate), vemurafenib, VENCLEXTA™ (venetoclax), venetoclax, VERZENIO™ (abemaciclib), VIADUR® (leuprolide acetate), VIDAZA®

(azacitidine), vinblastine sulfate, VINCASAR PFS® (vincristine sulfate), vincristine sulfate, vinorelbine tartrate, VIP (etoposide phosphate, ifosfamide, cisplatin), vismodegib, VISTOGARD® (uridine triacetate), vorinostat, VOTRIENT® (pazopanib hydrochloride), WELLCOVORIN® (leucovorin calcium), XALKORI® (crizotinib), XELODA® (capecitabine), XELIRI (capecitabine, irinotecan hydrochloride), XELOX (capecitabine, oxaliplatin), XOFIGO® (radium 223 dichloride), XTANDI® (enzalutamide), YESCARTA™ (axicabtagene ciloleucel), YONDELIS® (trabectedin), ZALTRAP® (ziv-aflibercept), ZARXIO® (filgrastim), ZEJULA® (niraparib tosylate monohydrate), ZELBORAF® (vemurafenib), ZINECARD® (dexrazoxane hydrochloride), ZOFRAN® (ondansetron hydrochloride), ZOLADEX® (goserelin acetate), zoledronic acid, ZOLINZA® (vorinostat), ZOMETA® (zoledronic acid), ZYDELIG® (idelalisib), ZYKADIA® (ceritinib), and ZYTIGA® (abiraterone acetate).

Various EGFR inhibitors may be used. Examples of EGFR inhibitors include, but are not limited to, afatinib, osimertinib, and the like, and combinations thereof.

The compositions may include one or more pharmaceutically acceptable carrier(s). Non-limiting examples of compositions include solutions, suspensions, emulsions, solid injectable compositions that are dissolved or suspended in a solvent before use, and the like. Injections may be prepared by dissolving, suspending, or emulsifying one or more of the active ingredient(s) in a diluent. Non-limiting examples of diluents include distilled water (e.g., for injection), physiological saline, vegetable oil, alcohol, and the like, and combinations thereof. Injections may contain, for example, stabilizers, solubilizers, suspending agents, emulsifiers, soothing agents, buffers, preservatives, and the like, and combinations thereof. Injections may be sterilized in the final formulation step or prepared by sterile procedure. A pharmaceutical composition of the disclosure may also be formulated into a sterile solid preparation, for example, by freeze-drying, and may be used after sterilized or dissolved in sterile injectable water or other sterile diluent(s) immediately before use. Additional examples of pharmaceutically acceptable carriers include, but are not limited to, sugars, such as, for example, lactose, glucose, and sucrose; starches, such as, for example, corn starch and potato starch; cellulose, such as, for example, sodium carboxymethyl cellulose, ethyl cellulose, and cellulose acetate; powdered tragacanth; malt; gelatin; talc; excipients, such as, for example, cocoa butter and suppository waxes; oils, such as, for example, peanut oil, cottonseed oil, safflower oil, sesame oil, olive oil, corn oil, and soybean oil; glycols, such as, for example, propylene glycol; polyols, such as, for example, glycerin, sorbitol, mannitol, and polyethylene glycol; esters, such as, for example, ethyl oleate and ethyl laurate; agar; buffering agents, such as, for example, magnesium hydroxide and aluminum hydroxide; alginic acid; pyrogen-free water; isotonic saline; Ringer's solution; ethyl alcohol; phosphate buffer solutions; other non-toxic compatible substances employed in pharmaceutical formulations, and the like, and combinations thereof. Non-limiting examples of pharmaceutically acceptable carriers are found in: *Remington: The Science and Practice of Pharmacy* (2012) 22nd Edition, Philadelphia, PA. Lippincott Williams & Wilkins.

Compositions of the disclosure can comprise more than one pharmaceutical agent. For example, a first composition comprising a compound of the disclosure and a first pharmaceutical agent can be separately prepared from a composition which comprises the same compound of the disclosure and a second pharmaceutical agent, and such preparations can be mixed to provide a two-pronged (or more) approach to achieving the desired prophylaxis or therapy in an individual. Further, compositions of the disclosure can be prepared using mixed preparations of any of the compounds disclosed herein.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Compositions of the disclosure suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present disclosure as an active ingredient. A compound of the present disclosure may also be administered as a bolus, electuary or paste.

In solid dosage forms of the disclosure for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered active ingredient moistened with an inert liquid diluent.

The tablets, and other solid dosage forms of the pharmaceutical compositions of the present disclosure, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of a compound of the present disclosure include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

In addition to inert diluents, the oral compositions can include adjuvants such as wetting agents, emulsifying and suspending agents, sweetening, flavoring, coloring, perfuming and preservative agents.

Suspensions, in addition to a compound of the disclosure, the composition may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

The composition may be for administration to an individual in need of treatment.

In various examples, the composition may be suitable for injection. Parenteral administration includes infusions and injections, such as, for example, intramuscular, intravenous, intraarterial, intraperitoneal, subcutaneous administration, and the like.

The compositions may be administered systemically. The term "systemic" as used herein includes parenteral, topical, oral, spray inhalation, rectal, nasal, and buccal administration. The term "parenteral" as used herein includes subcutaneous, intravenous, intramuscular, intra-articular, intrasynovial, intrasternal, intrathecal, intrahepatic, intralesional, and intracranial administration. Compositions may be administered orally, may be administered parenterally, and/or intravenously. Compositions suitable for parenteral, administration may include aqueous and/or non-aqueous carriers and diluents, such as, for example, sterile injection solutions. Sterile injection solutions may contain anti-oxidants, buffers, bacteriostatic agents and solutes, which render the composition isotonic with the blood of the intended recipient. Aqueous and/or non-aqueous sterile suspensions may include suspending agents and thickening agents.

Nasal aerosol and inhalation compositions of the present disclosure may be prepared by any method in the art. Such compositions may include dosing vehicles, such as, for example, saline; preservatives, such as, for example, benzyl alcohol; absorption promoters to enhance bioavailability; fluorocarbons used in the delivery systems (e.g., nebulizers and the like; solubilizing agents; dispersing agents; or a combination thereof).

Compositions suitable for systemic administration are also disclosed. For example, an inhibitor as described herein may be used to prepare a stock solution (e.g., a 100 mM stock solution in DMSO). The stock solution may be further diluted with PBS to a concentration suitable for administration (e.g., 1-20 mM of inhibitor). Various solvents may be used to prepare the stock solution. Such solvents are described herein and are known in the art.

The steps of the method described in the various embodiments and examples disclosed herein are sufficient to carry out the methods of the present invention. Thus, in an embodiment, the method consists essentially of a combination of the steps of the methods disclosed herein. In another embodiment, the method consists of such steps.

The following Statements are intended to be limiting in any way.

Statement 1. A method for treating an individual suspected of having or having a Cleavage and Polyadenylation Specificity Factor 3 (CPSF3) associated cancer comprising administering to the individual a composition comprising a therapeutically effective amount of an CPSF3 inhibitor.

Statement 2. A method according to Statement 1, wherein the CPSF3-associated cancer is an adenocarcinoma.

Statement 3. A method according to Statement 2, wherein the adenocarcinoma is chosen from esophageal cancers, pancreatic cancers, prostate cancers, cervical cancers, stomach cancers, colorectal cancers, breast cancers, lung cancers, and bile duct cancers Statement 4. A method according to Statement 2, wherein the adenocarcinoma is pancreatic ductal adenocarcinoma (PDAC).

Statement 5. A method according to any one of the preceding Statements, wherein the CPSF3 inhibitor has the following structure:

(JTE-607)

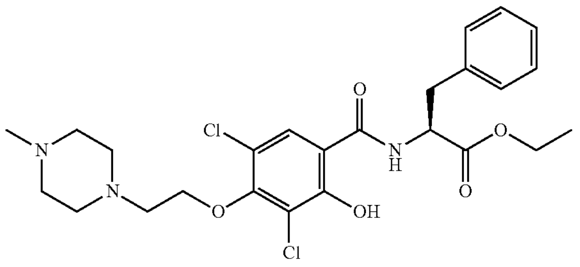

or a pharmaceutically acceptable salt thereof.

Statement 6. A method according to Statement 5, wherein JTE-607 is an HCl salt.

Statement 7. A method according to any one of the preceding Statements, wherein the composition further comprises one or more cell cycle checkpoint inhibitors, one or more chromatin modifying drugs, one or more chemotherapy drugs, one or more EGFR inhibitors, or combinations thereof.

Statement 8. A method according to Statement 7, wherein the one or more chromatin modifying drugs is CBL0137.

Statement 9. A method according to Statement 7 or Statement 8, wherein the one or more chemotherapy drugs are chosen from gemcitabine, leucovorin calcium (folinic acid), fluorouracil, irinotecan hydrochloride, oxaliplatin, and the like, and combinations thereof.

Statement 10. A method according to any one of Statements 7-9, wherein the one or more EGFR inhibitors are chosen from afatinib, osmiertinib, and the like, and a combination thereof.

Statement 11. A method for attenuating PDAC cell proliferation and colony formation comprising contacting a plurality of PDAC cells with JTE-607.

Statement 12. A composition comprising (i) JTE-607 and (ii) comprises one or more cell checkpoint inhibitors, one or more chromatin modifying drugs, one or more chemotherapy drugs, one or more EGFR inhibitors, or combinations thereof.

Statement 13. A composition according to Statement 12, wherein the one or more chromatin modifying drugs is CBL0137.

Statement 14. A composition according to Statement 12 or Statement 13, wherein the one or more chemotherapy drugs are chosen from gemcitabine, leucovorin calcium (folinic acid), fluorouracil, irinotecan hydrochloride, oxaliplatin, and the like, and combinations thereof.

Statement 15. A composition according to any one of Statements 12-14, wherein the one or more EGFR inhibitors are chosen from afatinib, osmiertinib, and the like, and a combination thereof.

Statement 16. A composition according to any one of Statements 12-15, further comprising a pharmaceutically acceptable carrier.

Statement 17. A method for treating cancer, the method comprising administering to an individual in need thereof one or more agents that disrupts alternative polyadenylation (APA).

Statement 18. A method for treating cancer, the method comprising administering to an individual in need thereof one or more agents that disrupt the expression or function of CPSF3.

Statement 19. A method according to Statements 17 or 18, wherein the individual has an epithelial cancer.

Statement 20. A method according to any one Statements 17-20, wherein the individual has pancreatic cancer.

Statement 21. A method according to Statement 21, wherein the pancreatic cancer comprises Pancreatic ductal adenocarcinoma (PDAC).

The following example is presented to illustrate the present disclosure. It is not intended to be limiting in any matter.

EXAMPLE

This example provides a description of a method of the present disclosure.

Pancreatic ductal adenocarcinoma (PDAC) is a lethal disease with limited effective treatment options, potentiating the importance of uncovering novel drug targets. Described herein is the targeting of Cleavage and Polyadenylation Specificity Factor 3 (CPSF3), the endonuclease that catalyzes mRNA cleavage during alternative polyadenylation (APA) and histone mRNA processing. It was found that CPSF3 is highly expressed in PDAC and associated with poor prognosis. CPSF3 knockdown blocks PDAC cell proliferation and colony formation in vitro and tumor growth in vivo. Chemical inhibition of CPSF3 by the small molecule JTE-607 also attenuates PDAC cell proliferation and colony formation, but does not affect cell proliferation of non-transformed pancreatic cells. Mechanistically, JTE-607 induces transcriptional read-through in replication-dependent histones, thus reducing histone supplies, destabilizing chromatin structure and arresting cells in S-phase of the cell cycle. Therefore, CPSF3 represents a potential therapeutic target for the treatment of PDAC.

Described herein is knockdown and/or inhibition of CPSF3 attenuates PDAC cell proliferation in vitro and in vivo. It was found that CPSF3 is highly expressed in PDAC patients and is a predictor of poor outcome. It was found that small molecule inhibition of CPSF3 by JTE-607 selectively attenuates proliferation of PDAC cells but not non-transformed cells. Additionally, a global analysis of CPSF3 disruption was conducted in PDAC, uncovering gene regulatory mechanisms that distinctly affected PDAC cells upon either CPSF3 knockdown or inhibition. A new mechanism by which JTE-607 attenuates cell proliferation, through disruption of replication-dependent histone mRNA processing, thus altering chromatin stability and dysregulating the cell cycle. This description mechanistically addresses the distinction between CPSF3 knockdown and inhibition. Also provided is the connection between CPSF3 inhibition and chromatin stability. Overall, these findings describe new functions of CPSF3 in cancer and nominate CPSF3 as a novel therapeutic target in PDAC.

CPSF3 is upregulated in human PDAC and required for PDAC cell proliferation. To determine the clinical significance of CPSF3 expression in PDAC, gene expression data from the Clinical Proteomic Tumor Analysis Consortium (CPTAC) was analyzed. CPSF3 expression was significantly higher in PDAC tumors (n=135), as compared with non-tumor adjacent tissues (n=18) and normal pancreata (n=7) (FIG. 1A). Consistent with this finding, CPSF3 expression was also significantly higher in the Pancreatic Adenocarcinoma (PAAD) dataset from The Cancer Genome Atlas (TCGA) (n=147) as compared to normal pancreata (n=165) from The Genotype-Tissue Expression (GTEx) project (FIG. 1B). The relationship between CPSF3 expression and PDAC patient outcome was assessed. Patients with high CPSF3 expression had significantly worse overall survival than patients with low CPSF3 expression (P=0.00164, hazard ratio 5.047 (1.842-13.827)). Specifically, patients in the top quartile of CPSF3 expression had a median survival of 14.2 months, while those in the bottom quartile of CPSF3 expression had a median survival of 33.5 months (FIG. 1C). CPSF3 expression status in the cell line models was assessed. In agreement with the clinical data, it was found that CPSF3 is upregulated in PDAC cell lines (MiaPaCa2, Suit2, Panc1) as compared to non-transformed pancreatic epithelial cells (HPNE, HPDE) by western blot (WB) and RT-qPCR (FIGS. 1D and S1A). Therefore, CPSF3 is highly expressed in PDAC, high expression correlates with poor patient outcome, and these cell models are appropriate for mechanistic studies.

Figure 8:
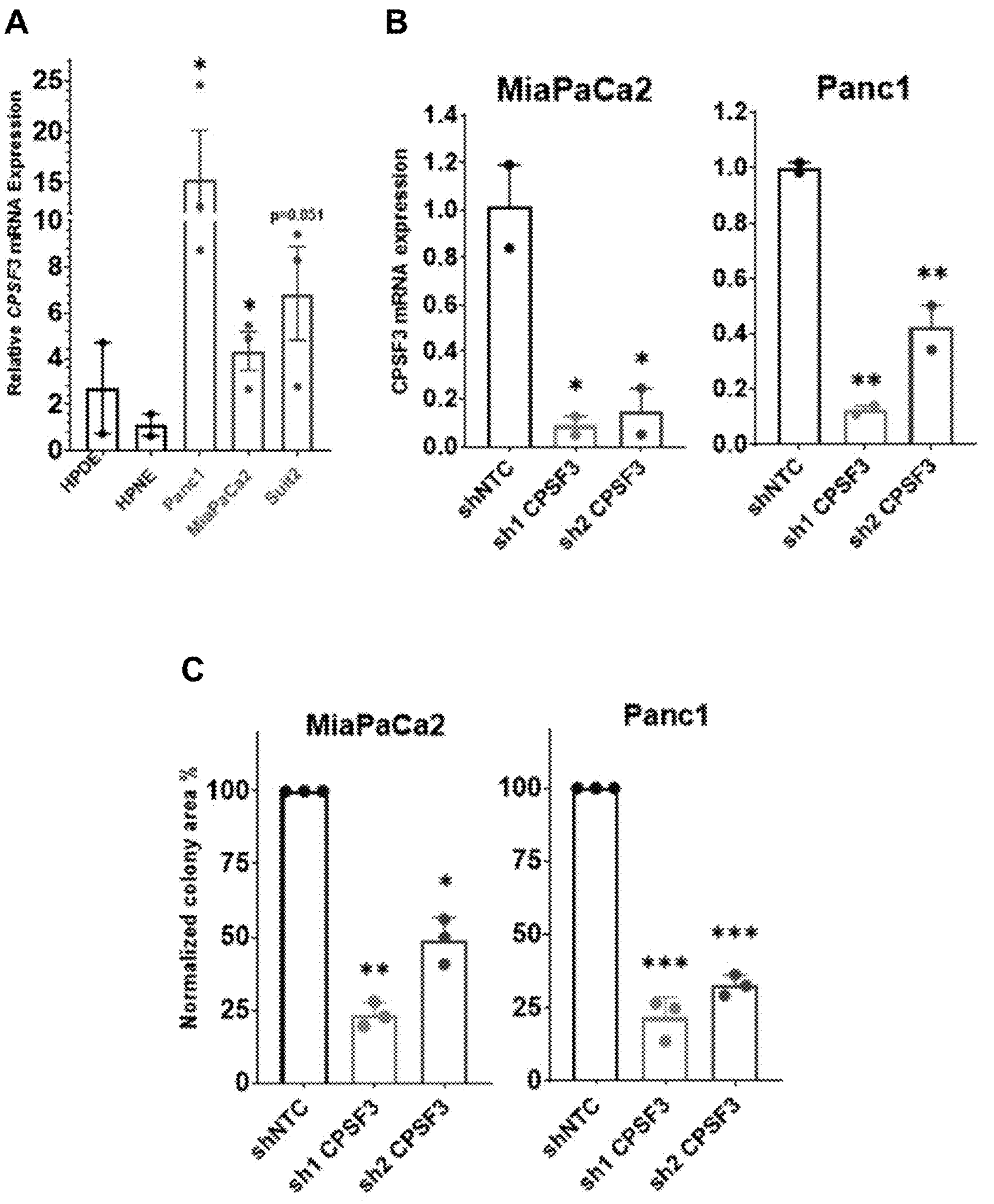
FIG. 8 shows CPSF3 is upregulated and required for PDAC cell clonogenicity, related to FIG. 1. (A) Quantitative RT-PCR showing CPSF3 mRNA expression levels in non-transformed pancreatic epithelial and PDAC cells. Data are shown as mean±SEM.*, P<0.05, unpaired t test with Welch's correction. (B) mRNA expression of CPSF3 in shNTC, sh1 CPSF3 and sh2 CPSF3 knockdown cells by qPCR. Graphs are representative of at least two independent experiments. Data are shown as mean±SEM of technical duplicates. , P<0.01, Ordinary one-way ANOVA with Dunnett's multiple comparisons test. (C) Normalized colony area percentage of shNTC, sh1 and sh2 CPSF3 knockdown cells from (FIG. 1**G). *, P<0.05; , P<0.01; *, P<0.001; Ordinary one-way ANOVA with Dunnett's multiple comparisons test. (D) Hematoxylin and Eosin (H&E) staining of xenograft tumors.
Figure 8:
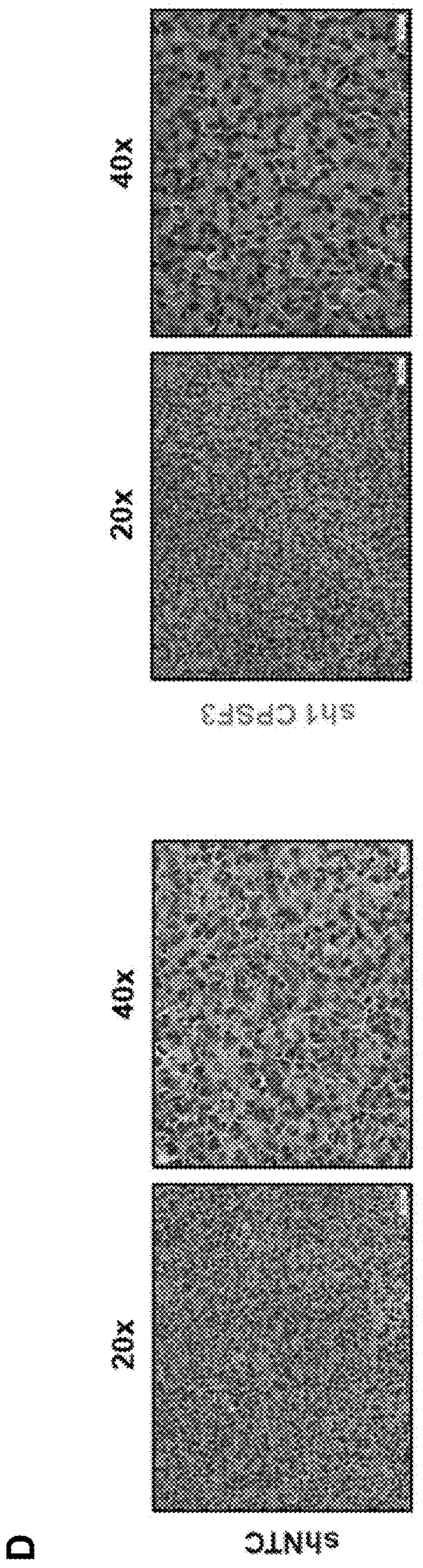

To define the functional role of CPSF3 in PDAC, a genetic approach was used and stable CPSF3 knockdown MiaPaCa2 and Panc1 cells were generated. Two different short hairpin RNAs (sh1 and sh2) targeting CPSF3 were generated, and a non-targeting control (shNTC). Successful knockdown of CPSF3 was confirmed at the protein and RNA level by WB and RT-qPCR, respectively, with sh1 cells having the highest level of knockdown in both cell lines (FIGS. 1E and S1B). The effect of CPSF3 knockdown on cell proliferation and colony formation capability was examined. CPSF3 knockdown significantly attenuated proliferation as compared with shNTC controls in both MiaPaCa2 and Panc1 cells (FIG. 1F). CPSF3 knockdown also significantly decreased colony formation (FIGS. 1G and 8C). In both the proliferation and colony formation assays, and in both PDAC cell lines, sh1 CPSF3 had the strongest phenotype, consistent with higher levels of CPSF3 knockdown. The requirement for CPSF3 in PDAC tumor growth in vivo was determined. MiaPaCa2 cells (either shNTC or sh1 CPSF3, $5\times10^5$ per mouse) were subcutaneously implanted into the flanks of NOD/SCID/IL2R$\gamma^{-/-}$ (NSG) mice. CPSF3 knockdown tumors grew significantly slower, and weighed significantly less at endpoint, than shNTC tumors (FIGS. 1H-1J). No changes in tumor histopathology were noted by Hematoxylin and Eosin (H&E) staining (FIG. 8D). Immunohistochemical (IHC) analysis revealed that CPSF3 knockdown was maintained in vivo (FIG. 1K). Finally, IHC for Ki67 revealed a significant decrease in proliferation in CPSF3 knockdown tumors as compared with shNTC controls (FIG. 1L). Overall, these data support the requirement for CPSF3 in PDAC cell proliferation and tumor growth.

Figure 2:
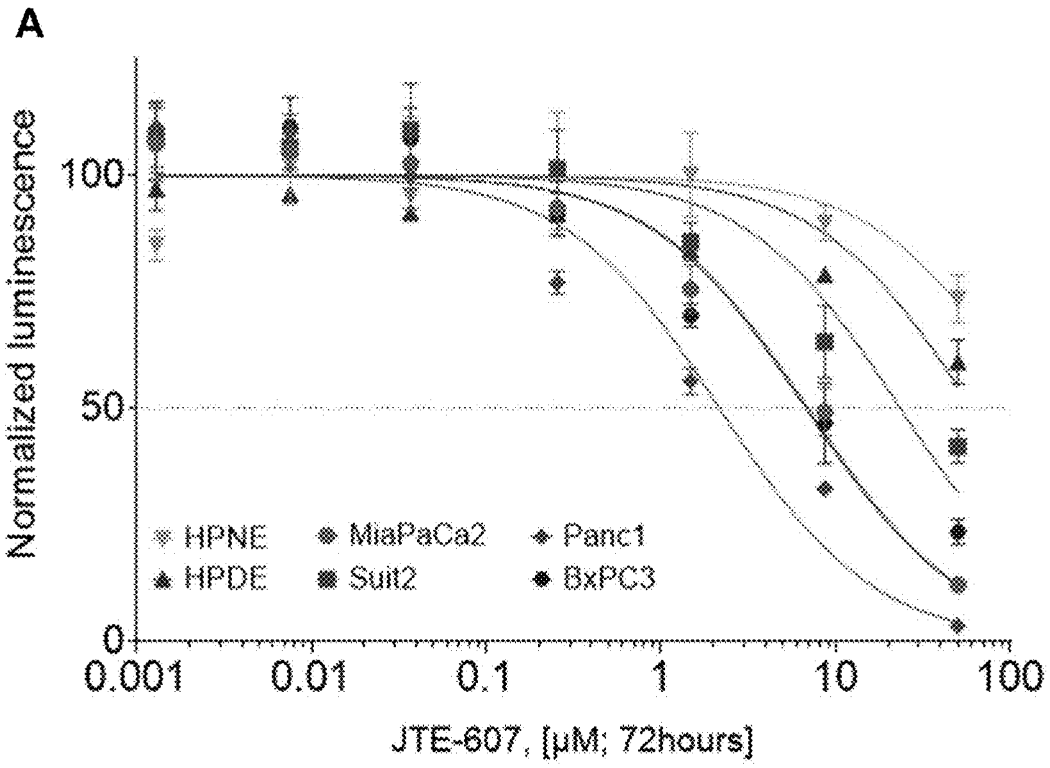
FIG. 2 shows PDAC cell lines are sensitive to CPSF3 inhibition by JTE-607. (A) IC50 of JTE-607 on non-transformed and PDAC cell lines after 72-hours of treatment. (B) IC50 of JTE-607 on human fibroblast C7 and PancPat CAFs after 72-hours of treatment. (C-E) Proliferation rates at days 0, 2, 4 and 6 of non-transformed and PDAC cell lines after treatment with escalating concentrations of JTE-607. *, P<0.05; 2way ANOVA with Dunnett's multiple comparisons test. Data are shown as mean±SEM. (F) Clonogenic growth assay of PDAC cell lines after treatment with increasing concentration of JTE-607. (G) Normalized colony area percentage of PDAC cell lines from (F). *, P<0.01; , P<0.001; *, P<0.0001; Ordinary one-way ANOVA with Dunnett's multiple comparisons test. Data are shown as mean±SEM.
Figure 2:
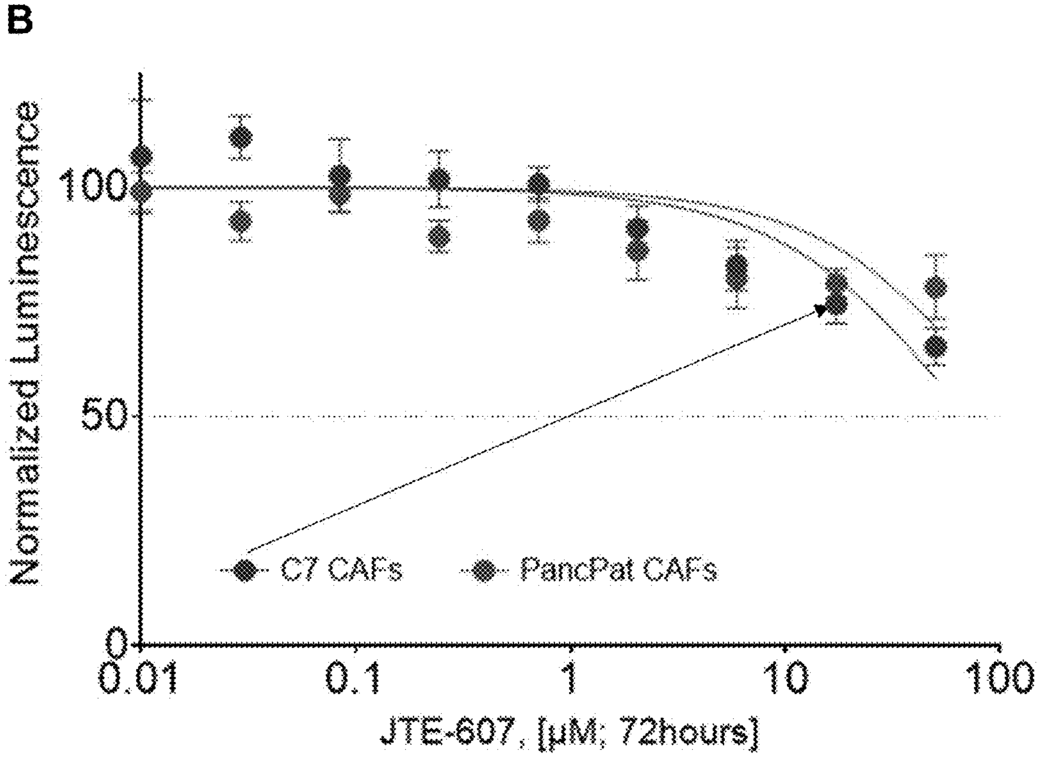
Figure 2:
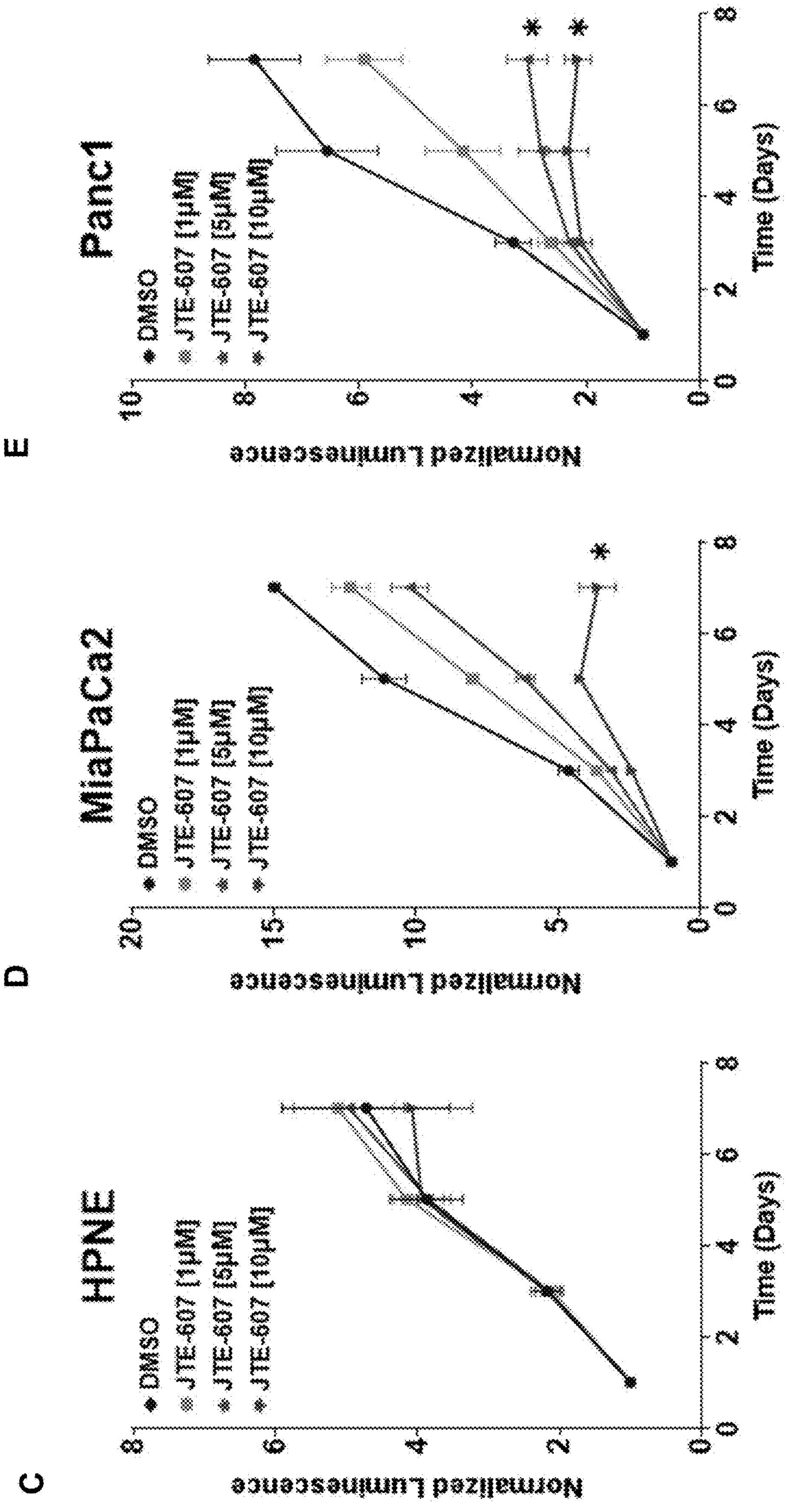
Figure 2:
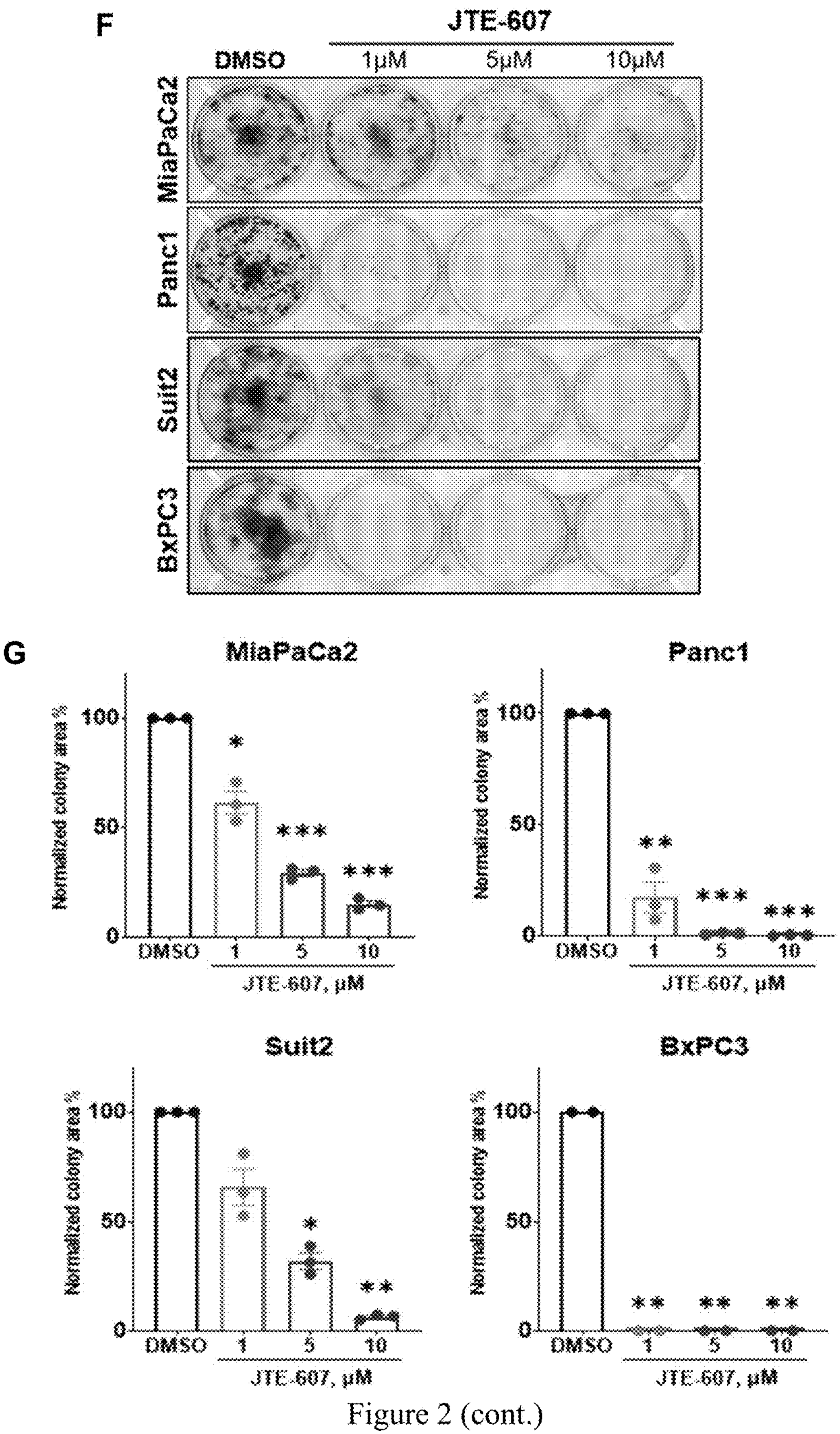
Figure 3:
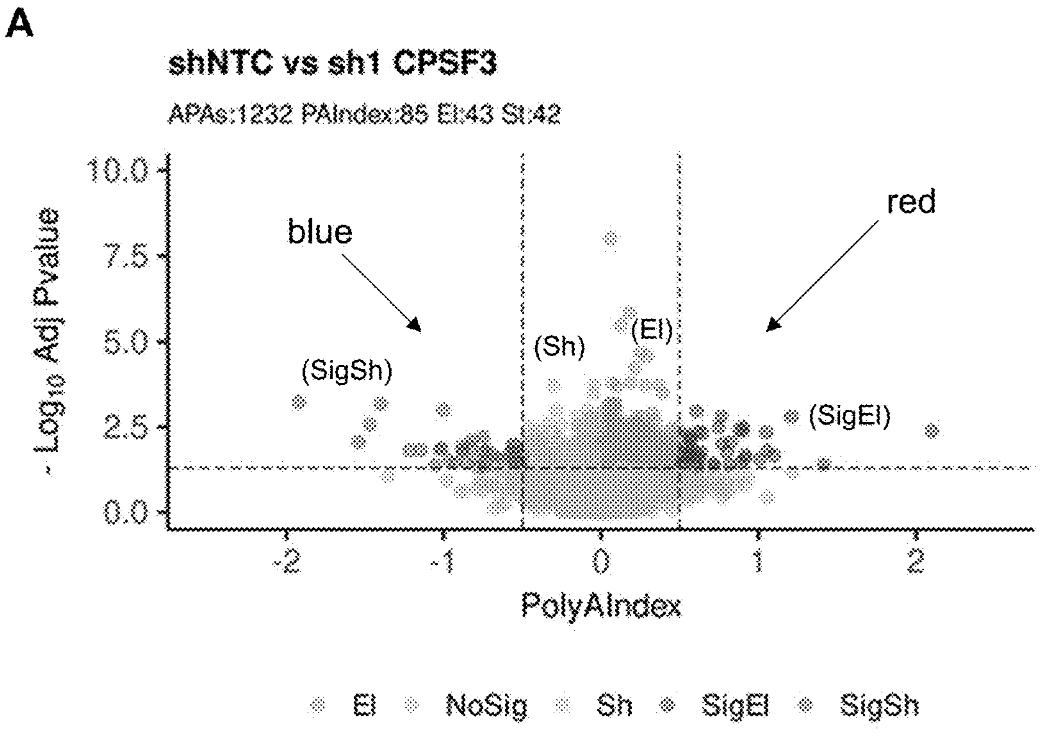
FIG. 3 shows mRNA regulation is distinct between CPSF3 knockdown and inhibition. (A, B) Volcano plots showing differential APA genes (−0.5>PolyAIndex>0.5; P<0.05). Red dots indicate 3'-UTR shortening (St) while blue dots indicate 3'-UTR lengthening (El). St=42 and 36 upon CPSF3 knockdown and inhibition, respectively. El=43 and 138 upon CPSF3 knockdown and inhibition, respectively. (C) Dot plot with quadrants representing APA differences in both CPSF3 knockdown and inhibition. Only 2 genes are uniquely altered in both conditions (Red dots, top-right quadrant). (D) The distribution of the APA binding motif, UGUA, surrounding PASs of genes undergoing shortening events upon CPSF3 knockdown. Green and blue lines represent the distribution of UGUA around the proximal and distal PAS, respectively. (E, F) Motif enrichment analyses of sequences surrounding PASs of APA short (E) and long (F) genes upon CPSF3 knockdown and inhibition.
Figure 3:
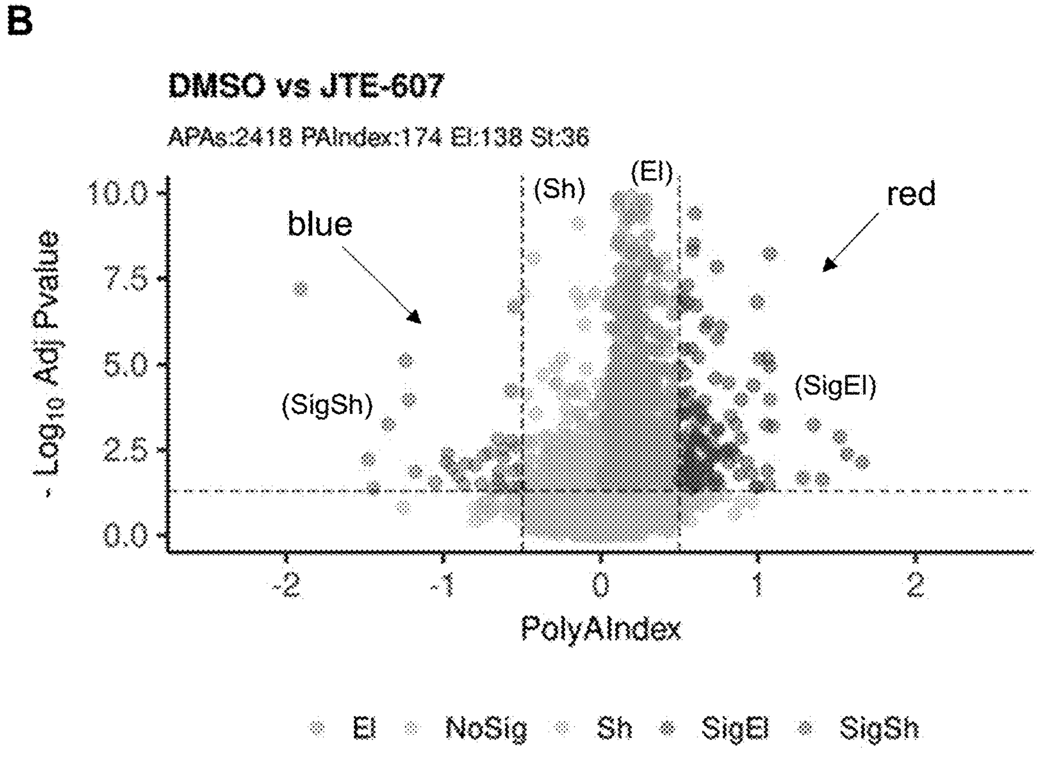
Figure 3:
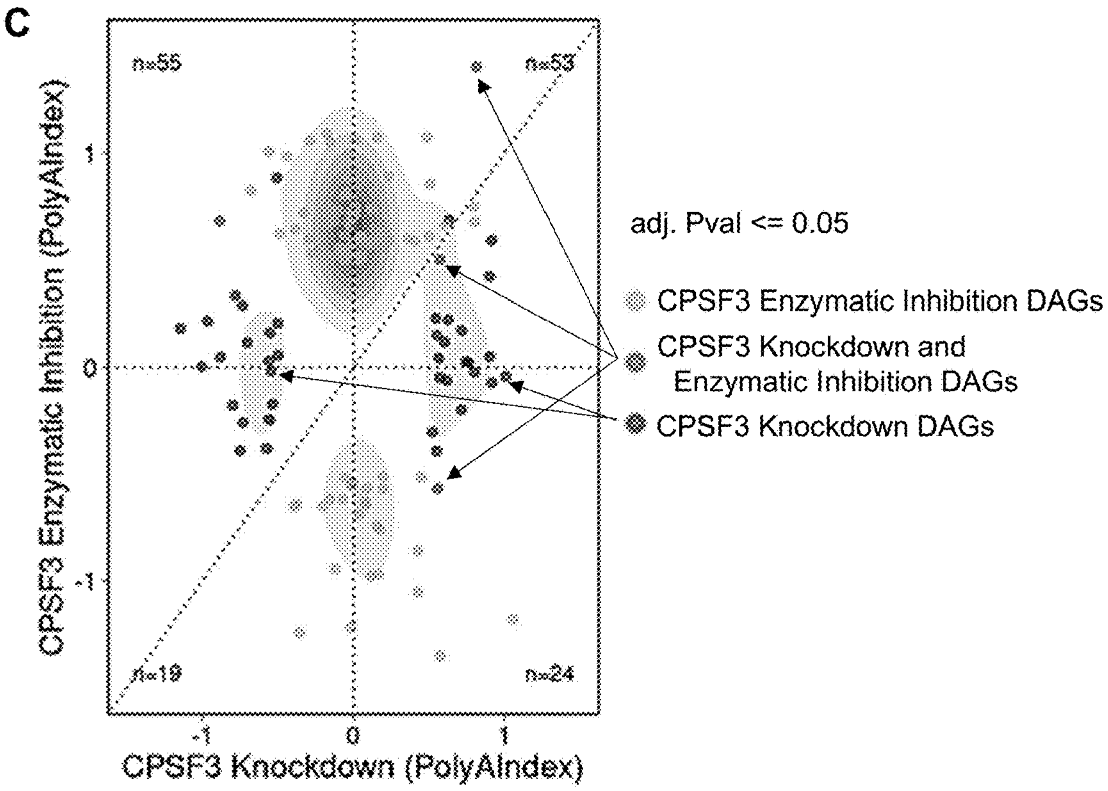
Figure 3:
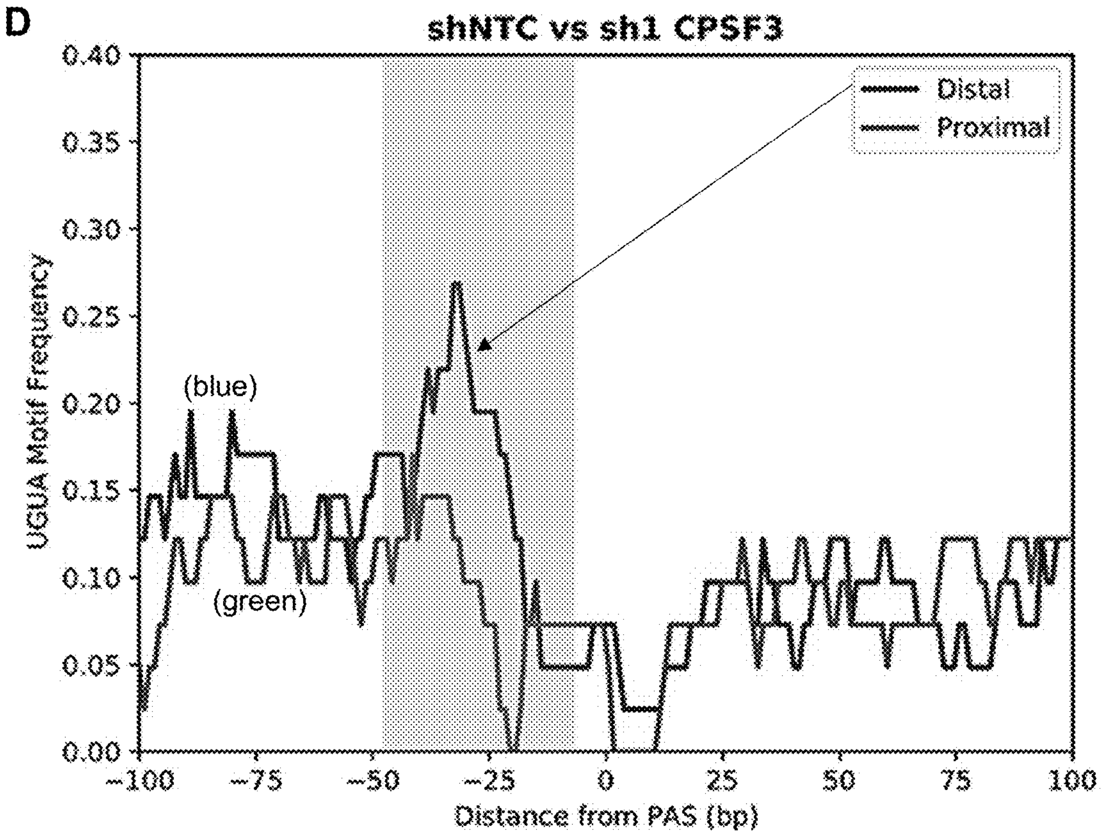
Figure 3:
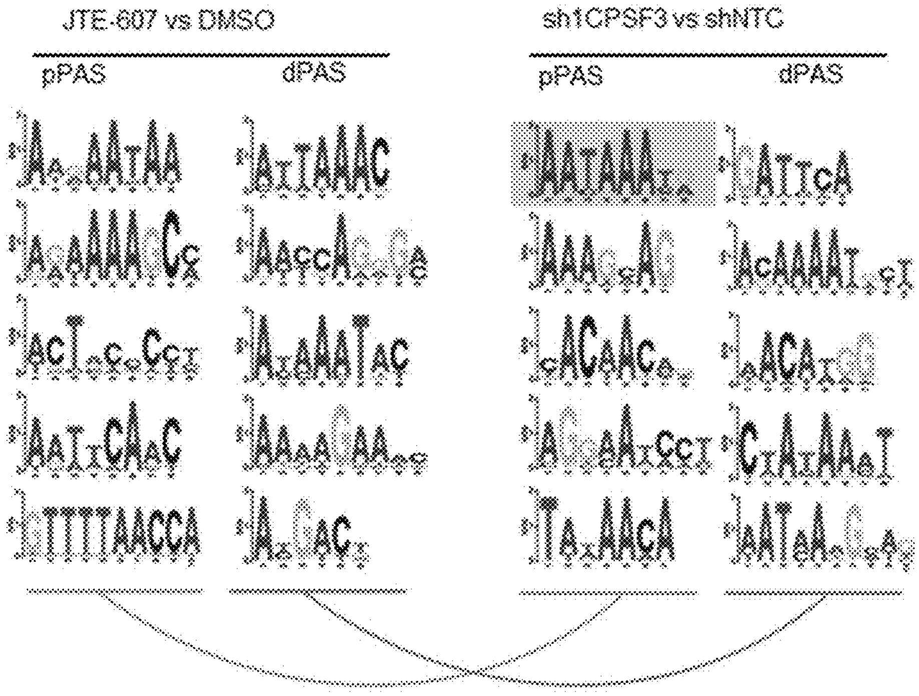
Figure 3:
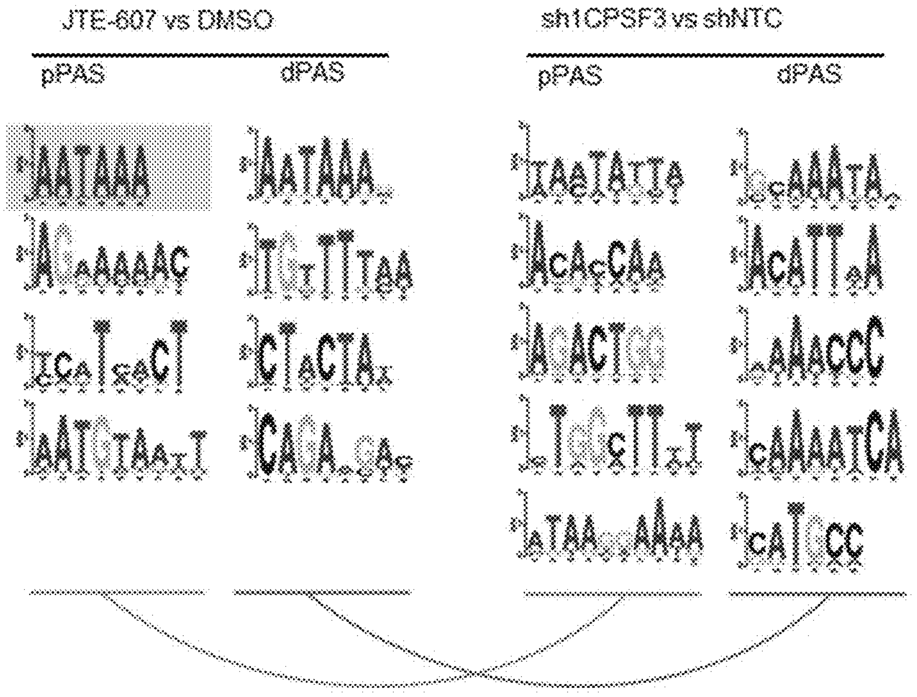
Figure 9:
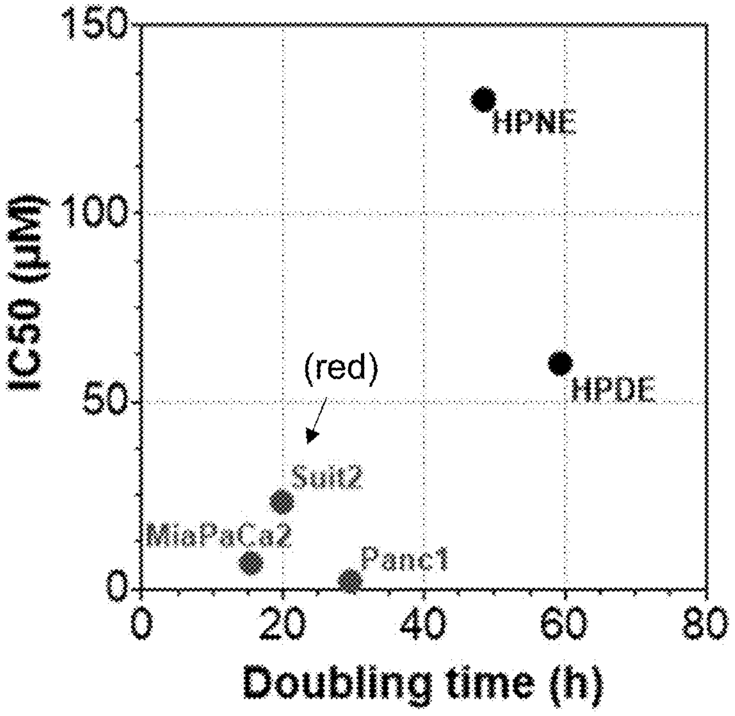
FIG. 9 shows sensitivity to JTE-607 is associated with proliferation rate, related to FIG. 2. (A) IC50s and doubling times of non-transformed and PDAC cell lines. Doubling time is represented in hours. (B) Association between doubling time and IC50 of JTE-607 in pancreatic cell lines. Red denotes PDAC cells while Black denotes non-transformed cell lines.
Figure 10:
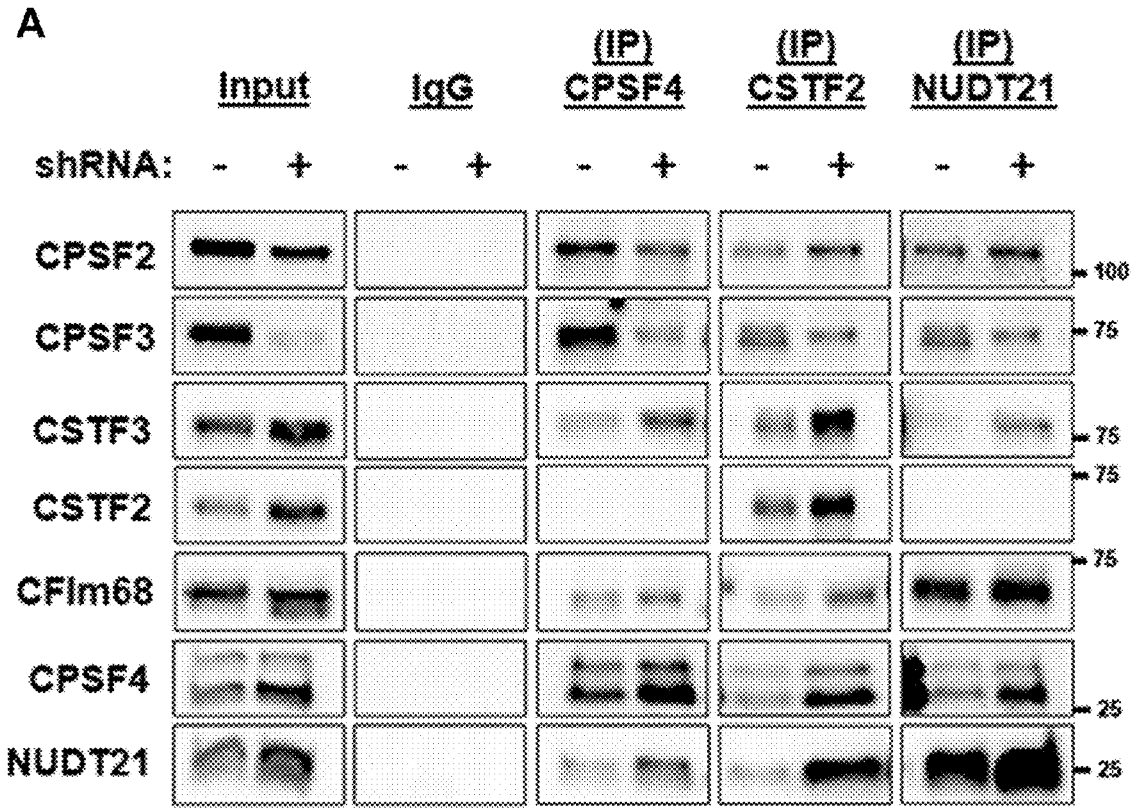
FIG. 10 shows CPSF3 disruption does not rearrange APA complex assembly, related to FIG. 3. (A-C) Western blots of the immunoprecipitation (IP) assay using anti-CPSF4, anti-CSTF2 and anti-NUDT21 to co-immunoprecipitate different components of the APA complex. IP experiments were performed using CPSF3 knockdown (A) and JTE-607 treated cells (B and C). (D, E) Volcano plots of differentially expressed genes upon CPSF3 knockdown and inhibition, respectively. Blue and Red dots indicate downregulated and upregulated genes, respectively (FC>1.5, Adjusted P-value <0.05). Grey dots are not differentially expressed. Multiple APA genes are labeled. (F) The distribution of the APA binding motif, UGUA, surrounding PASs of genes undergoing shortening events upon CPSF3 inhibition by JTE-607. Green and blue lines represent the distribution of UGUA around the proximal and distal PAS, respectively.
Figure 10:
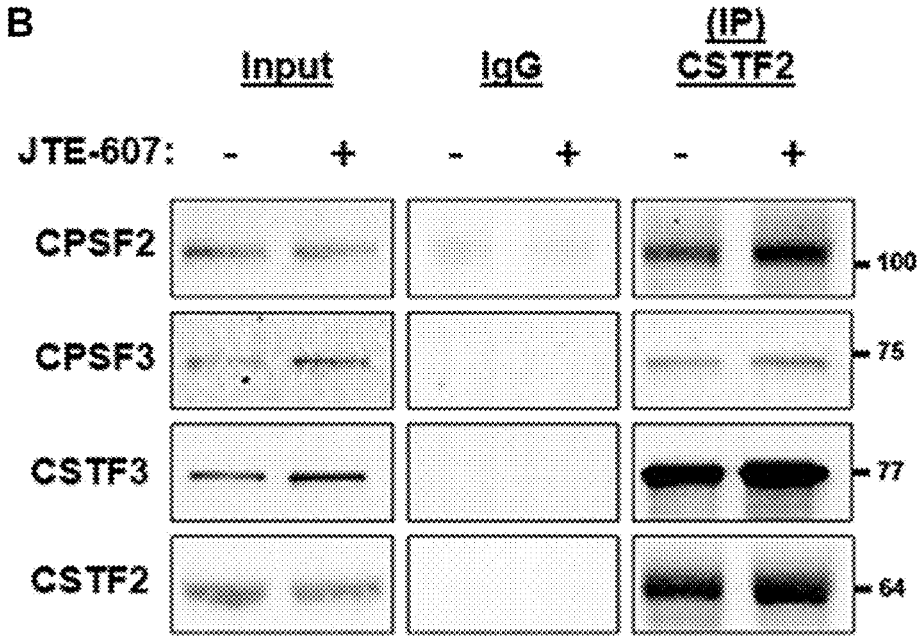
Figure 10:
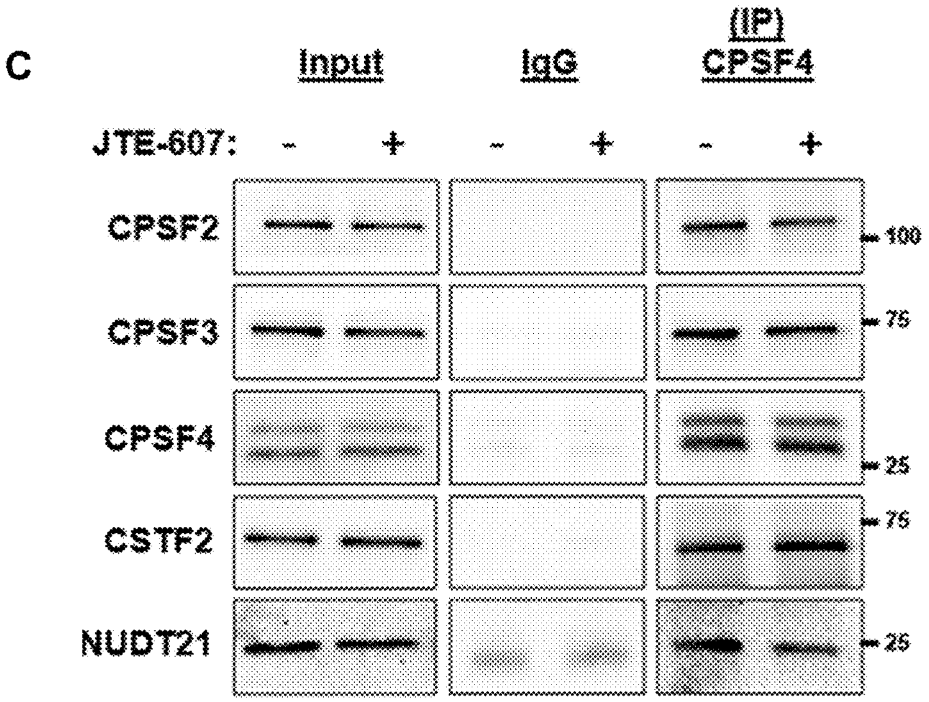
Figure 10:
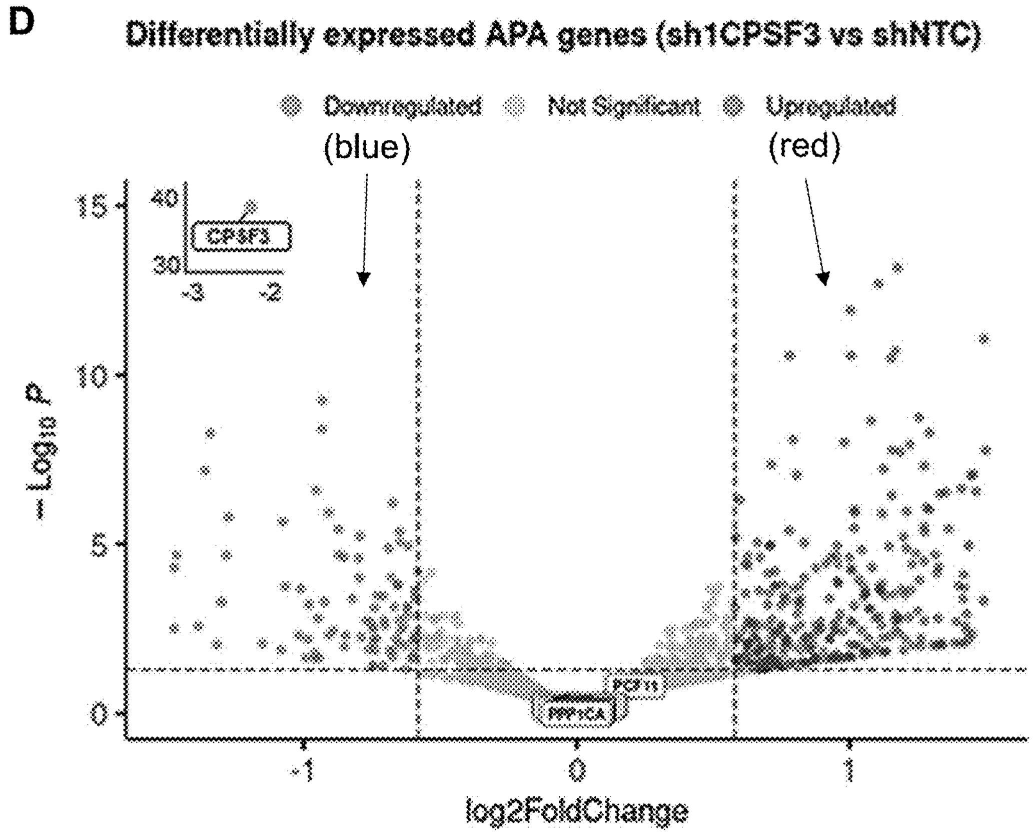
Figure 10:
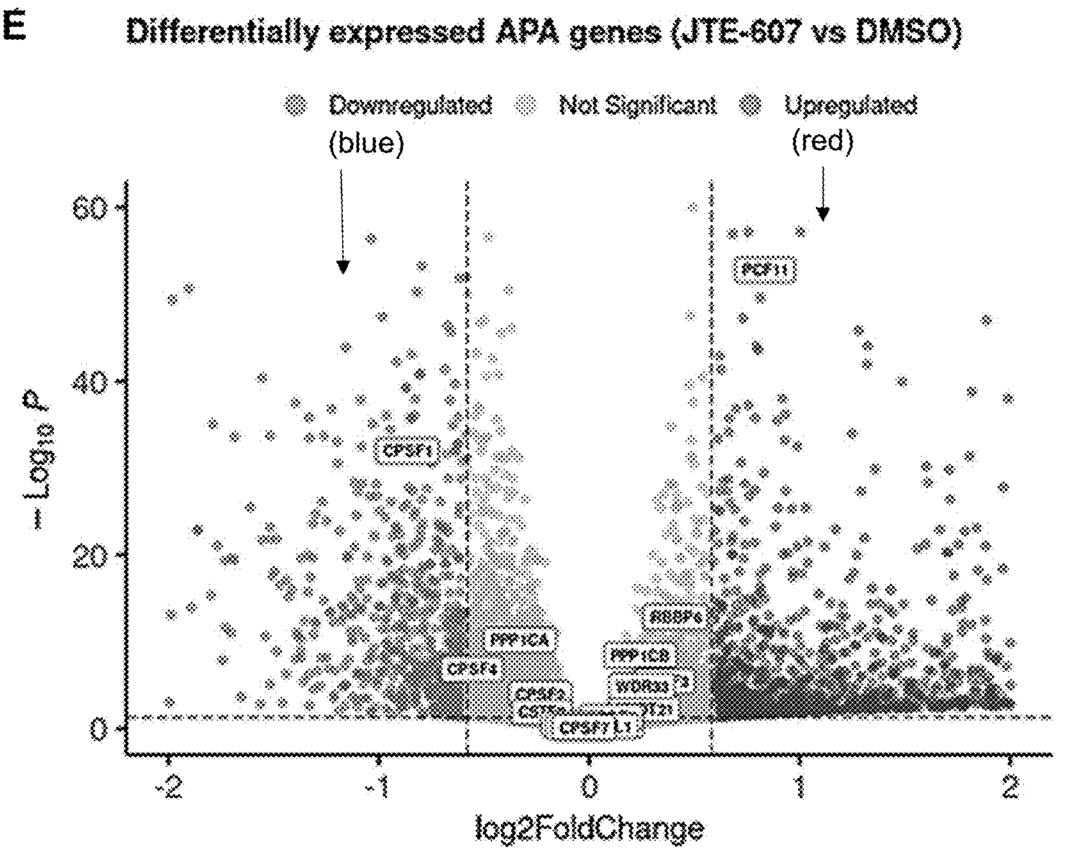
Figure 10:
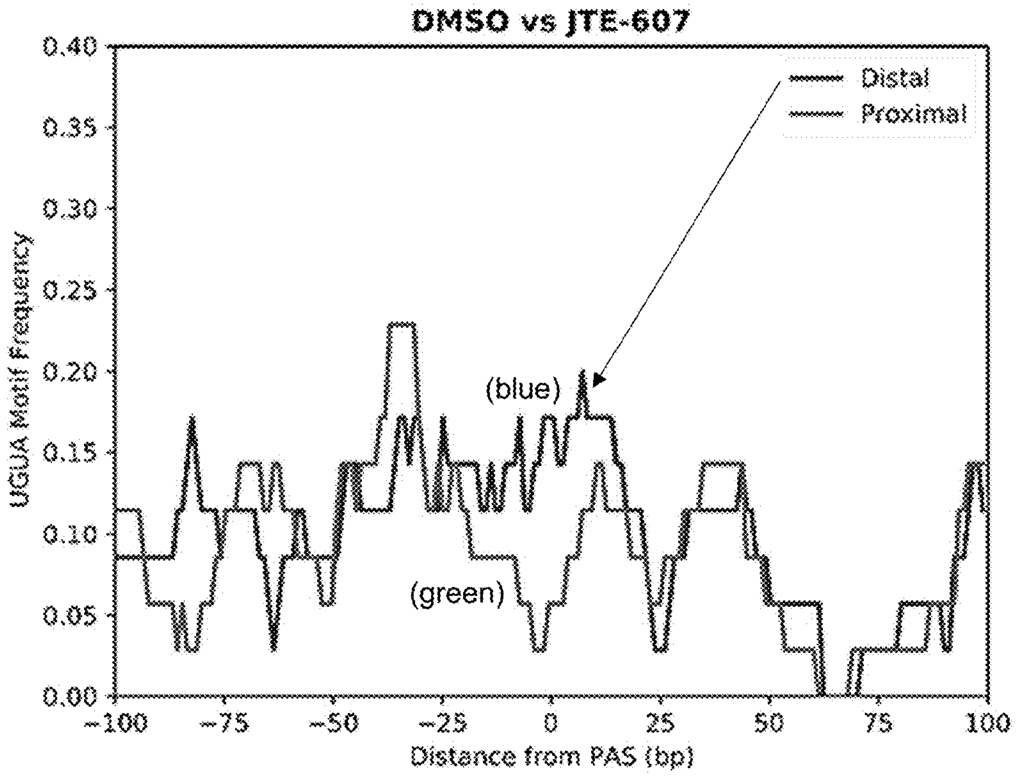

PDAC cells are sensitive to chemical inhibition of CPSF3. CPSF3 was recently identified as the target for the small molecule JTE-607. JTE-607 is a prodrug that, when metabolized by the ester hydrolyzing enzyme carboxylesterase 1 (CES1), binds to CPSF3 and inhibits its catalytic activity, impairing the processing of newly synthesized mRNAs. As genetic depletion of CPSF3 attenuated PDAC cell proliferation (FIG. 1), it 2 as hypothesized that pharmacologic inhibition of CPSF3 with JTE-607 could represent a novel therapeutic approach in PDAC. The sensitivity of multiple human pancreatic cell lines, both non-transformed and PDAC, to JTE-607 in a 72-hour dose-response cell viability assay was examined. Non-transformed pancreatic epithelial cells (HPNE, IC50=130.4 μM; HPDE, IC50=60.11 μM) and human cancer associated fibroblast cell lines (C7 CAF, IC50=70.04 μM; PancPat CAFs, IC50=114.2 μM) were not sensitive to JTE-607 (FIGS. 2A, 2B and 9A). In contrast, human PDAC cell lines displayed a range of sensitivities to JTE-607, with Panc1 cells being the most sensitive (IC50=2.163 μM) (FIGS. 2A and 9A). To examine if sensitivity to CPSF3 inhibition was associated with proliferation rate, the relationship between cell line doubling time and JTE-607 sensitivity was assessed. It was found that highly proliferative cells are indeed more sensitive to JTE-607 (FIGS. 9A and 9B). Next, the effect of JTE-607 on cell proliferation by treating cells with increasing concentrations of JTE-607 and assessing cell viability in a time-dependent fashion (FIGS. 2C-2E) was determined. JTE-607 had no effect on proliferation in non-transformed HPNE cells (FIG. 2C). However, proliferation of MiaPaCa2 and Panc1 PDAC cells was significantly attenuated by JTE-607, in a dose-dependent manner (FIGS. 2D and 2E). Finally, the effect of JTE-607 on colony formation in PDAC cell lines was tested. JTE-607 significantly decreased colony formation in all PDAC cell lines tested (FIGS. 2F and 2G). Therefore, JTE-607 selectively attenuates proliferation of PDAC cells over non-transformed pancreatic cells.

mRNA regulation is distinct between knockdown and chemical inhibition of CPSF3. Because JTE-607 inhibits CPSF3 catalytic activity without inducing target degradation, it was sought to understand if the function of CPSF3 is distinct between knockdown and inhibition. As CPSF3 is an integral component of the polyadenylation complex and the histone cleavage complex (HCC), it was hypothesized that CPSF3 disruption would dysregulate both alternative polyadenylation (APA) and histone mRNA processing. To test this hypothesis, CPSF3 knockdown and JTE-607 treated Panc1 cells were subjected to RNA-sequencing (RNA-seq). Next, APA analysis was performed using polyAMiner-Bulk to uncover significantly altered changes in 3'-UTR length. Briefly, polyAMiner-Bulk detects alternative polyadenylation alterations from bulk RNA-seq data (see below for details) by generating a poly A index score (PolyAIndex) for each gene based on the relative abundances of 3'-UTR long and short forms. Cleavage at a proximal polyadenylation signal (pPAS) generates a short 3'-UTR, while cleavage at a distal polyadenylation signal (dPAS) generates a long 3'-UTR. A negative PolyAIndex indicates a shortening event, and a positive PolyAIndex indicates 3'-UTR lengthening. To identify differential APA genes (DAGs) with minimum false positives/negatives and better understand the differences between knockdown and inhibition, we chose a stringent PolyAIndex threshold ($-0.5>$PolyAIndex$>0.5$; Padj$<0.05$) (Table S1 (attached as a Large Table)). In the CPSF3 knockdown cells, PolyAMiner-Bulk detected 85 significant DAGs, of which 43 genes underwent 3'UTR lengthening (PolyAIndex$>0.5$; Padj$<0.05$) and 42 genes underwent 3'UTR shortening (PolyAIndex$<-0.5$; Padj$<0.05$) (FIG. 3A). In the CPSF3 inhibition model, PolyAMiner-Bulk detected 174 significant DAGs, of which 138 underwent 3'UTR lengthening (PolyAIndex$>0.5$; Padj$<0.05$) and 36 genes underwent 3'UTR shortening (PolyAIndex$<-0.5$; Padj$<0.05$) (FIG. 3B). Of note, JTE-607 exhibited more DAGs than CPSF3 knockdown, with genes undergoing lengthening events being the most predominant. Surprisingly, however, the DAGs identified in both CPSF3 knockdown and inhibition do not converge, with only two shared DAGs altered in the same-direction between both conditions (FIG. 3C). To determine if these distinct patterns are due to differences in APA complex assembly upon CPSF3 knockdown or inhibition, immunoprecipitation (IP) experiments were performed to pull-down multiple APA complexes. It was found that neither CPSF3 knockdown nor inhibition induced dramatic rearrangement of the APA complex (FIGS. 10A-10C). Intriguingly, CPSF3 knockdown, but not JTE-607, decreased basal protein levels of multiple APA factors (FIGS. 10A-10C, input columns). However, knockdown or inhibition of CPSF3 did not largely affect APA factor expression on the mRNA level (FIGS. 10D and 10E), indicating that the effect of CPSF3 knockdown on APA factor expression is not transcriptional.

To better understand the difference between knockdown and inhibition, which type of cis-elements are regulated in both conditions was examined, thus influencing PAS selection. To address this question, two independent motif enrichment analyses were performed. First, the distribution of the UGUA motif was examined, which interacts with APA components and prevents the CPSF subunits from interacting with proximal PASs, thus inducing lengthening of genes. Therefore, genes that underwent shortening in both conditions were utilized and examined the UGUA enrichment within their 3'UTR. Significant enrichment for UGUA motifs near distal PASs (~25-50 bp upstream) was found compared to the proximal PASs within the 3'UTR of genes that exhibit shortening changes following CPSF3 knockdown (FIG. 3D, pink highlight). These results indicate that CPSF3 strongly binds at distal PASs of the unique 3'UTR shortened genes and that CPSF3 knockdown shifts this PAS selection to a proximal PAS. On the other hand, CPSF3 inhibition by JTE-607 did not show consistent distribution patterns of the UGUA motif (FIG. 10G), which suggested that enzymatic inhibition of CPSF3 may rely on other cis-elements to direct PAS selection. To identify which cis-elements are enriched upon both CPSF3 knockdown and inhibition, the genes that are uniquely identified as undergoing 3'UTR lengthening or shortening in both experiments were used and motif enrichment analysis was performed within the 50 bp upstream and downstream of the most proximal and most distal PASs. It was found distinct motif enrichment across CPSF3 knockdown and inhibition at both proximal and distal PASs (FIGS. 3E and 3F). For example, genes undergoing shortening upon CPSF3 knockdown were enriched for the canonical PAS AATAAA within the pPAS (FIG. 3E, pink highlight). In contrast, AATAAA was enriched within the pPAS of lengthened genes upon JTE-607 treatment (FIG. 3F, blue highlight). This difference suggests selection for different PASs, thus supporting the notion that CPSF3 knockdown and inhibition differentially regulate mRNA processing.

JTE-607 inhibits expression of replication-dependent histones. JTE-607 induces global transcriptional read-through in Ewing's sarcoma cells. Therefore, it was asked whether JTE-607 would similarly induce global read-through in PDAC cells by applying the ARTDeco algorithm. ARTDeco generates density plots of read-through events and the differences between two conditions can be visualized by a shift to the right of the density line (i.e., upregulated read-through events). It was found that JTE-607 did not induce global read-through as only 447 genes (FC>1.5; FDR<0.01) underwent transcriptional read-through genome-wide (FIGS. 11A and Table S2 (attached as a Large Table)). Similarly, CPSF3 knockdown did not induce genome-wide read-through changes as only 69 genes (FC>1.5; FDR<0.01) underwent transcriptional read-through (FIGS. 11B and Table S2 (attached as a Large Table)). Therefore, CPSF3 knockdown and inhibition do not induce global transcriptional read-through events in PDAC cells.

Figure 4:
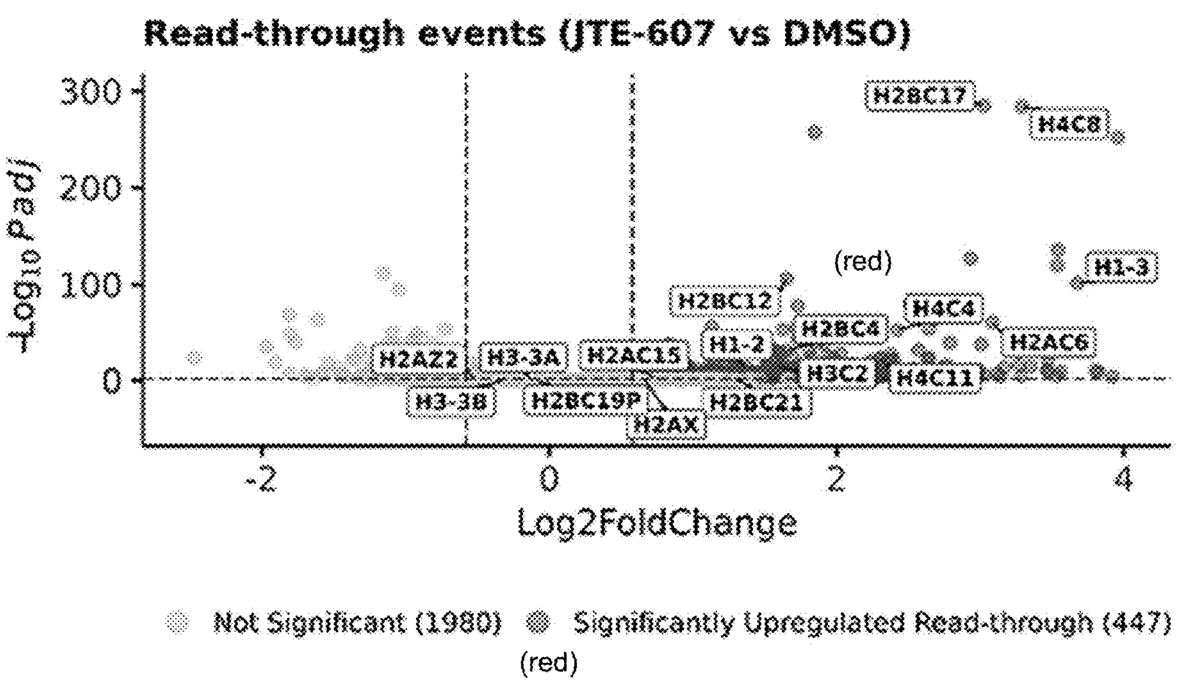
FIG. 4 shows JTE-607 decreases gene expression of replication-dependent histone. (A, B) Volcano plots showing significantly upregulated read-through genes (red dots) with histone genes highlighted upon CPSF3 inhibition (A) and loss (B). (C) Heatmap of top differentially expressed genes upon JTE-607 treatment. Replication-dependent histones are colored in blue. Expression is plotted as transformed expression value. (D) mRNA expression of H2B and H3 in MiaPaCa2 cells treated with JTE-607. *, P<0.05, , P<0.01, *, P<0.001, Ordinary one-way ANOVA with Dunnett's multiple comparisons test. (E) DSeq2 normalized counts of H3F3A and H2AZ1 histone variants (replication-independent) in Panc1 cells treated with JTE-607. **, P<0.001. (F-H) Volcano plots of Spearman's correlation of CPSF3 and all histone genes (F), replication-dependent histone genes (G) and replication-independent histone genes (H). Each dot represents a histone gene. Blue and red dots denote positive and negative correlation, respectively. (Spearman=−0.15>R>0.15, P<0.05).
Figure 4:
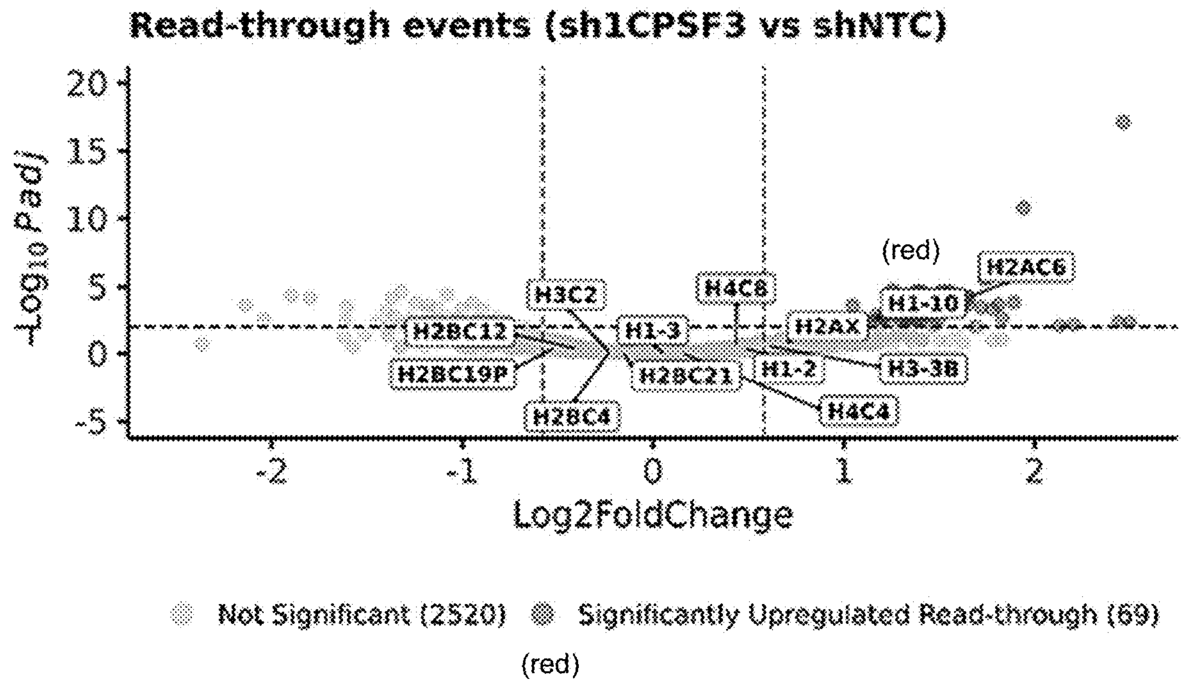
Figure 4:
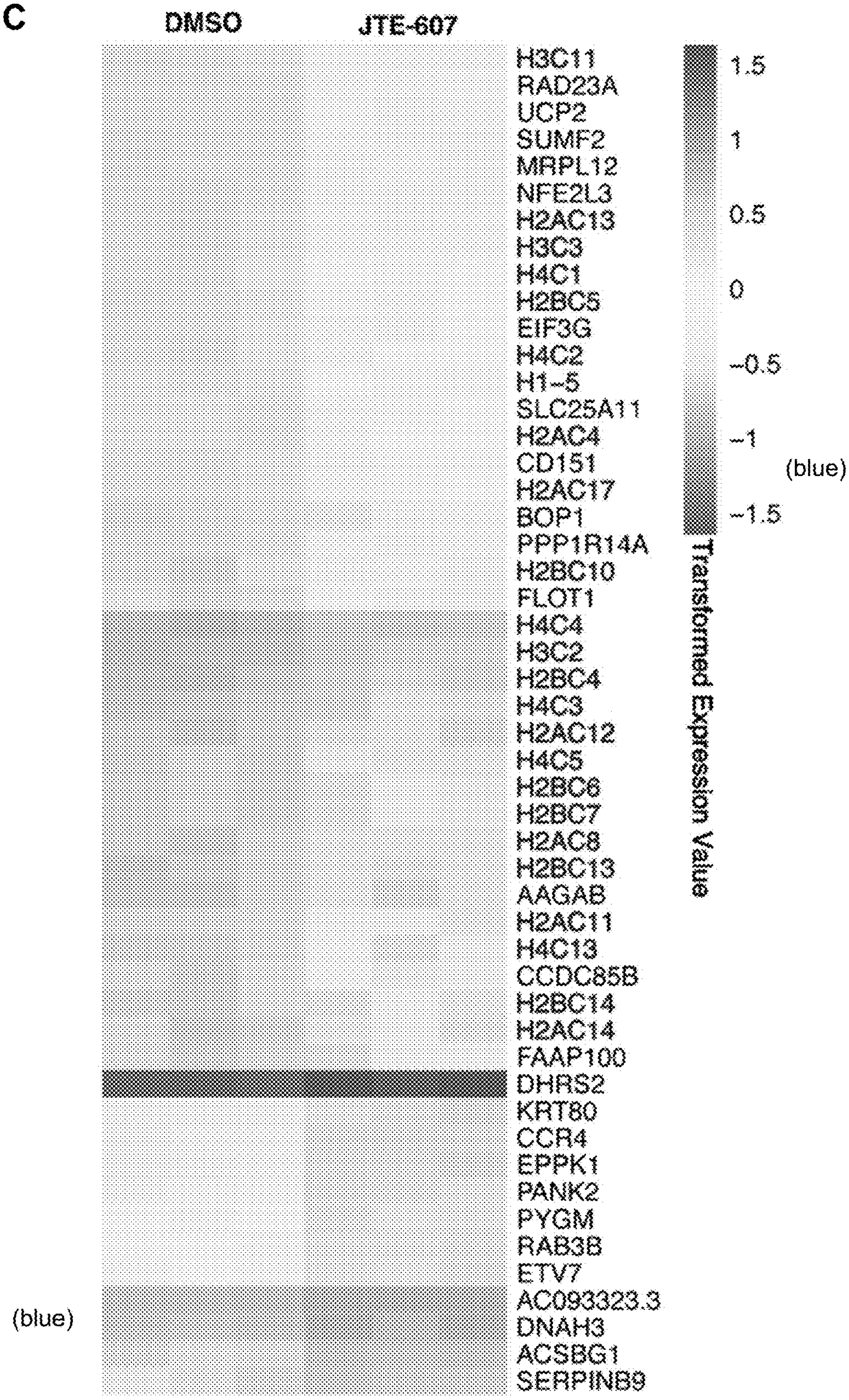
Figure 4:
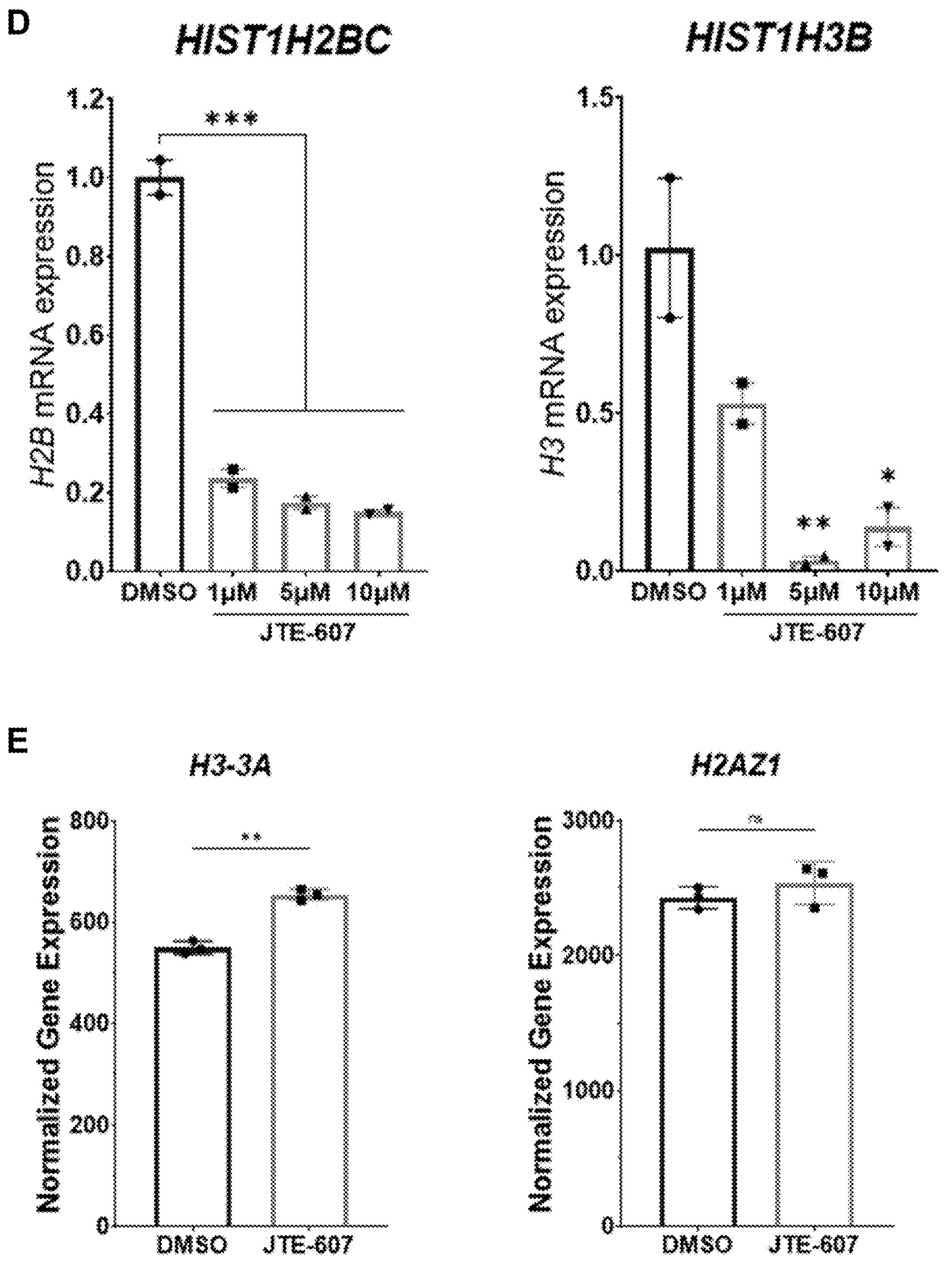
Figure 4:
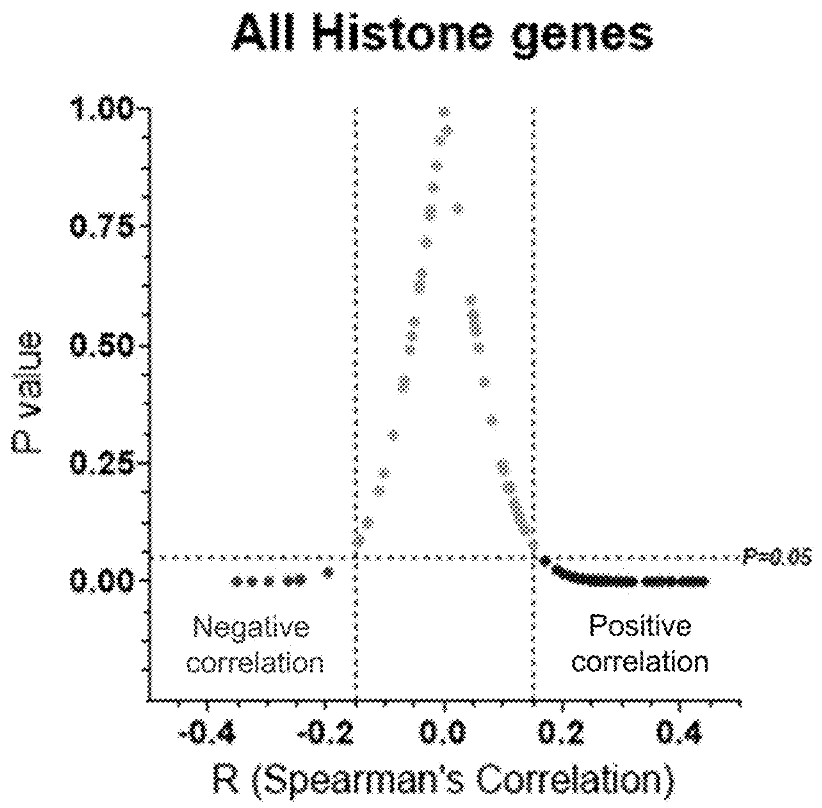
Figure 4:
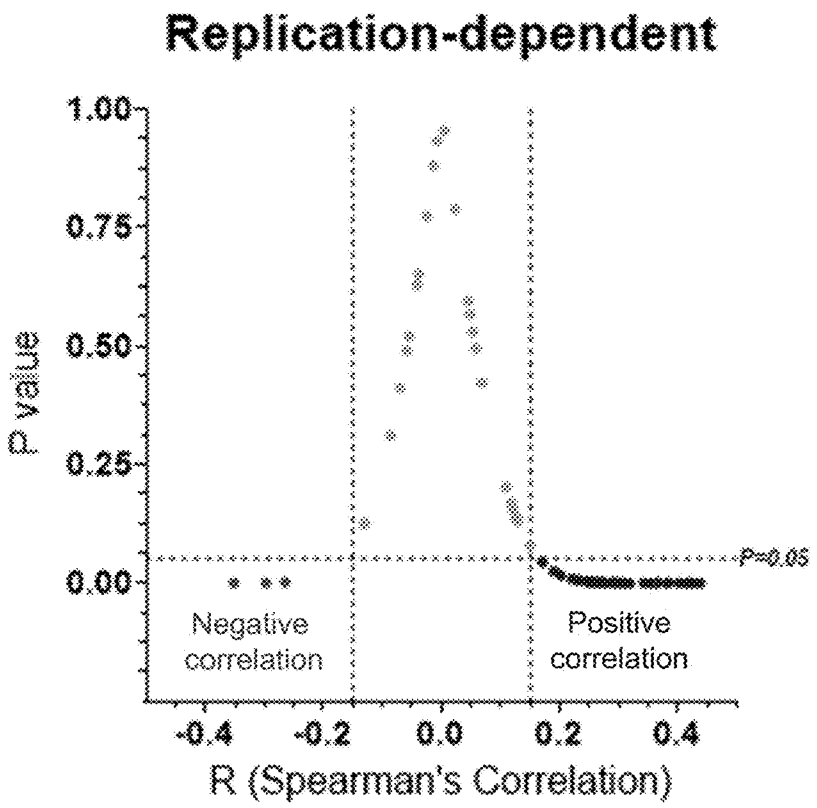
Figure 4:
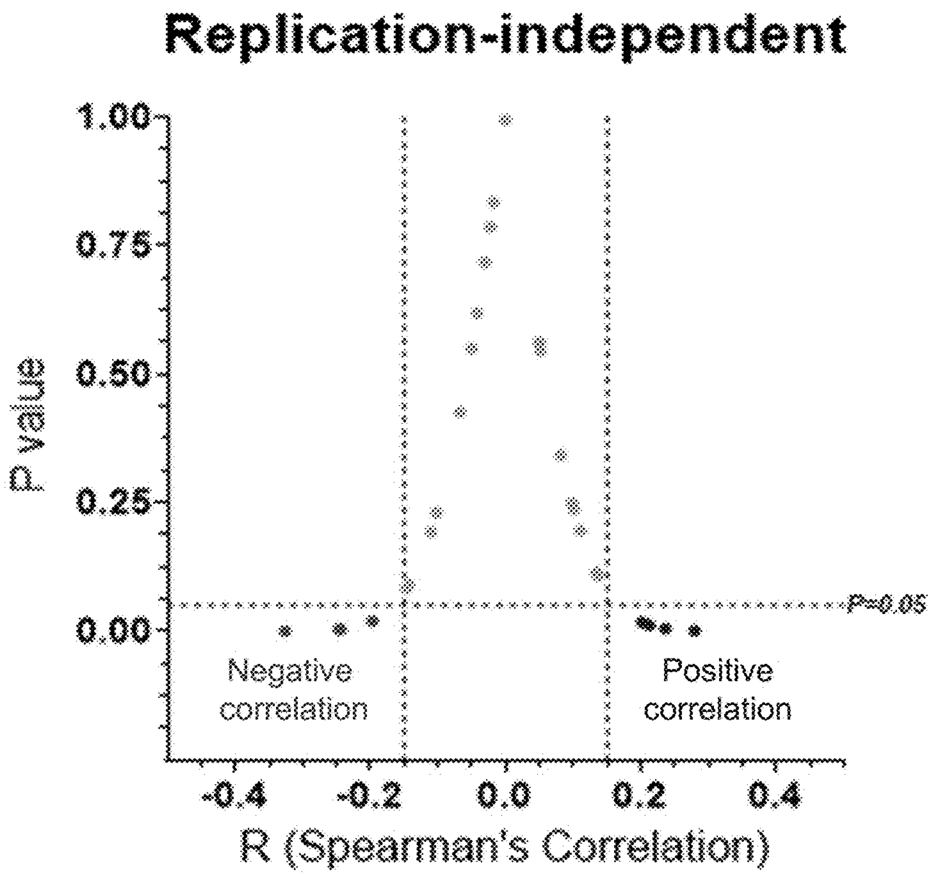
Figure 11:
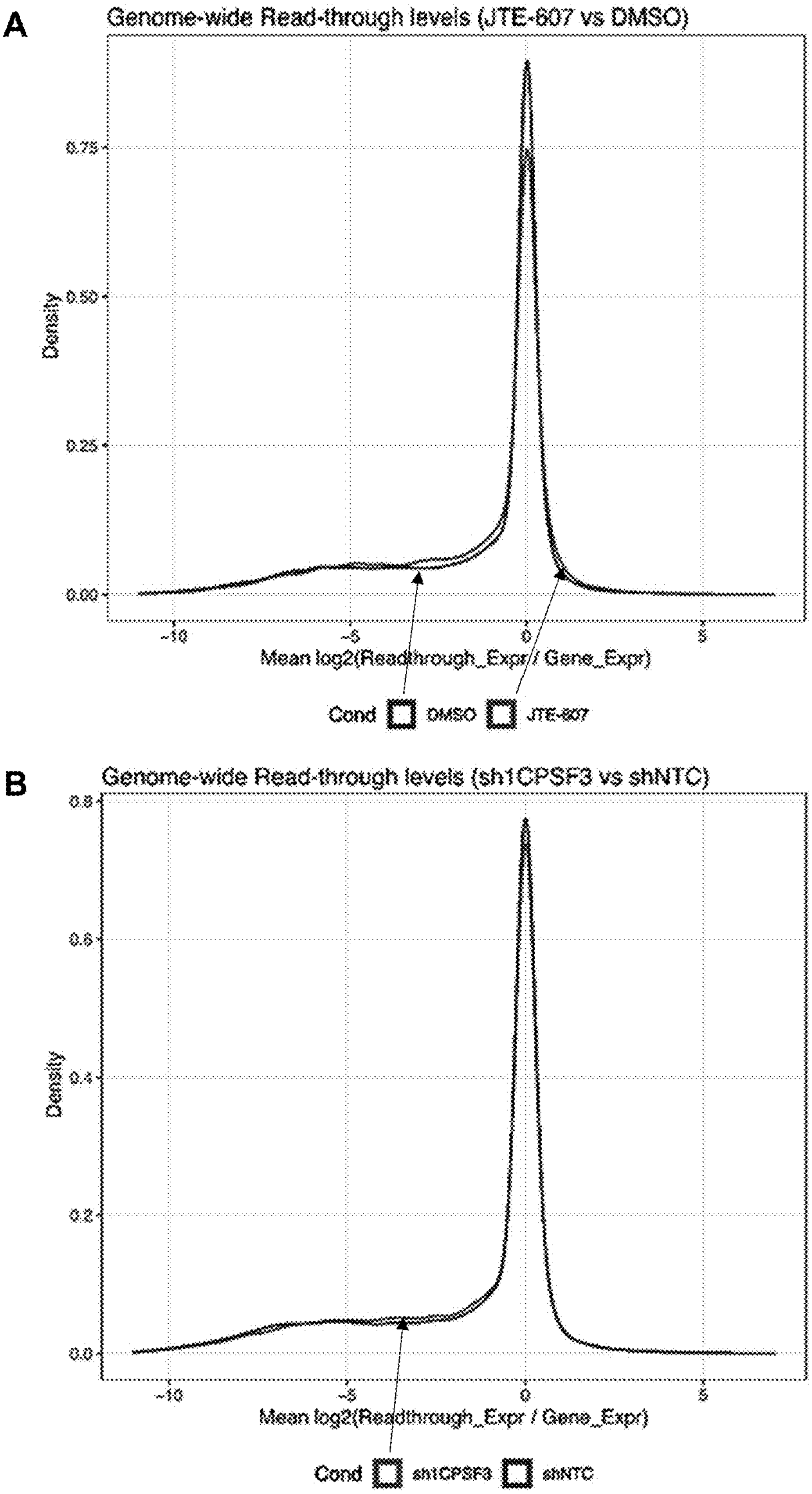
FIG. 11 shows CPSF3 disruption does not induce global transcriptional read-through, related to FIG. 4. (A) Density plot of global read-through events upon CPSF3 inhibition by JTE-607. (B) Density plot of global read-through events in CPSF3 knockdown cells. (C) Venn diagrams of short APA genes from TCGA-PAAD (Venkat et al.) data and Long APA genes upon CPSF3 knockdown and inhibition, respectively. Fisher's exact test was used to find the statistical significance. (D) Venn diagrams of differential APA genes (DAGs) and differentially expressed genes (DEGs) upon CPSF3 knockdown and inhibition. Fisher's exact test was used to find the statistical significance. (E) Density plot of histone-specific read-through events upon CPSF3 inhibition by JTE-607. A shift to the right indicates read-through differences between DMSO and JTE-607. P=0.004; Wilcox test. (F) Density plot of histone-specific read-through events in CPSF3 knockdown cells.
Figure 11:
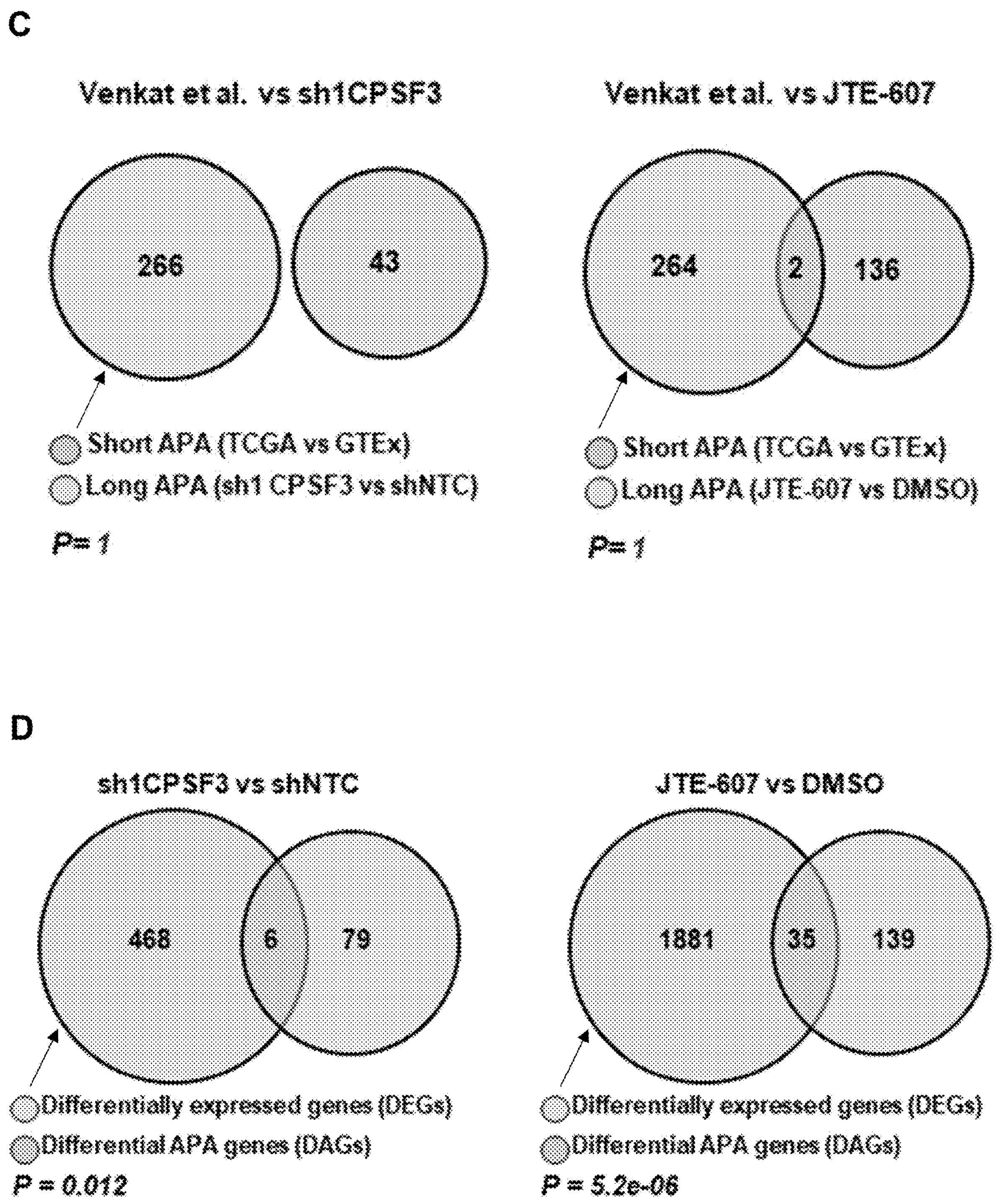
Figure 11:
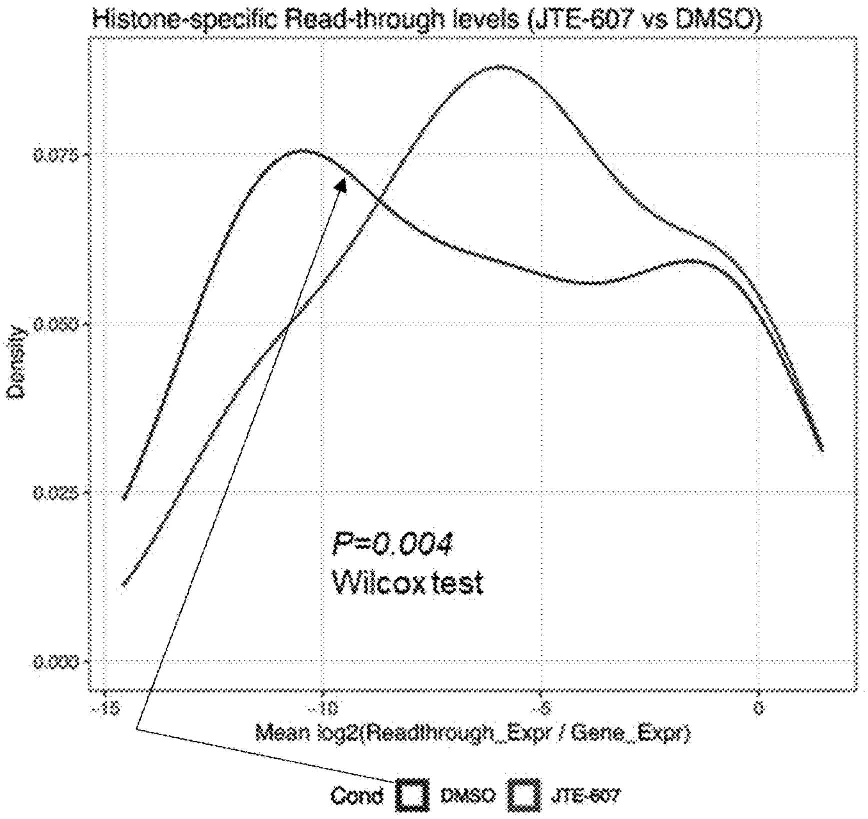
Figure 11:
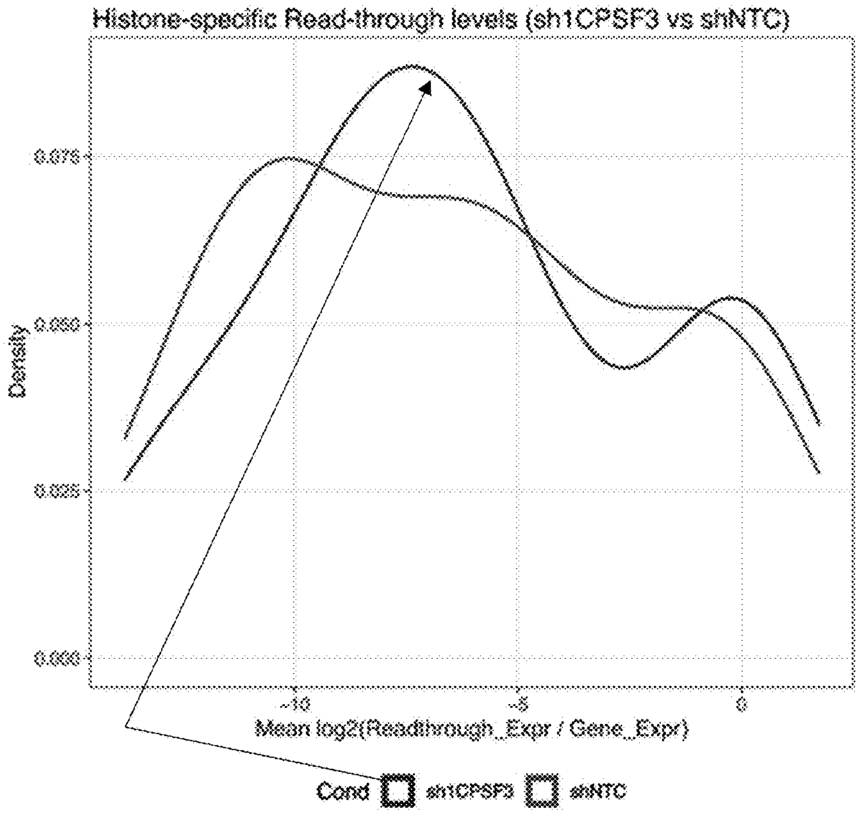

The mechanism by which CPSF3 disruption attenuates PDAC cell proliferation was examined. Therefore, it was asked whether CPSF3 disruption would reverse the APA patterns of those growth-promoting genes. However, neither CPSF3 knockdown nor inhibition altered the APA patterns of these genes (FIG. 11C). In fact, few genes were altered on both the APA and gene expression levels by either CPSF3 knockdown or inhibition (FIG. 11D). These data suggest that PDAC phenotype is mediated by other mechanisms in our cell line models. In addition to APA, CPSF3 controls histone mRNA processing as part of the HCC. Therefore, whether CPSF3-mediated disruption of histone processing affects PDAC cell phenotype was examined. Histone genes are classified into two classes: replication-independent (RI) and replication-dependent (RD) histones. RI histones are processed on their mRNA 3'end by APA and are polyadenylated. In contrast, RD histone mRNAs are processed by the HCC and are not polyadenylated. Importantly, RD histones are actively transcribed during DNA replication and therefore important for the proliferation of dividing cells. It was found that JTE-607 induced histone mRNA transcriptional read-through while CPSF3 knockdown had minimal effect (FIGS. 11E and 11F). In particular, histone read-through events were enriched for RD histones following JTE-607 treatment (FIG. 4A). CPSF3 knockdown, however, did not induce RD histone read-through events (FIG. 4B). These results again highlight the differences between knockdown and inhibition of CPSF3, and suggest that JTE-607-dependent read-through is preferential to RD histones.

Figure 12:
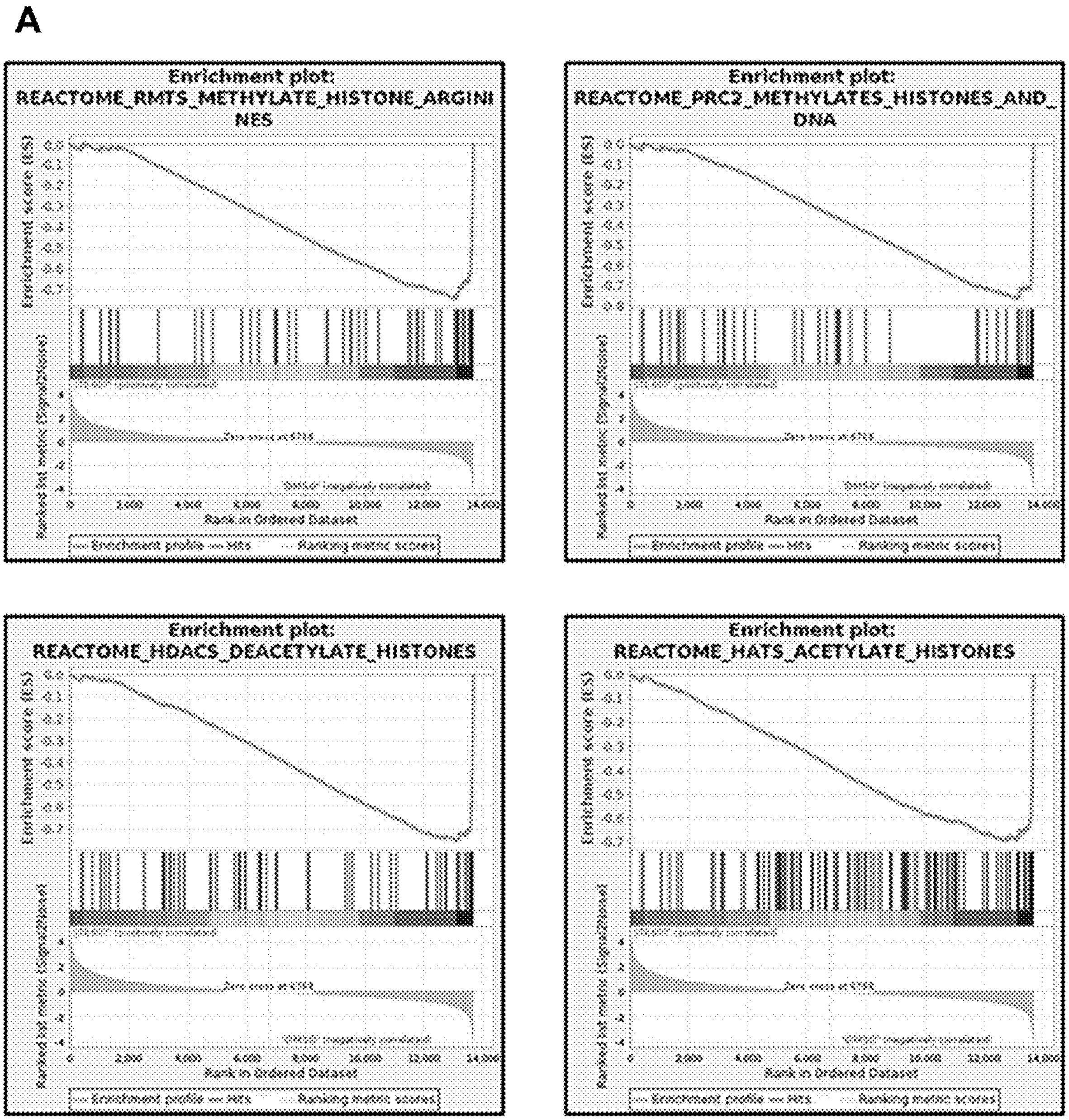
FIG. 12 High levels of RD histones are associated with poor prognosis in PDAC patients, related to FIG. 4. (A) Gene set enrichment analysis (GSEA) from RNA-seq data upon JTE-607 treatment. (B) Heatmap of differentially expressed genes in Panc1 cells upon CPSF3 knockdown. Expression is plotted as normalized expression values. (C) Venn diagrams of differentially expressed genes upon CPSF3 knockdown and inhibition. Fisher's exact test was used to find the statistical significance. Only 119 genes are differentially expressed in both conditions. (D, E) Survival analyses of RD histone signature (50 genes) from TCGA-PAAD dataset. Signature genes were uploaded to GEPIA2 to assess disease free (D) and overall survival (E) based on median.
Figure 12:
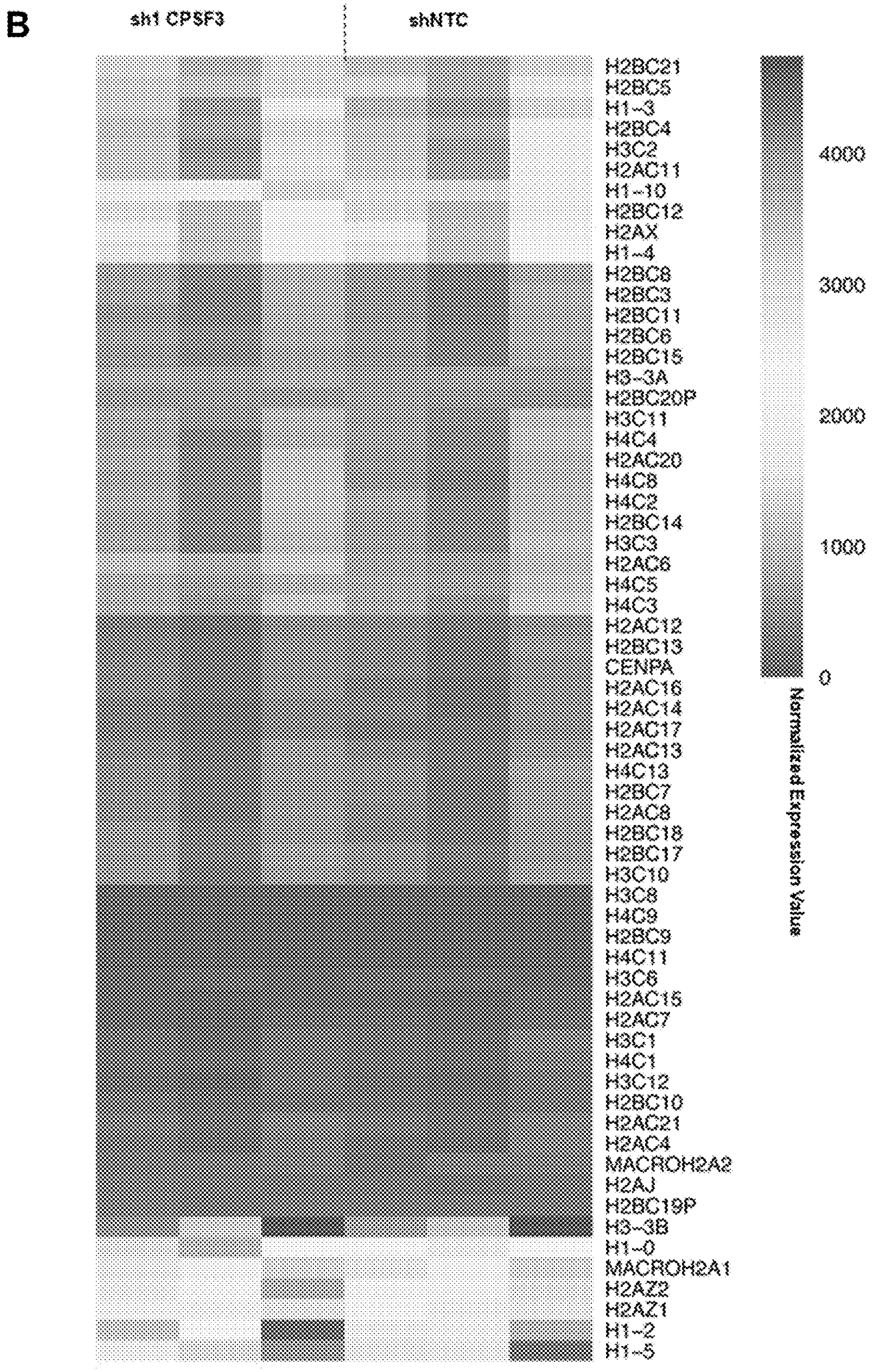
Figure 12:
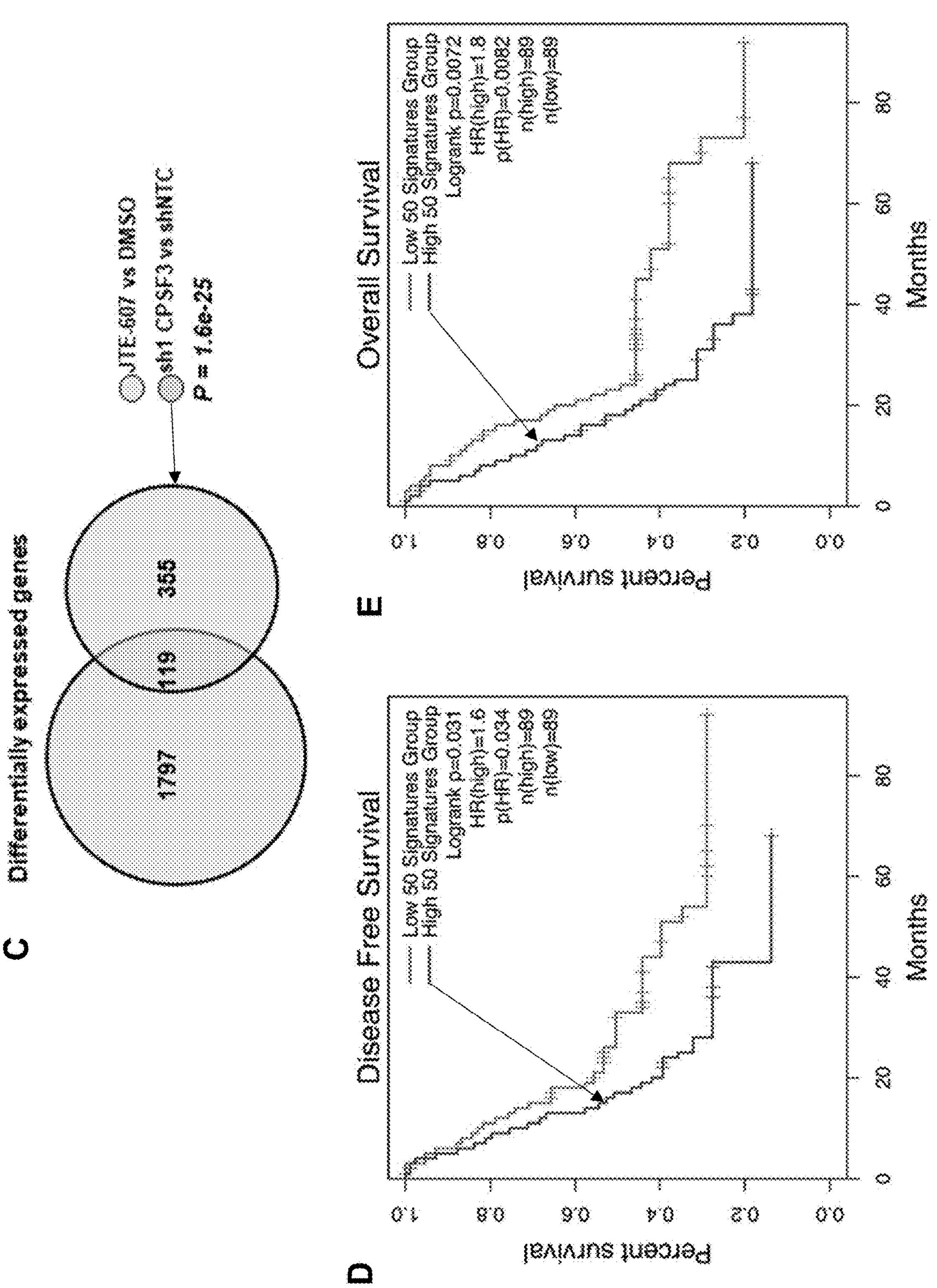

As JTE-607 has been previously administered to patients with no cytotoxic effects, we wanted to determine the mechanism underlying the ability of JTE-607 to attenuate PDAC cell proliferation. Differential gene expression analysis was performed and it was found that numerous histone genes were significantly downregulated upon JTE-607 treatment (FIG. 4C, Blue-labeled genes). Gene set enrichment analysis (GSEA) also demonstrated a dysregulation in many histone-related pathways, including histone methylation, acetylation and deacetylation (FIG. 12A). However, CPSF3 knockdown did not affect histone gene expression in our cell line model (FIG. 12B). In fact, the discrepancies between CPSF3 knockdown and inhibition extend to the overall differential gene expression with only 119 genes being differentially expressed in both conditions (FIG. 12C). The majority of the differentially expressed histones upon CPSF3 inhibition with JTE-607 were RD histones (41 genes). It was validated that JTE-607-induced decrease in RD histones in MiaPaCa2 cells (FIG. 4D). In contrast, RI histones were not downregulated by JTE-607 (FIG. 4E). Therefore, JTE-607 treatment decreases the expression of RD histones. Next, it was sought to determine if there was a correlation between CPSF3 and histone gene expression levels in PDAC patients. The Spearman's correlation for CPSF3 and 98 histone genes from the CPTAC database (Spearman=−0.15>R>0.15, P<0.05) (FIG. 4F) were calculated. In accordance with the experimental findings, there were significantly more positive correlations (43 genes) between CPSF3 and histone gene expression than negative correlations (3 genes) among RD histones (FIG. 4G). In contrast, there were few significant correlations between CPSF3 and RI histones (only 8 genes), and those significant alterations were equally positive and negative (FIG. 4H). Finally, it was sought to determine if RD histone expression predicts patient outcomes. A signature by selecting 50 RD histones and assessed PDAC patient survival based on gene expression was generated. It was found that high levels of RD histones are associated with worse disease-progression (p=0.031, Hazard Ratio=1.6) and poor overall survival (p=0.0072, Hazard Ratio=1.8) in PDAC patients (FIGS. 12D and 12E). Collectively, these results indicate that JTE-607 preferentially downregulates RD histones.

Figure 5:
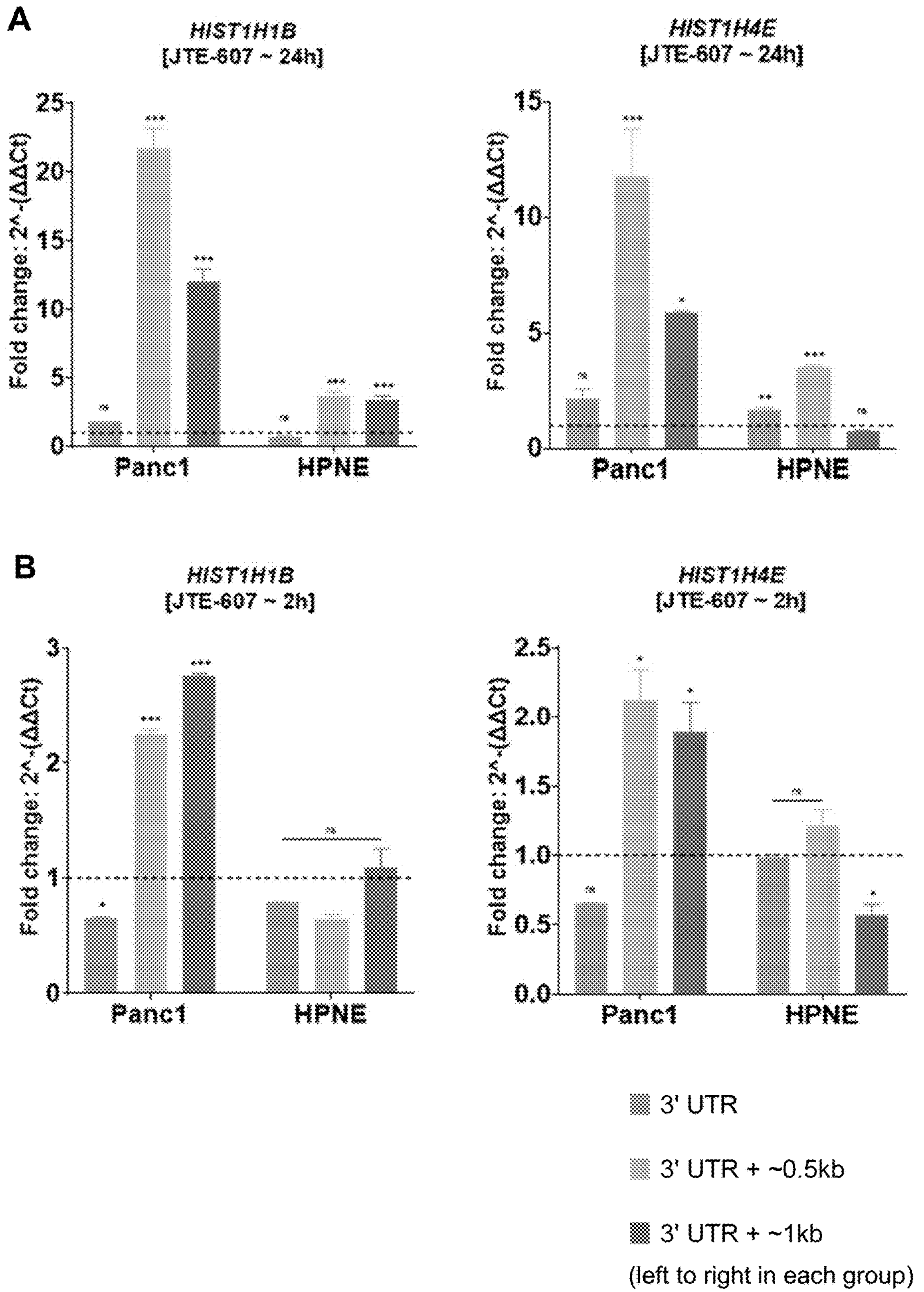
FIG. 5 shows JTE-607 induces replication-dependent histone transcription read-through. (A, B) Quantification of replication-dependent histone read-through in Panc1 and HPNE cells after 24 h (A) and 2 h (B) of JTE-607 treatment by RT-qPCR. Data were normalized to DMSO controls (Dashed horizontal line). *, P<0.05; , P<0.01; *, P<0.001; 2way ANOVA with Sidak's multiple comparisons test. (C, D) Quantification of replication-independent histone read-through in Panc1 and HPNE cells after 24 h (C) and 2 h (D) of JTE-607 treatment by RT-qPCR. Data were normalized to DMSO controls (Dashed horizontal line). *, P<0.05; , P<0.01; *, P<0.001; 2way ANOVA with Sidak's multiple comparisons test. (E, F) Quantification of histone read-through in Panc1 upon long term knockdown by shRNA (E) and short term knockdown by siRNA (F) by RT-qPCR. Data were normalized to non-targeting controls (Dashed horizontal line). *, P<0.05; **, P<0.01; 2way ANOVA with Sidak's multiple comparisons test.
Figure 5:
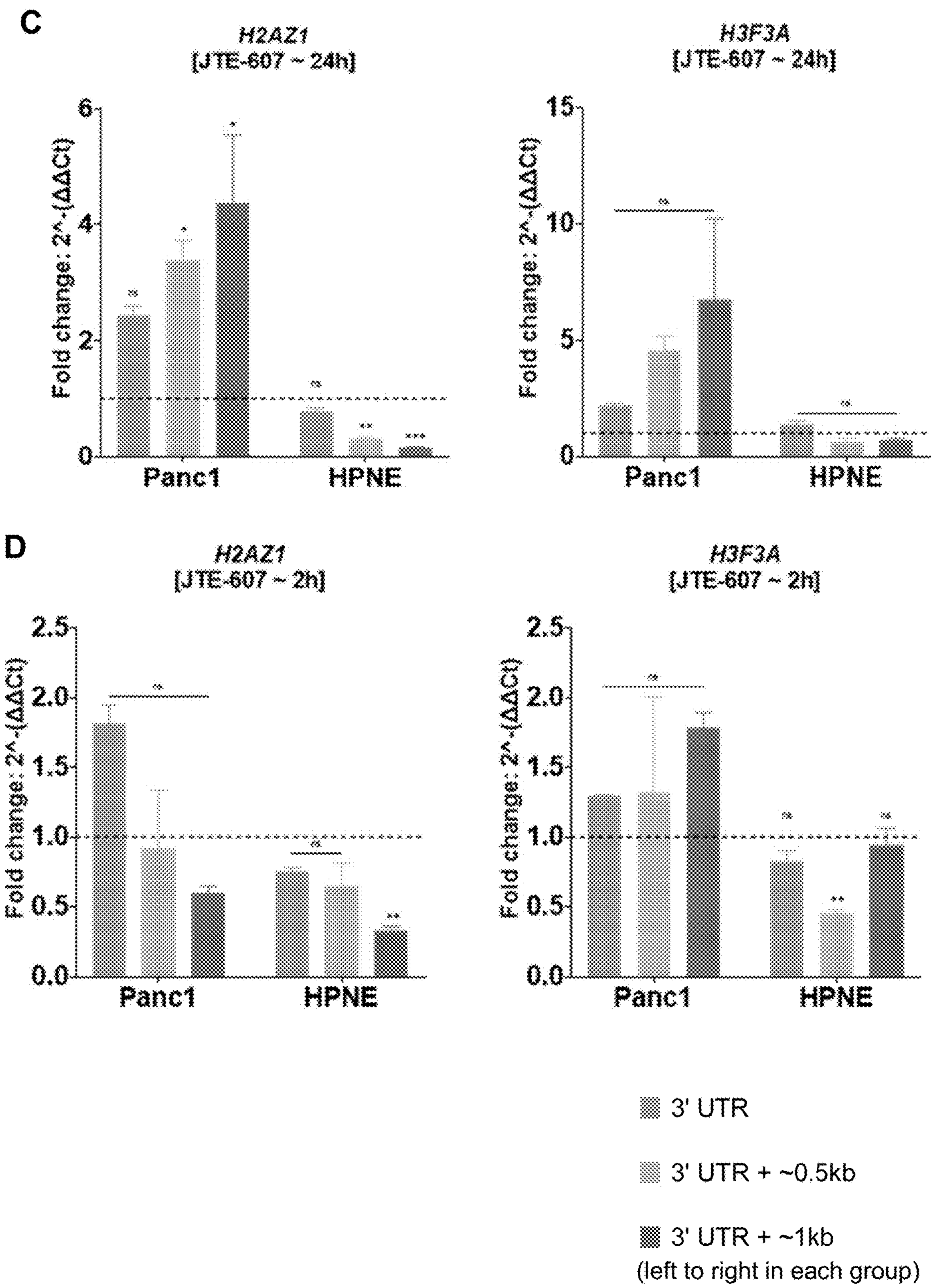
Figure 5:
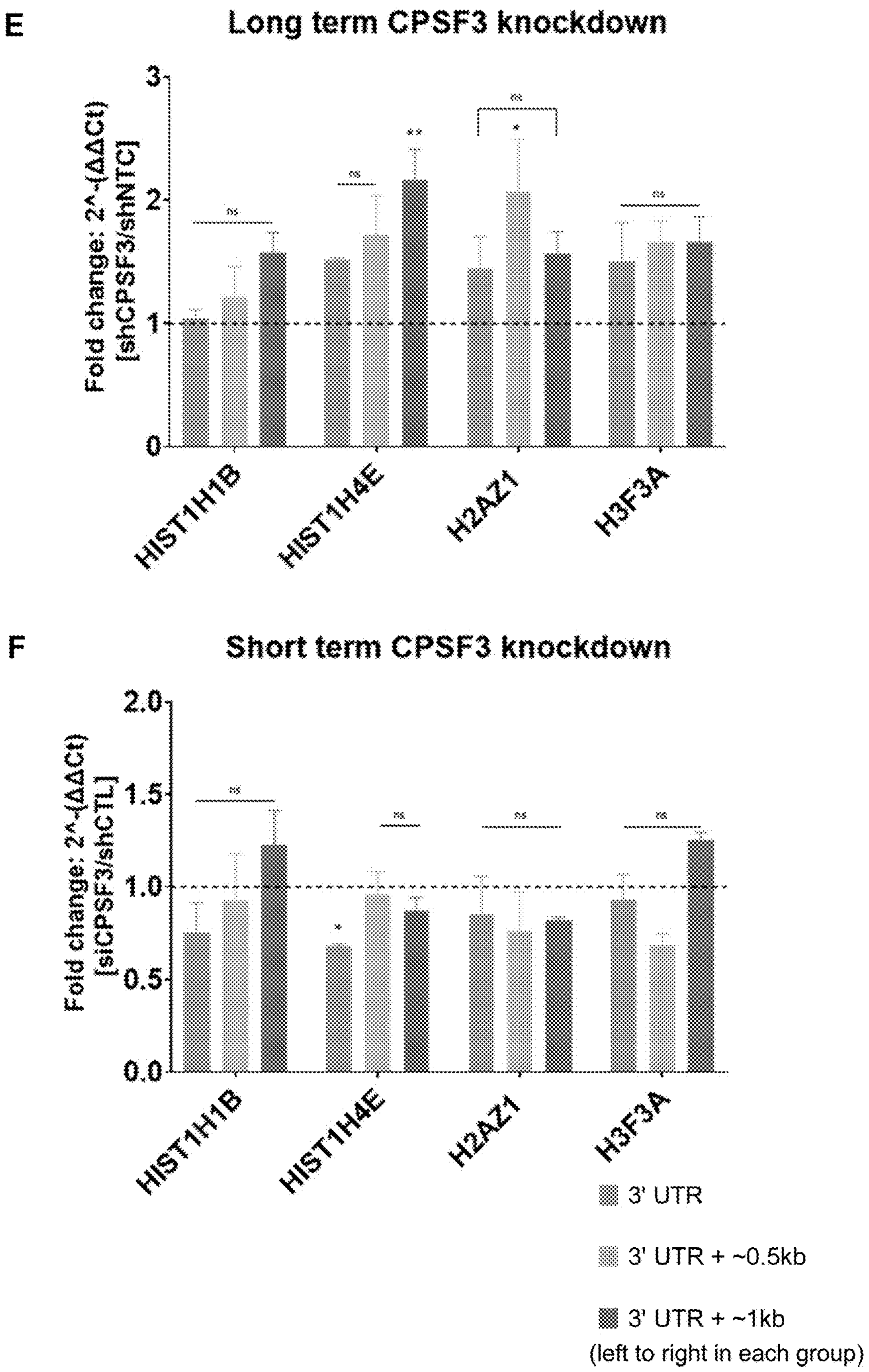
Figure 13:
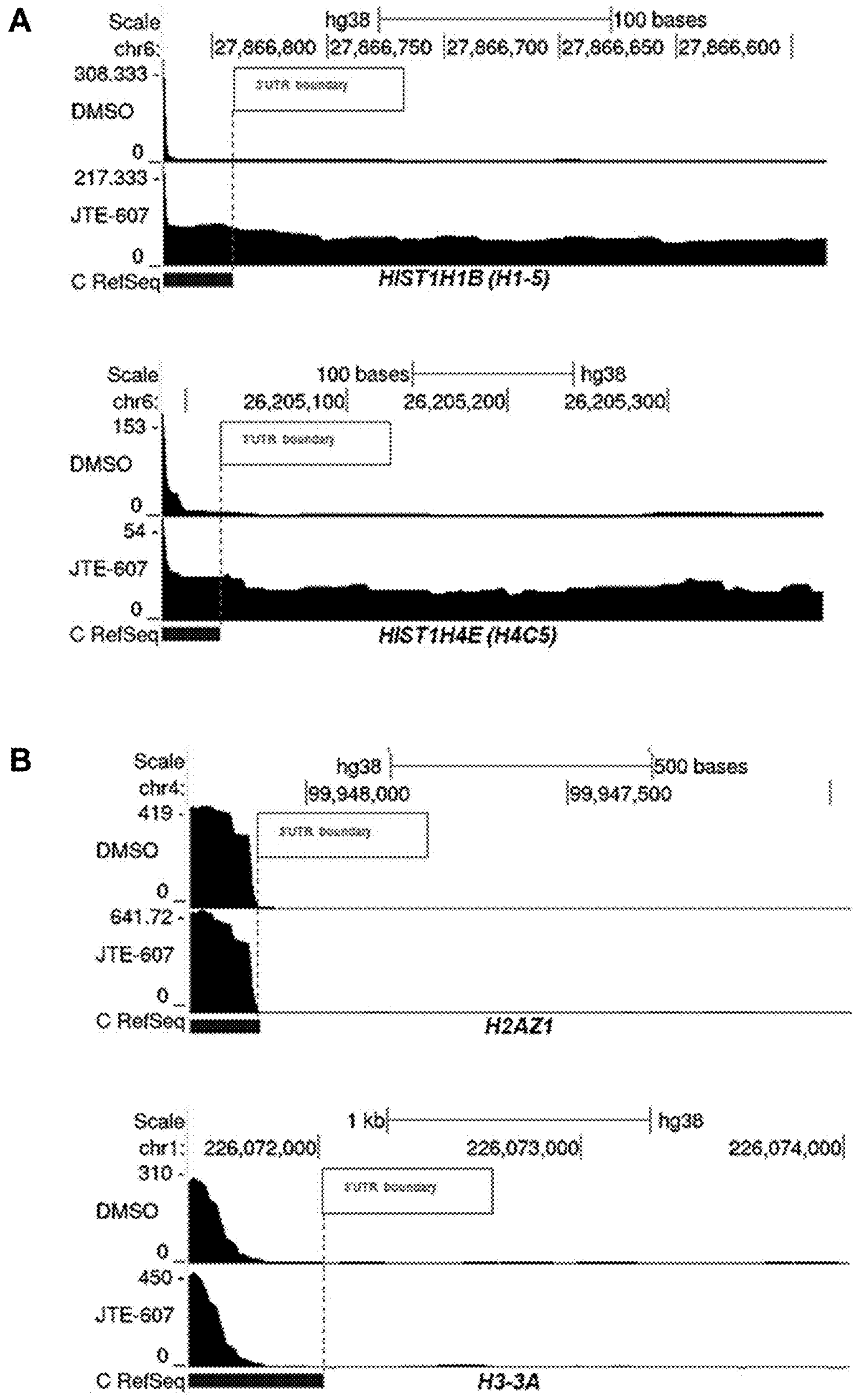
FIG. 13 shows JTE-607 decreases histone protein levels, related to FIG. 5. (A) UCSC genome browser-generated density plots of two representative replication-dependent histones highlighting the differences of read coverage beyond the 3'UTR boundaries upon JTE-607 treatment. (B) UC SC genome browser-generated density plots of two representative replication-independent histones highlighting the differences of read coverage beyond the 3'UTR boundaries upon JTE-607 treatment. (C) Schematic showing primer design for read-through quantification by RT-qPCR. (D) Quantitative RT-qPCR showing CPSF3 mRNA expression levels in Panc1 cells upon CPSF3 transient knockdown by siRNA. Data are shown as mean±SEM.*, P<0.05, unpaired t test. (E, F) Western blot of histone protein levels in Panc1 cells upon CPSF3 inhibition (E) and knockdown (F). (G, H) Venn diagrams showing the overlap between hi stone transcription factors and significant APA-altered genes (G) or differentially expressed genes (H) upon JTE-607 treatment.
Figure 13:
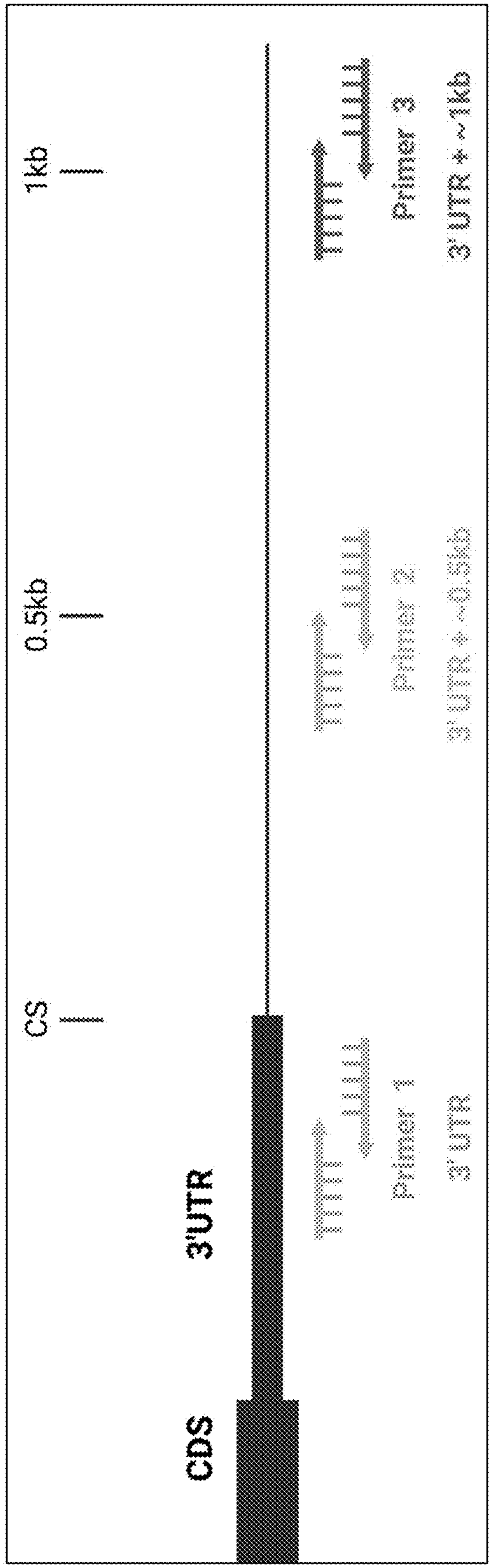
Figure 13:
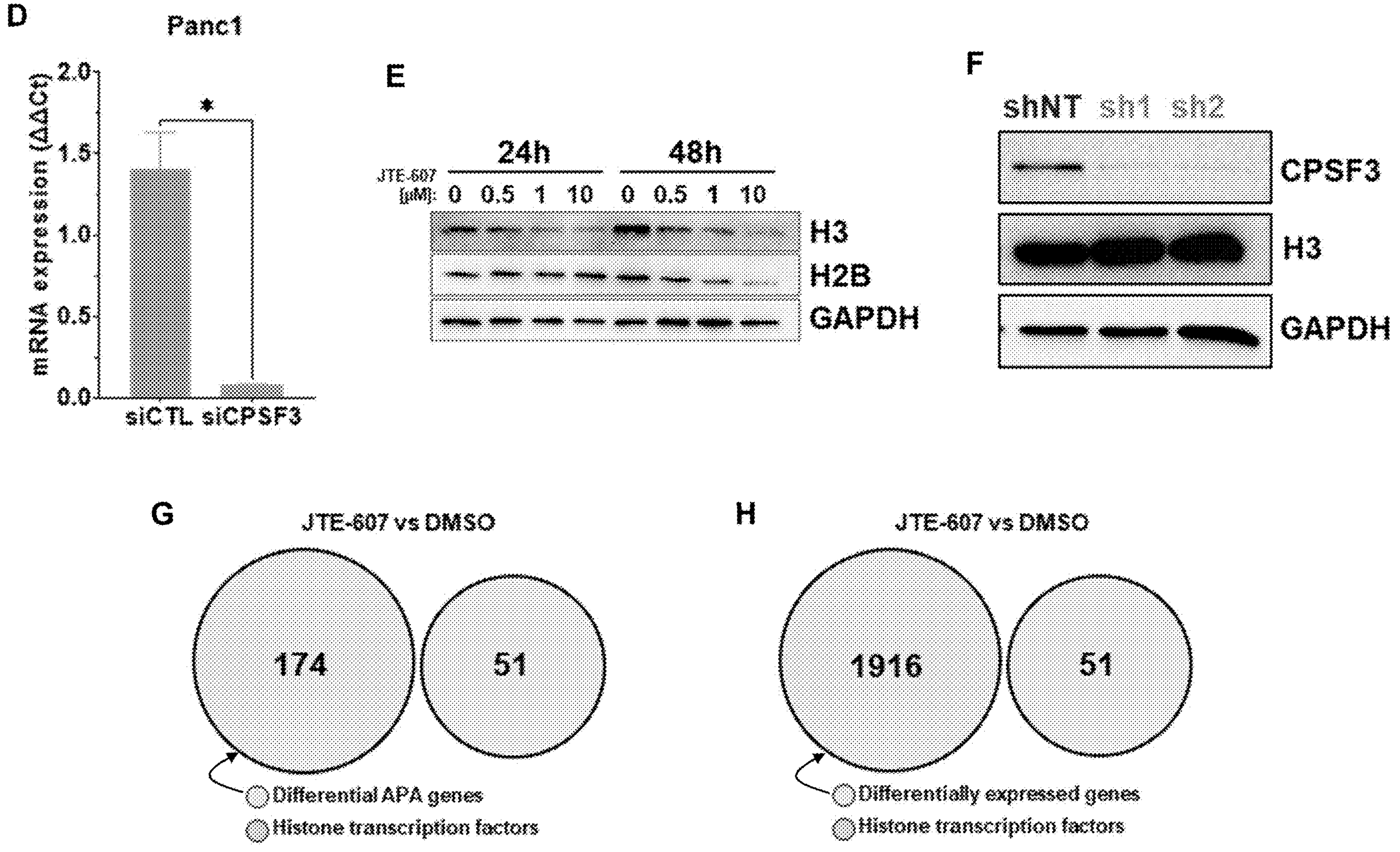

JTE-607 induces RD-histone read-through preferentially in PDAC cells. While CPSF3 knockdown studies have demonstrated a role for CPSF3 in histone processing, the effect of inhibiting CPSF3 activity on histone mRNA processing has never been biologically determined. It was sought to validate this transcriptional read-through phenomena experimentally by RT-qPCR. Two RD- and two RI-histones that show differences beyond their 3' end boundaries were picked for experimental validation (FIGS. 13A and 13B). PCR primers were designed to amplify different regions within and beyond the boundaries of the 3'-UTR (FIG. 13C). It was found that 24 h JTE-607 treatment significantly induced transcriptional read-through (up to ~20-fold change) of RD histones in Panc1 cells (FIG. 5A). However, the effect of JTE-607 on transcriptional read-through in HPNE cells was minimal (FIG. 5A). In fact, 2-hours of JTE-607 treatment were enough to induce transcriptional read-through levels in Panc1 cells comparable to those in HPNE cells after 24-hours of treatment (FIGS. 5A and 5B). Importantly, JTE-607 did not induce transcriptional read-through of RI histones at early or late time points in both Panc1 and HPNE cells (FIGS. 5C and 5D). As CPSF3 knockdown did not affect histone gene levels, it was aimed to further delineate the differences between knockdown and inhibition in inducing transcriptional read-through. It was found that long term knockdown of CPSF3 by shRNA did not induce transcriptional read-through in both RD and RI histones (FIG. 5E). Because stable long-term knockdown can force cells to adapt, it was asked whether short-term knockdown of CPSF3 can recapitulate JTE-607 effect on transcriptional read-through. CPSF3 was transiently silenced using siRNA (FIG. 13D) and found that CPSF3-silencing did not induce transcriptional read-through in both RD and RI histones (FIG. 5F). Improperly processed histone mRNAs fail to be exported into the cytoplasm for translation, leading to decreased protein levels. Therefore, RD histone protein levels upon JTE-607 treatment were examined and found that JTE-607 reduced both H3 and H2B protein levels in a dose- and time-dependent fashion (FIG. 13E). In contrast, CPSF3 knockdown did not reduce H3 protein levels (FIG. 13F). Next, it was determined whether histone dysregulation might be transcriptionally mediated by dysregulation of transcription factors at the levels of APA or gene expression. MotifMap, an integrative genome-wide map of regulatory motif sites, was used to find putative transcription factors regulating expression of RD histones. 51 transcription factors that have strong binding sites (1000 bp upstream of transcription start site; FDR<0.05) within RD histone promoters (Table S3 (attached as a Large Table)) were found. However, these histone transcription factors are neither APA altered nor differentially expressed upon JTE-607 treatment (FIGS. 13G and 13H). Taken together, these findings indicate that JTE-607 decreases RD histone expression by promoting transcriptional read-through.

Figure 6:
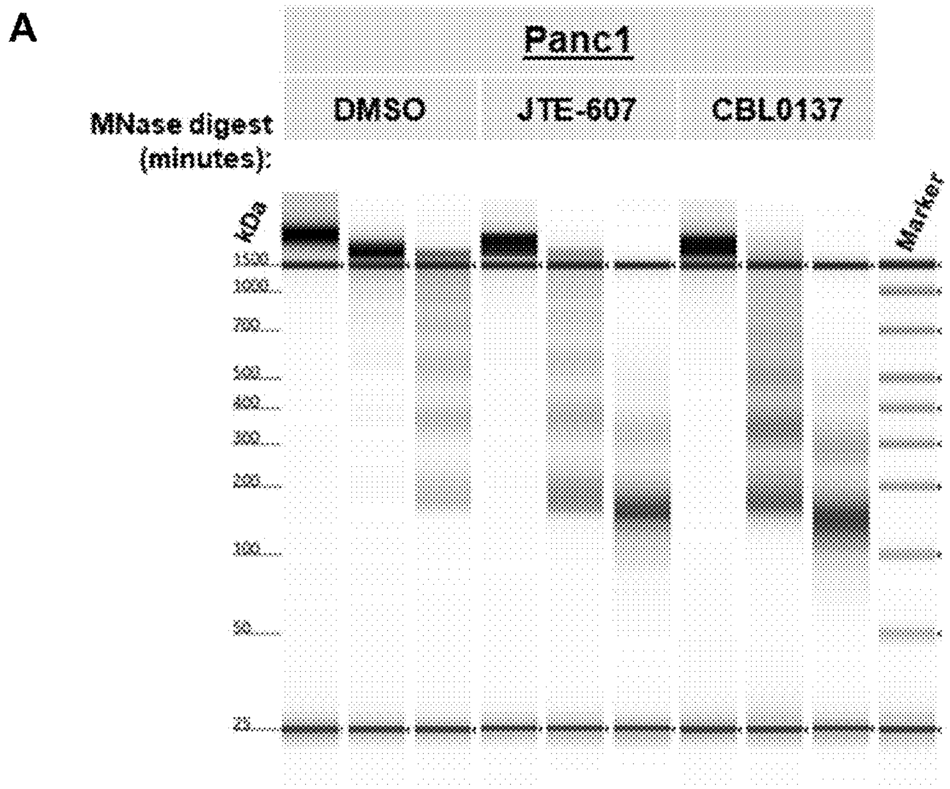
FIG. 6 shows JTE-607 induces chromatin instability selectively in PDAC cells. (A) Micrococcal Nuclease assay of Panc1 cells treated with JTE-607 or CBL0137. (B) Micrococcal Nuclease assay of non-transformed HPNE cells treated with the CPSF3 inhibitor JTE-607 or CBL0137. (C) GFP+ HeLa-TI cells following JTE-607 or CBL0137 treatment. (D) Fold change of GFP+ HeLa-TI from (C). *, P<0.0001; 2way ANOVA with Tukey's multiple comparisons test. (E) Flow cytometry analysis of GFP+ HeLa-TI cells following JTE-607 or CBL0137 treatment. Fold change is shown as mean±SEM of two independent experiments. , P<0.01, ***, P<0.0001, Ordinary one-way ANOVA with Tukey's multiple comparisons test.
Figure 6:
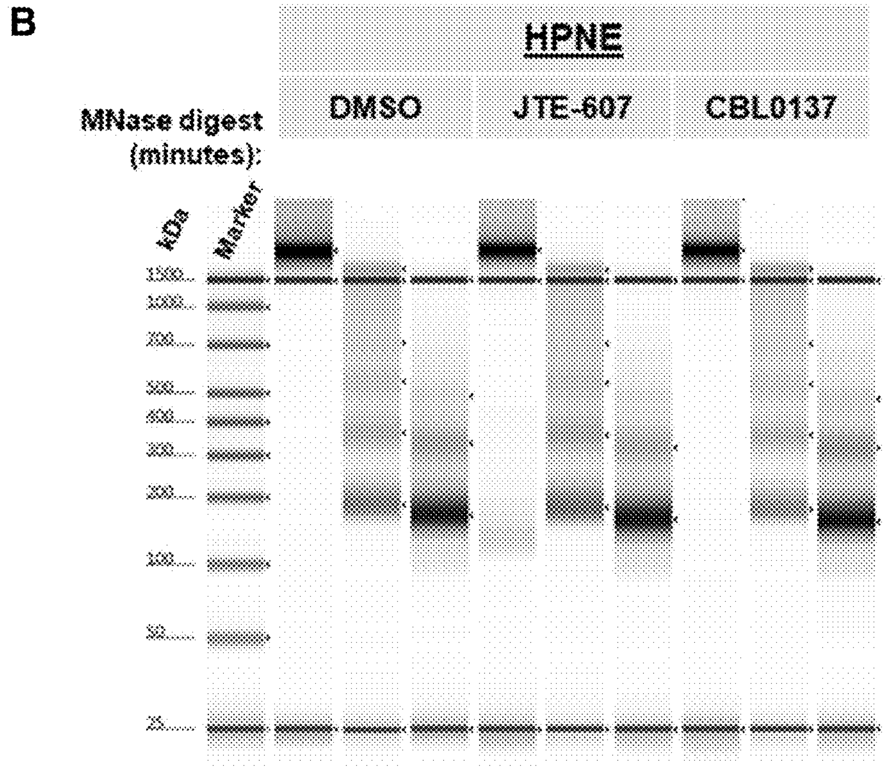
Figure 6:
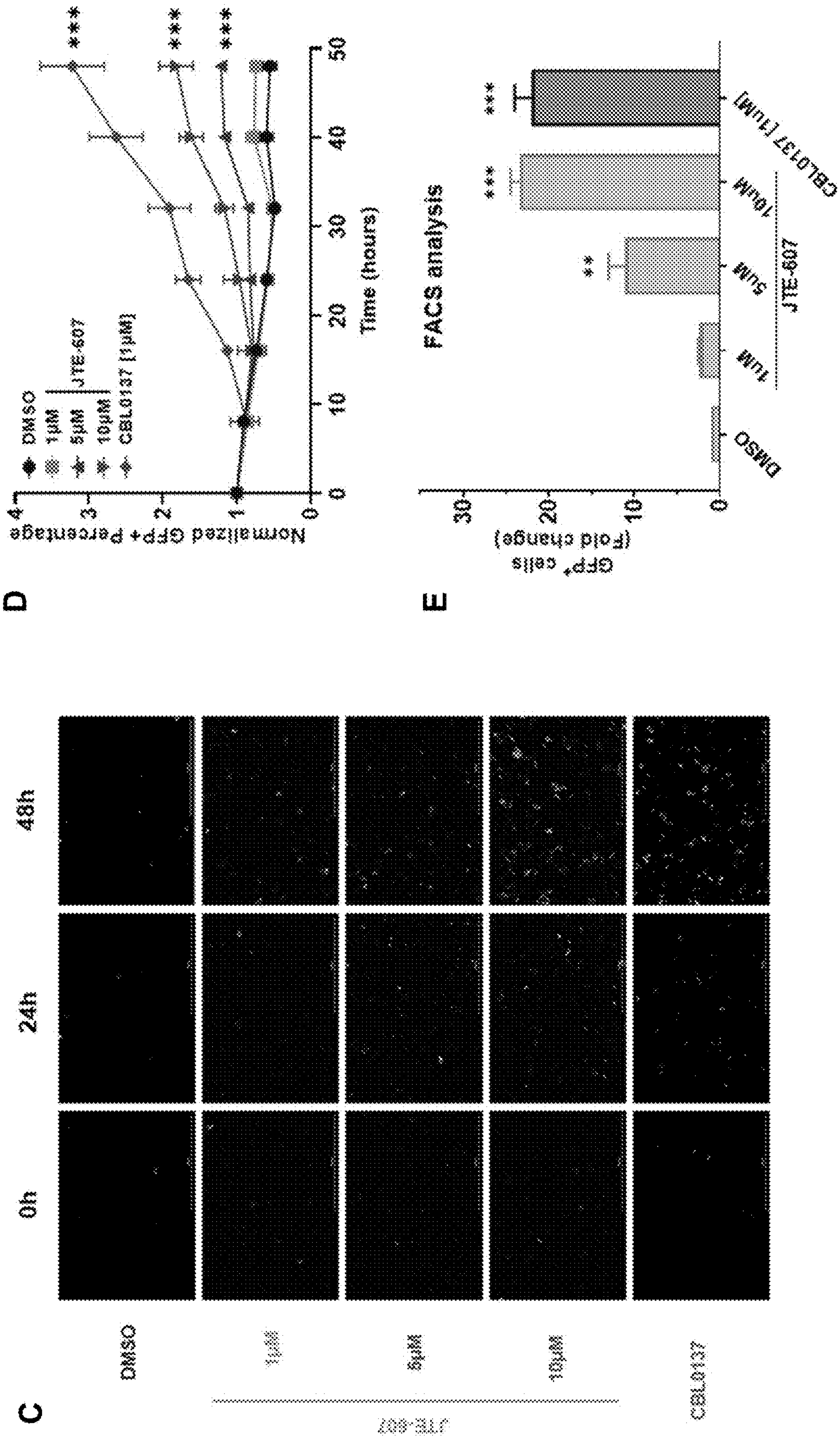
Figure 14:
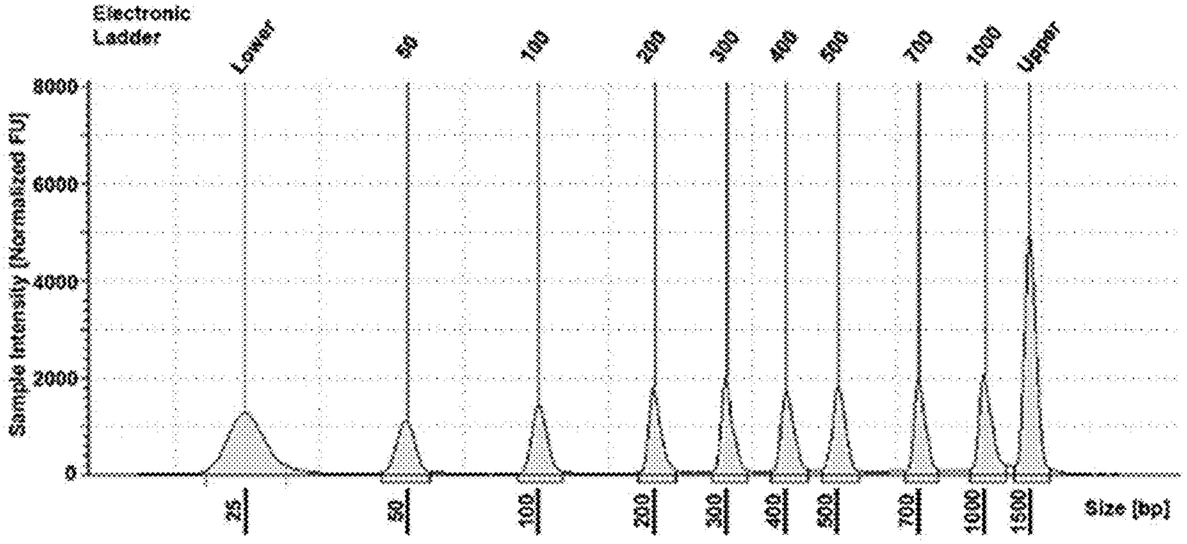
FIG. 14 shows JTE-607 increases genomic DNA digestion in Panc1 cells, related to FIG. 6. (A) Gene ontology analysis of significantly downregulated genes upon JTE-607 treatment. Enrichr was used to perform the analysis. (B-E) Nucleosome intensity plots of Panc1 cells upon JTE-607 treatment. Lower base pair sizes indicate more digestion at that specific size. The intensity of digestion is represented by the Y-axis. (F-I) Nucleosome intensity plots of HPNE cells upon JTE-607 treatment. Lower base pair sizes indicate more digestion at that specific size. The intensity of digestion is represented by the Y-axis.
Figure 14:
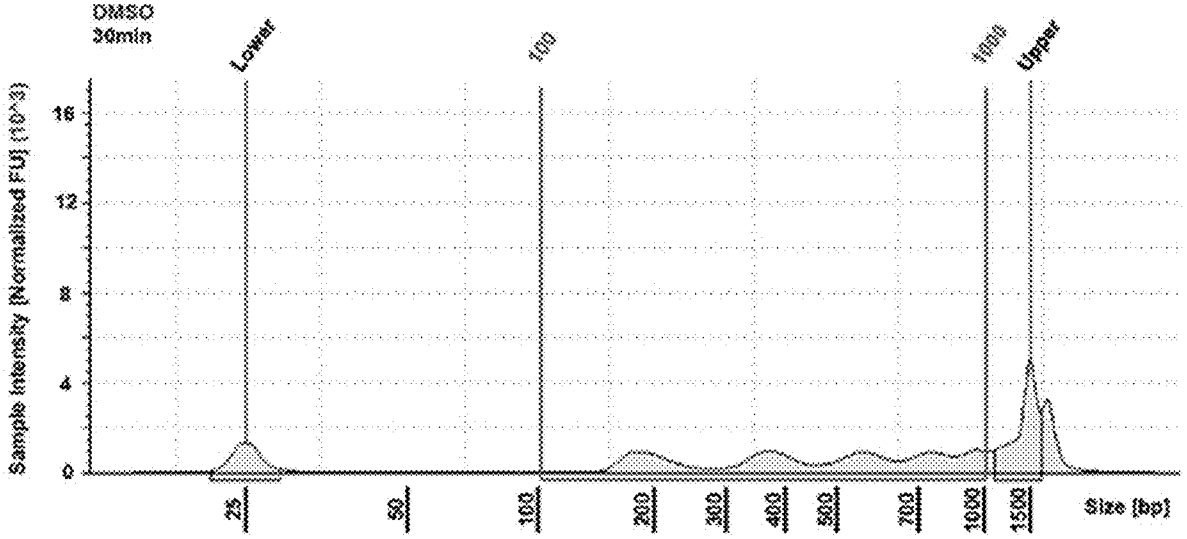
Figure 14:
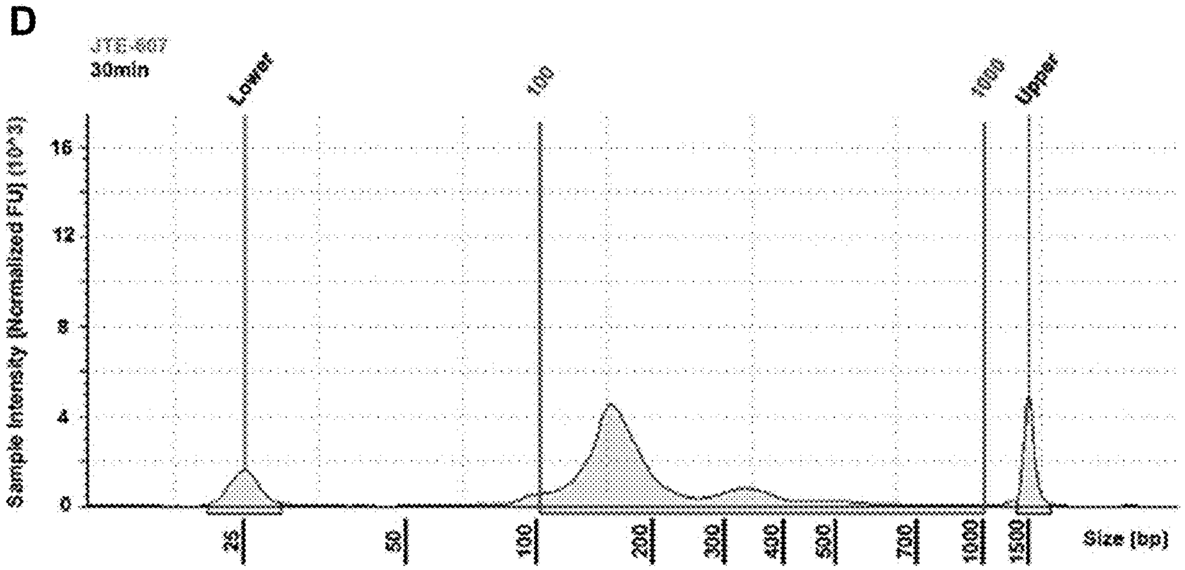
Figure 14:
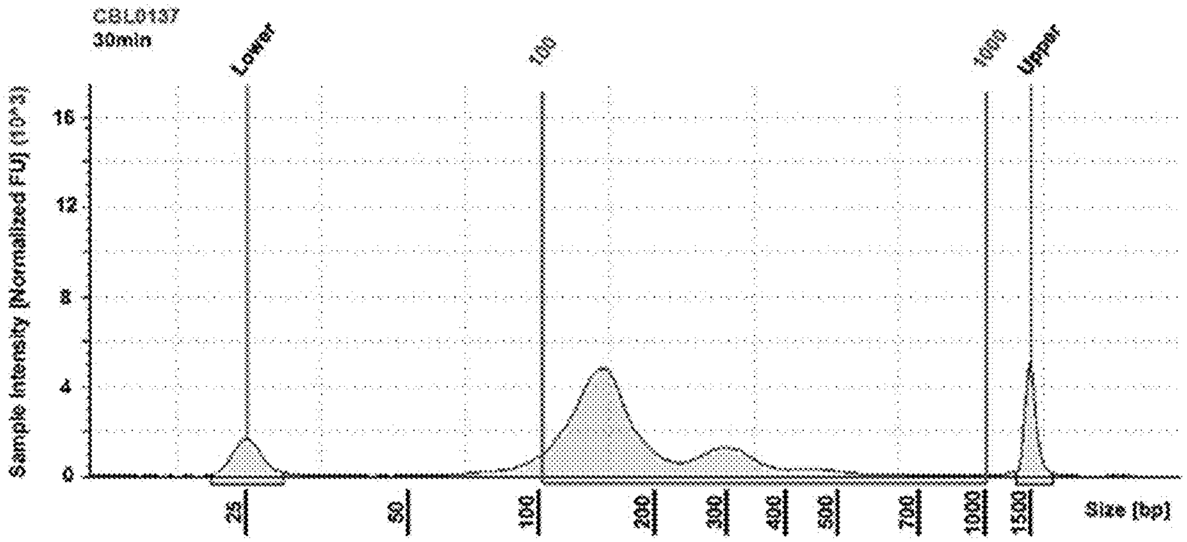
Figure 14:
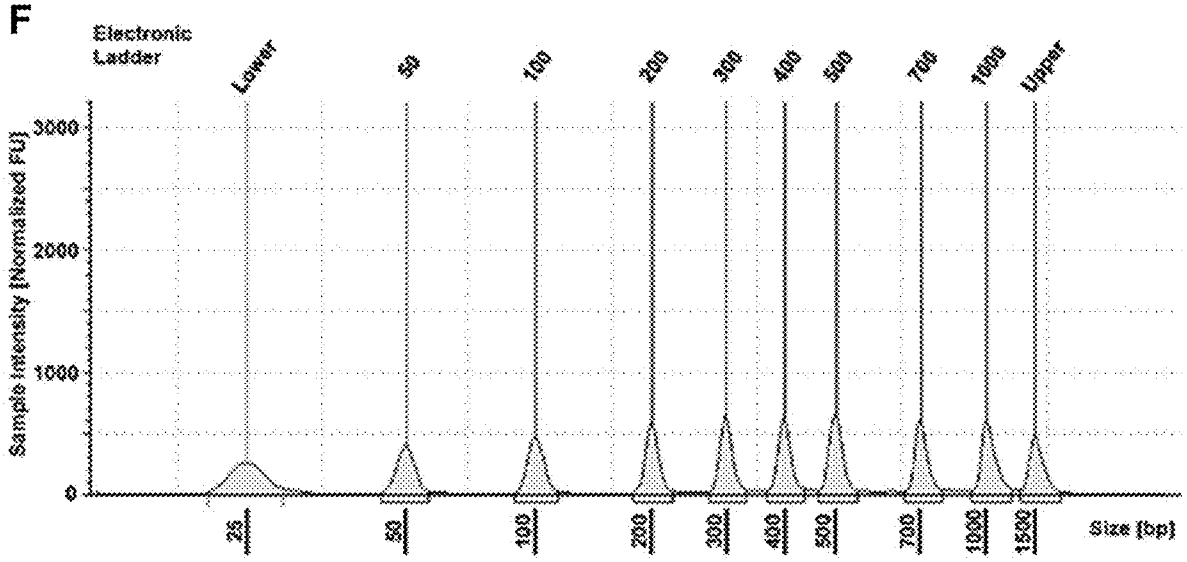
Figure 14:
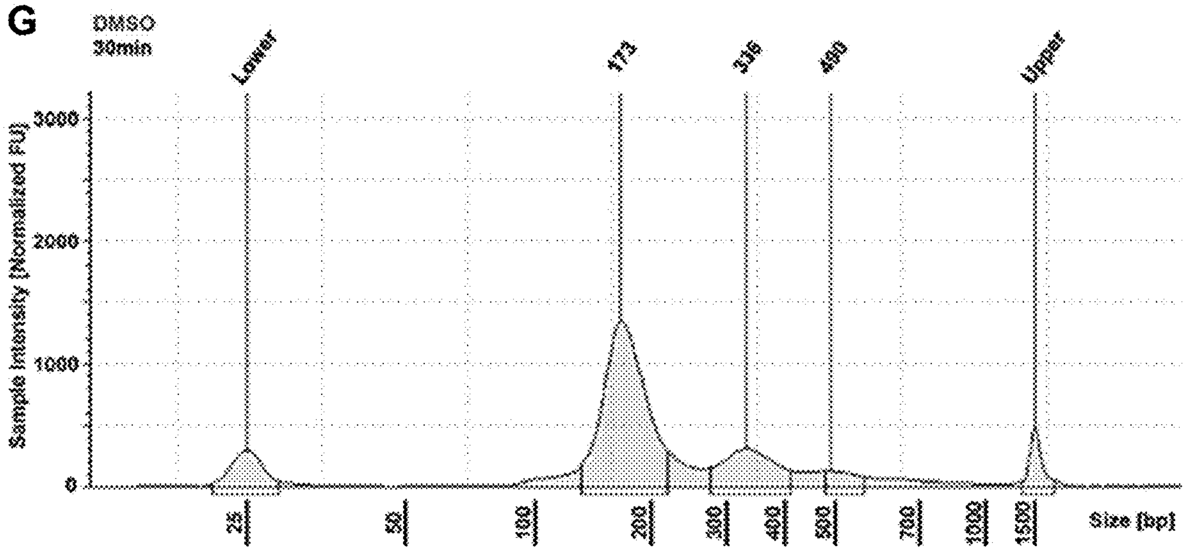
Figure 14:
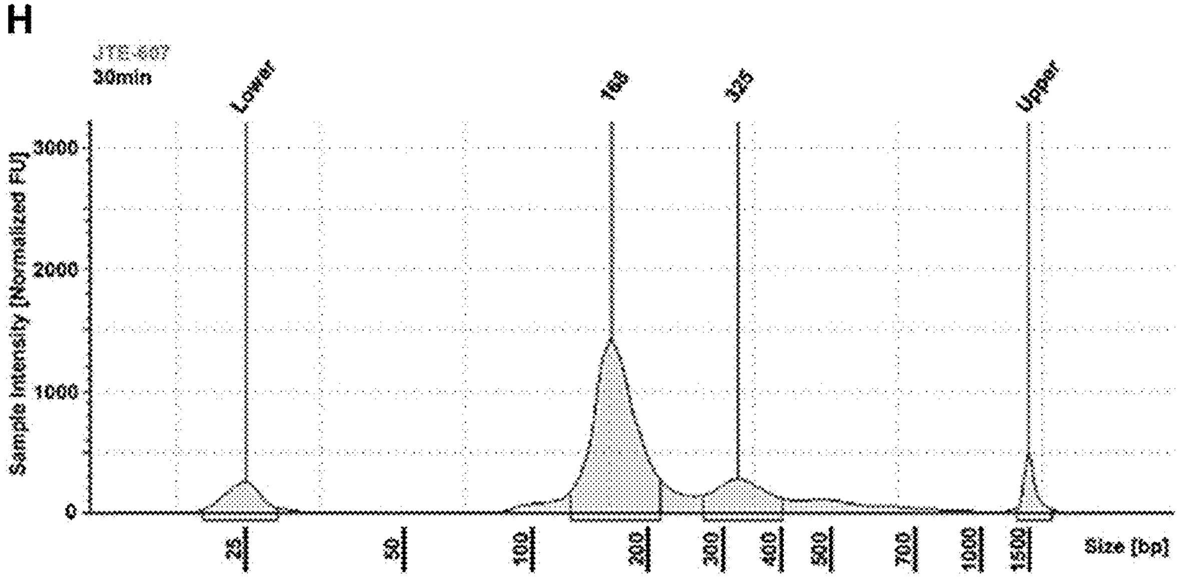
Figure 14:
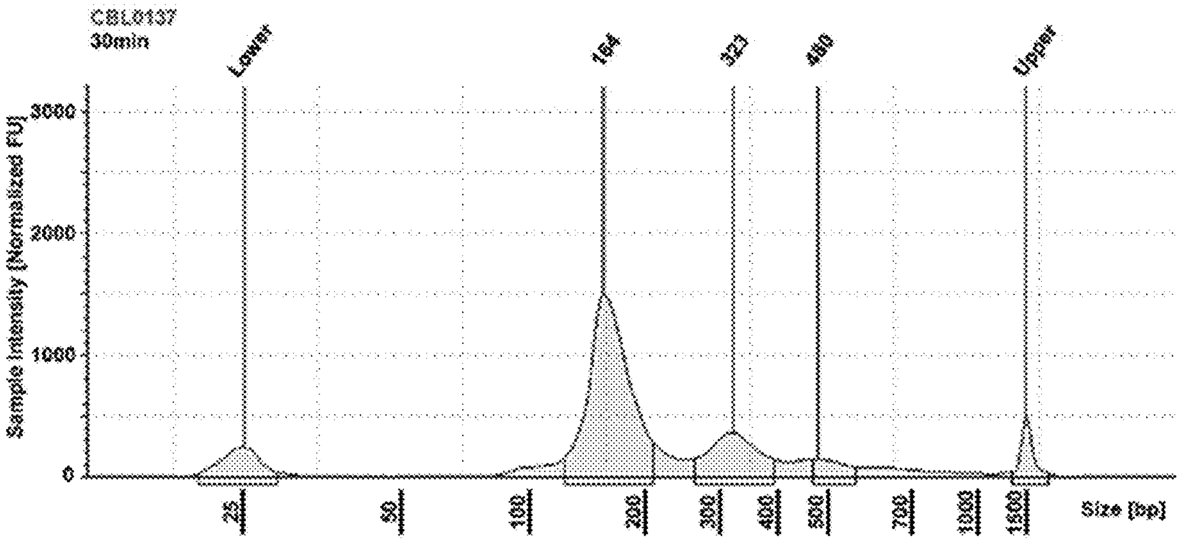
Figure 15:
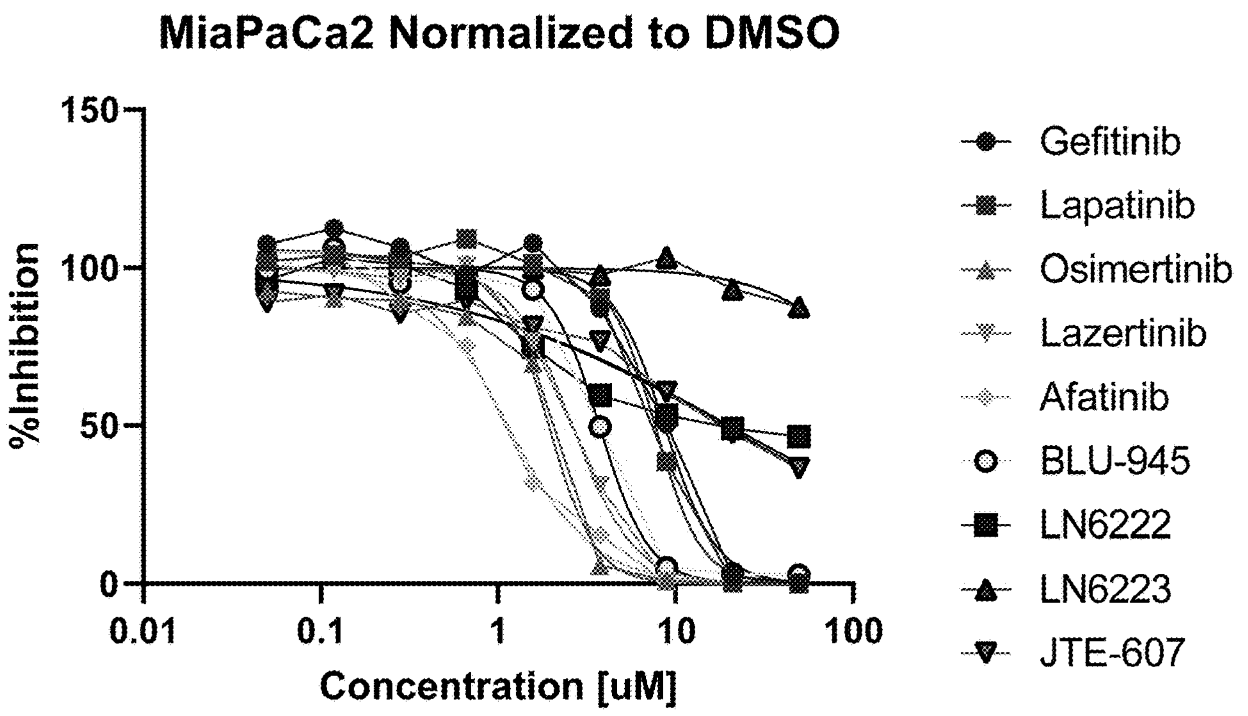
FIG. 15 shows MiaPaCa2 PDAC cells are sensitive to JTE-607 and epidermal growth factor receptor (EGFR) inhibitors. IC50 of JTE-607 and EGFR inhibitors on MiaPaCa2 cells after 72-hours of treatment.
Figure 16:
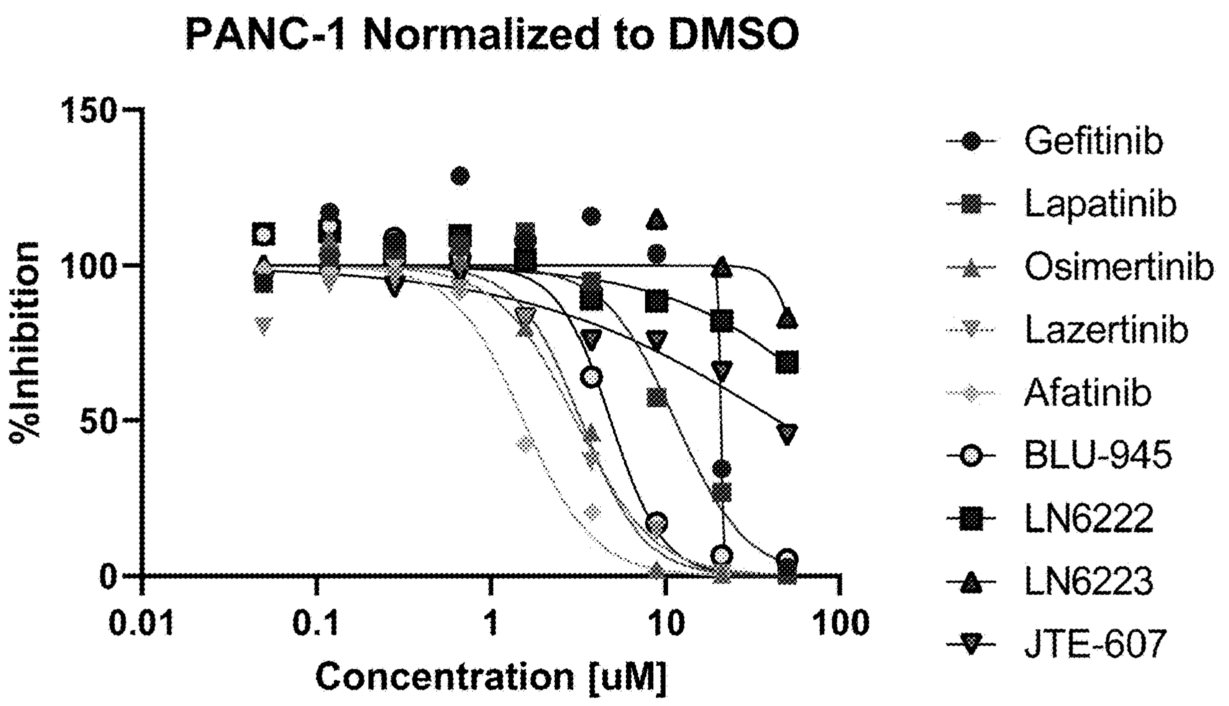
FIG. 16 shows PANC-1 PDAC cells are sensitive to JTE-607 and epidermal growth factor receptor (EGFR) inhibitors. IC50 of JTE-607 and EGFR inhibitors on PANC-1 cells after 72-hours of treatment.
Figure 17:
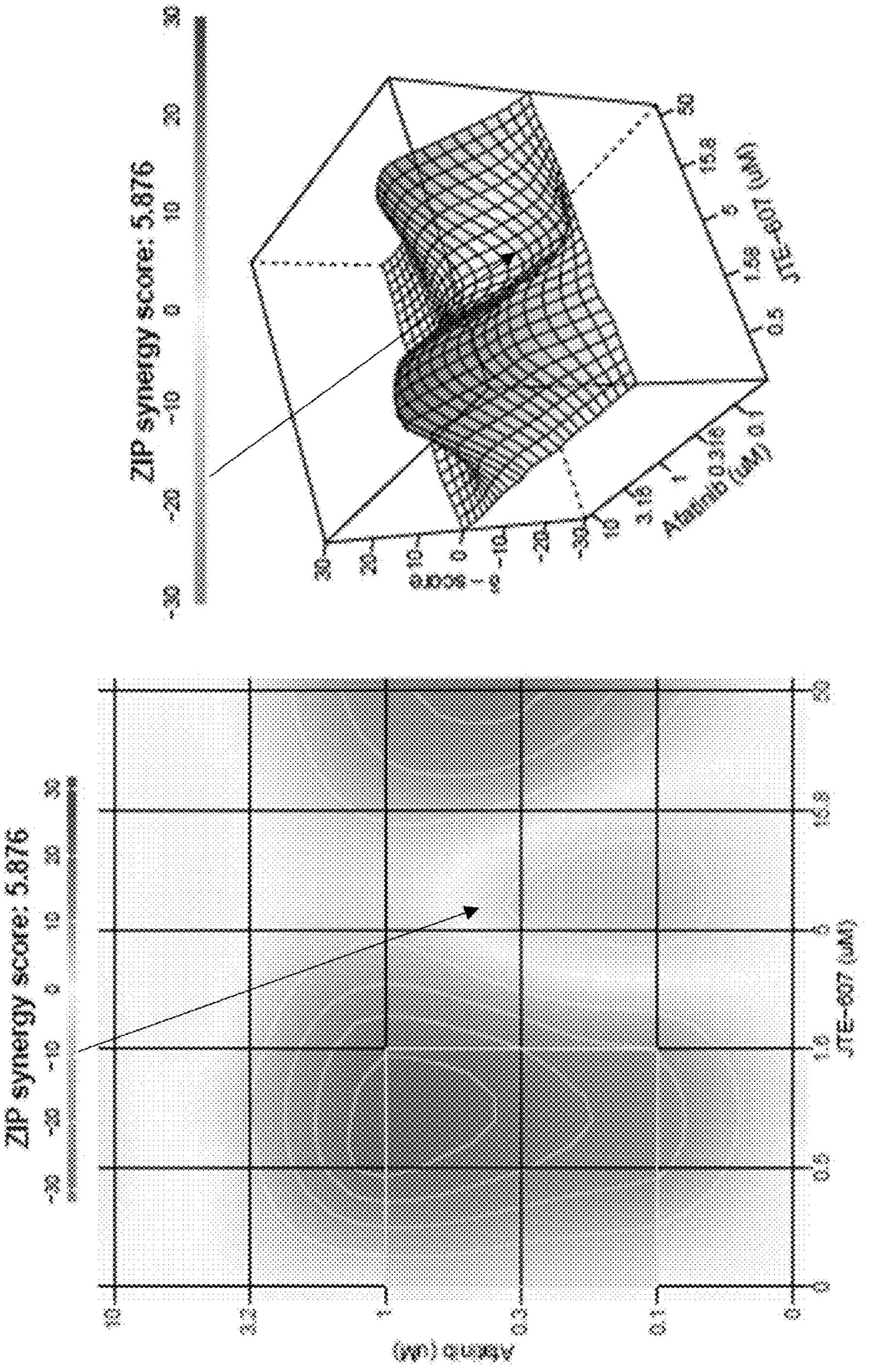
FIG. 17 shows that JTE-607 and the EGFR inhibitor afatinib are synergistic in reducing MiaPaCa2 cell proliferation, as represented by positive ZIP synergy score.
Figure 18:
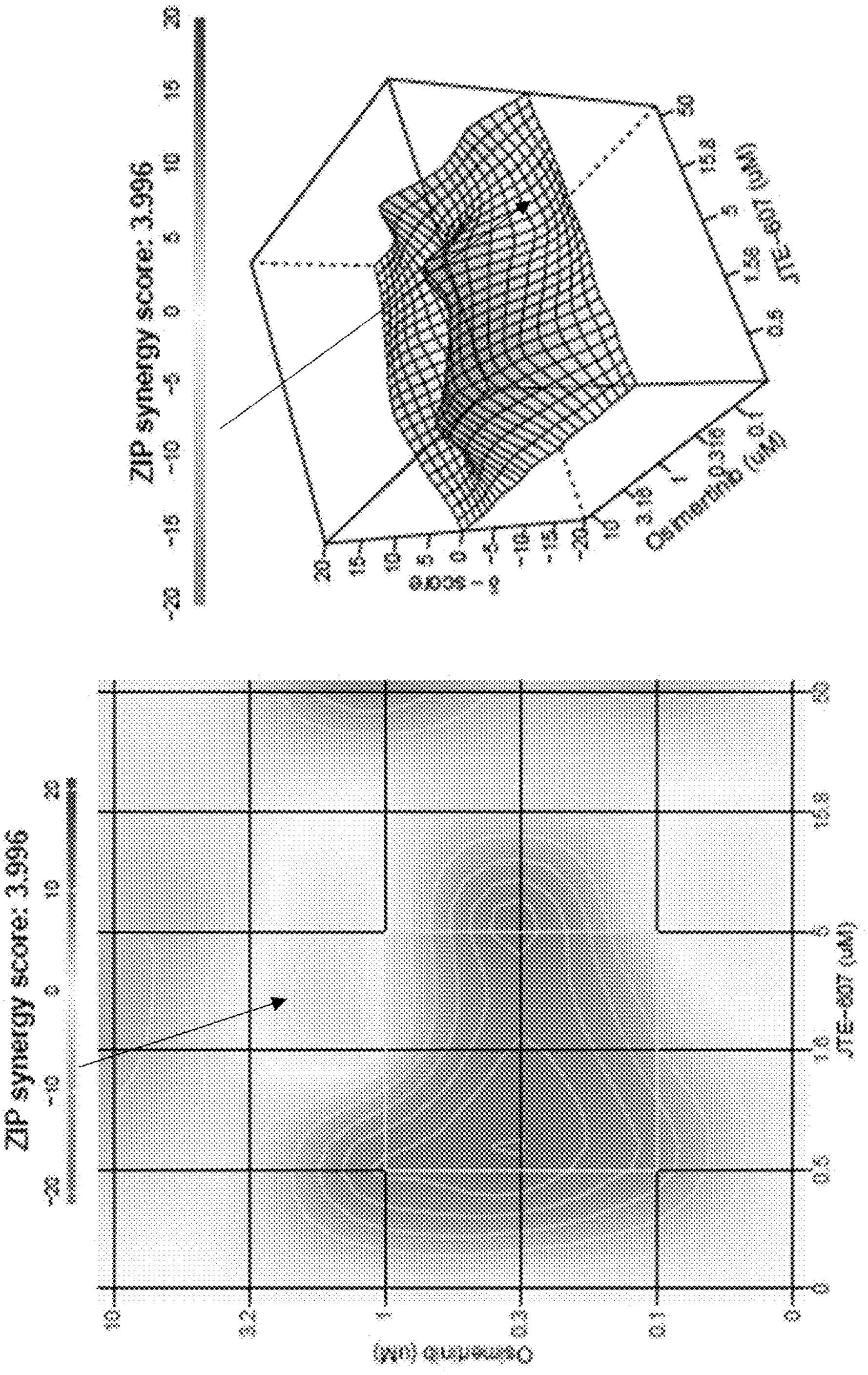
FIG. 18 shows that JTE-607 and the EGFR inhibitor osimertinib are synergistic in reducing MiaPaCa2 cell proliferation, as represented by positive ZIP synergy score.
Figure 19:
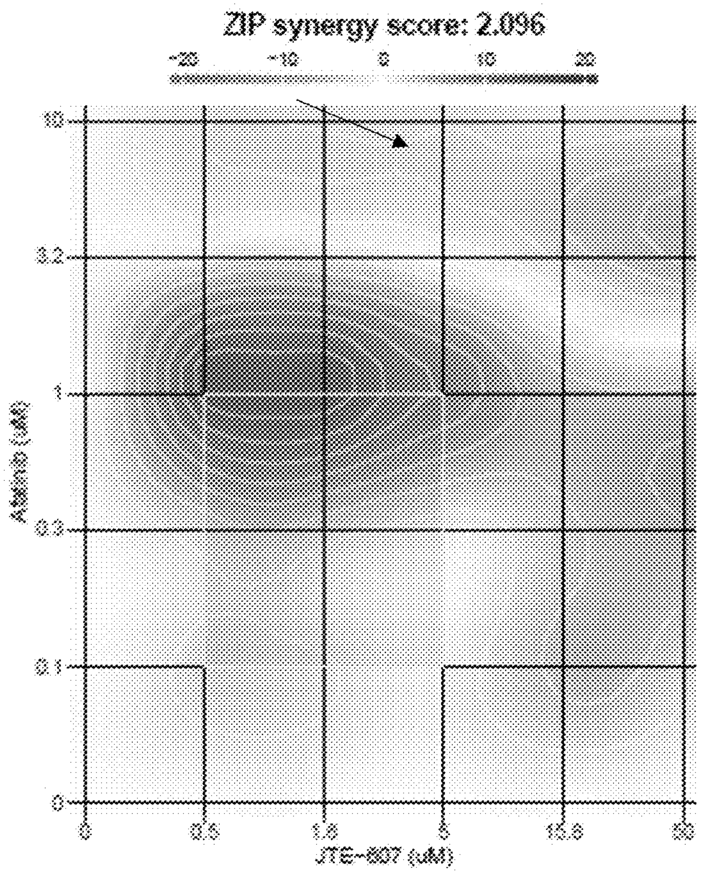
FIG. 19 shows that JTE-607 and the EGFR inhibitor afatinib are synergistic in reducing PANC-1 cell proliferation, as represented by positive ZIP synergy score.
Figure 19:
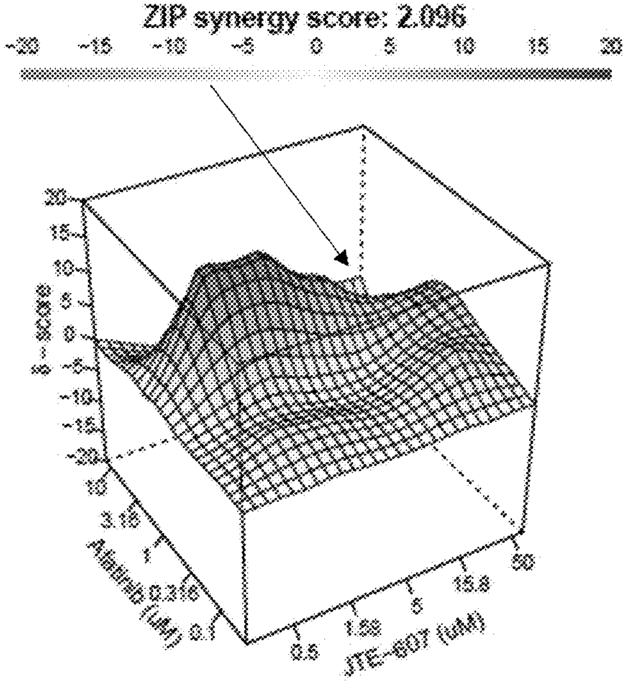
Figure 20:
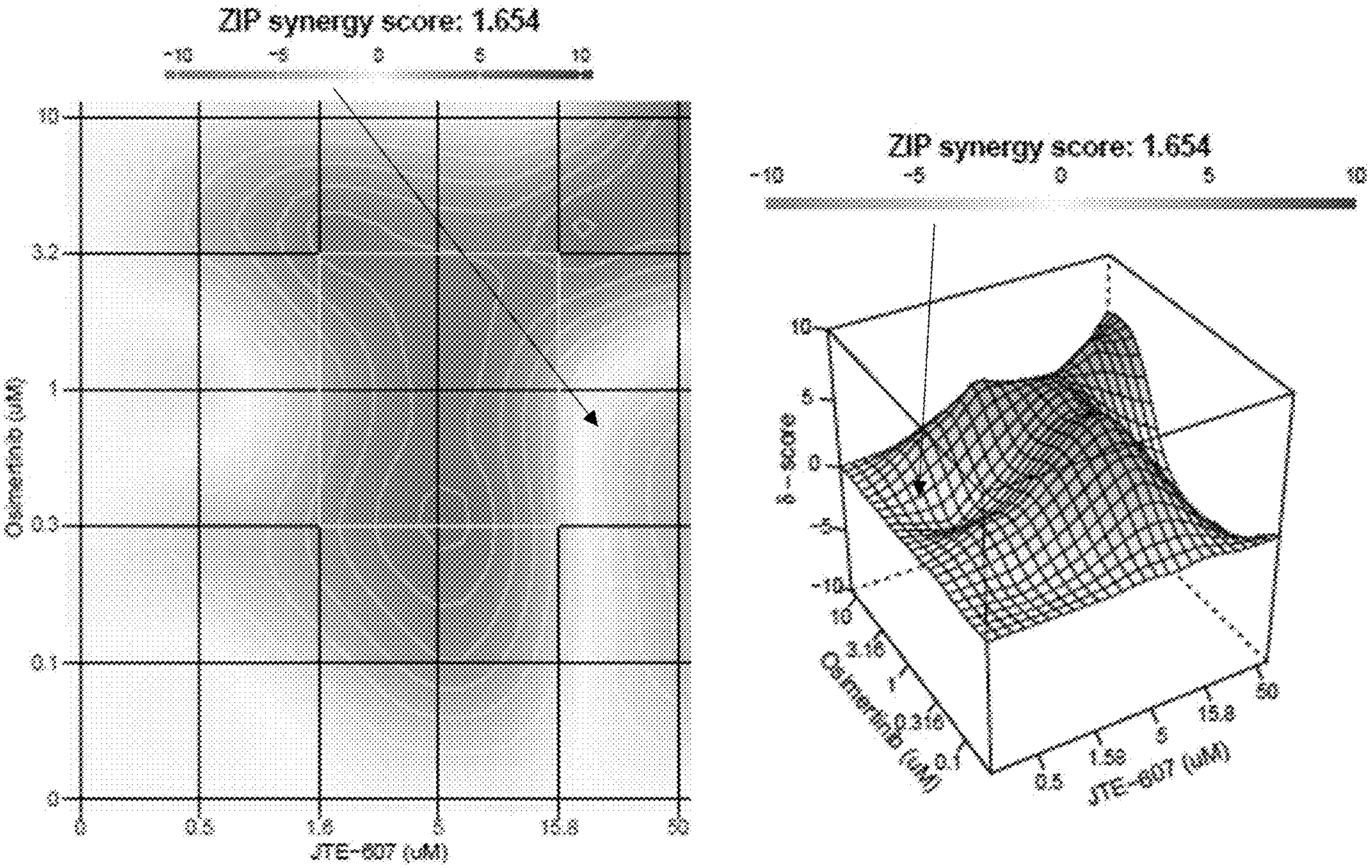
FIG. 20 shows that JTE-607 and the EGFR inhibitor osimertinib are synergistic in reducing PANC-1 cell proliferation, as represented by positive ZIP synergy score.

JTE-607 destabilizes chromatin and blocks cell cycle progression. As replication-dependent histones are required for nucleosome assembly, it was hypothesized that JTE-607 would dysregulate chromatin dynamics. Gene ontology analysis of downregulated genes showed an enrichment for chromatin-related processes including chromatin assembly, nucleosome assembly and nucleosome organization (FIG. 14A). Therefore, a Micrococcal Nuclease (MNase) assay was performed to assess relative chromatin condensation. In this assay, protein-free DNA is digested by MNase, producing DNA fragmentation patterns that are indicators of whether chromatin is in a condensed or relaxed state. The chromatin destabilizing agent CBL0137 was used as a positive control. Panc1 cells treated with JTE-607 or CBL037 displayed rapid and complete chromatin digestion, as compared with DMSO-treated cells (FIG. 6A). After 30 minutes of incubation, MNase digestion released more mononucleosomes in JTE-607 (~$4\times10^3$ normalized FU) as compared to DMSO ($1.2\times10^3$ normalized FU) (Figures S7B-S6E). Because HPNE cells are insensitive to JTE-607 (FIGS. 2A and 2C), we sought to corroborate the impact of CPSF3 inhibition on chromatin structure in HPNE cells. In contrast to Panc1 cells, HPNE cells treated with JTE-607 or CBL037 showed no chromatin digestion as compared with DMSO-treated cells (FIG. 6B). In fact, the amount of digested mononucleosomes in HPNE cells with all treatments is comparable to DMSO-treated Panc1 cells (FIGS. 14F-14I). These results suggest that JTE-607 preferentially targets cells that are in high demand for histone supplies. To assess chromatin destabilization in a living cell, the HeLa-TI cell line model that has a silenced GFP reporter within a heterochromatic region of the genome was utilized. Treatment of these cells with chromatin destabilizing agents, including CBL0137, allows derepression of GFP silencing. Therefore, GFP expression in HeLa-TI cells was monitored upon JTE-607 treatment by both fluorescence microscopy and flow cytometry. Cells treated with JTE-607 induced GFP expression to levels comparable with CBL0137 in a dose- and time-dependent manner (FIGS. 6C-6E).

Figure 7:
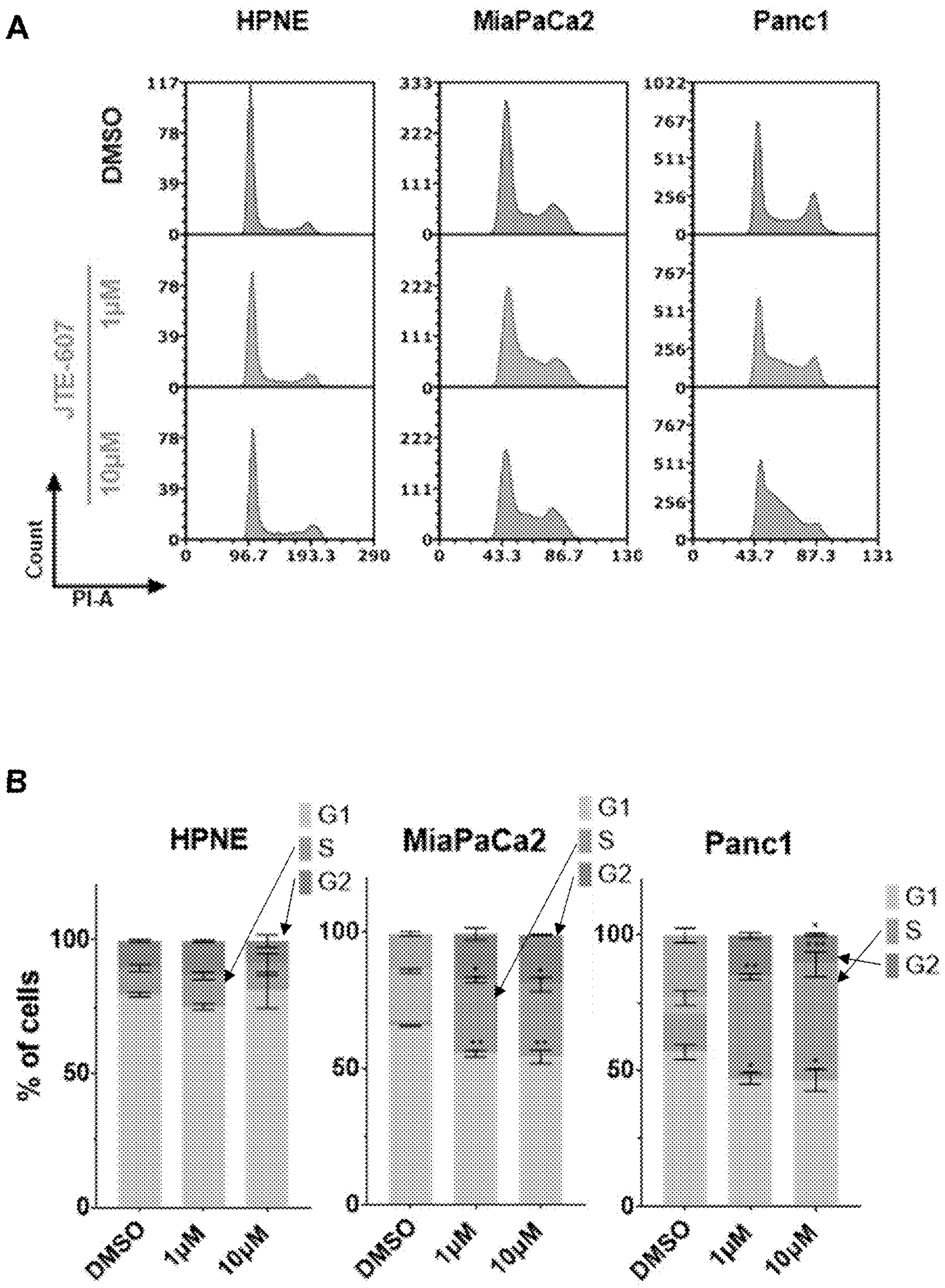
FIG. 7 shows JTE-607 impairs cell cycle progression by inducing S-phase arrest. (A, B) Cell cycle distribution and quantification of Panc1, MiaPaCa2 and HPNE cell lines treated with JTE-607. *, P<0.05, , P<0.001, *, P<0.0001, 2way ANOVA with Dunnett's multiple comparisons test. (C) Quantitative RT-PCR showing CPSF3 mRNA expression levels in HPNE cells upon CPSF3 transient knockdown by siRNA. Data are shown as mean±SEM.*, P<0.05, unpaired t test. (D, E) Cell cycle distribution and quantification of HPNE and Panc1 cell lines upon transient CPSF3 knockdown by siRNA. *, P<0.01, **, P<0.001, 2way ANOVA with Dunnett's multiple comparisons test. (F) BrdU incorporation assay showing cell cycle population upon JTE-607 treatment. Lower left quadrant represents G1 population. Lower right quadrant represents G2 population. The top two quadrants represent S phase populations; early S-phase (left) and late S-phase (right).
Figure 7:
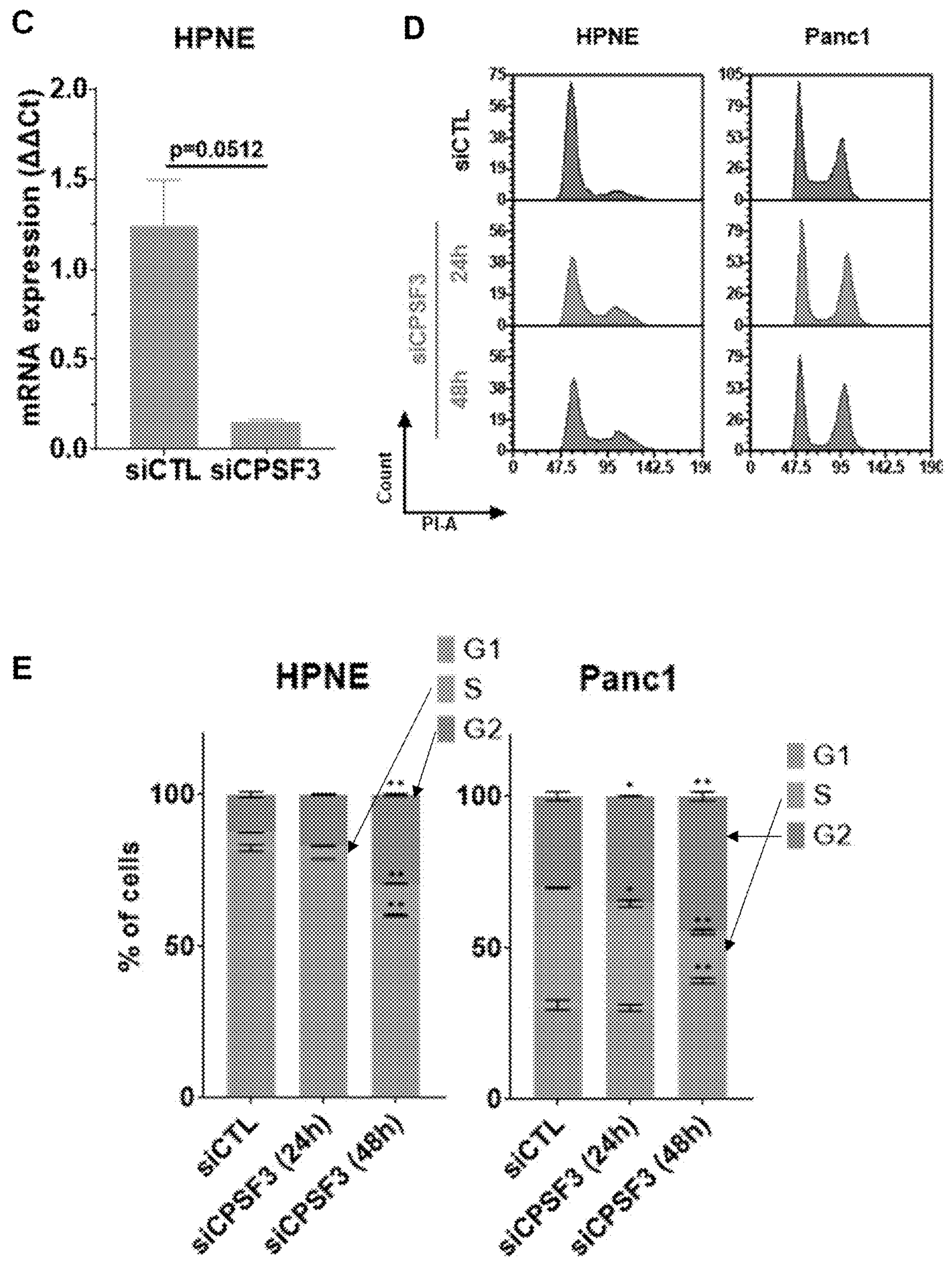
Figure 7:
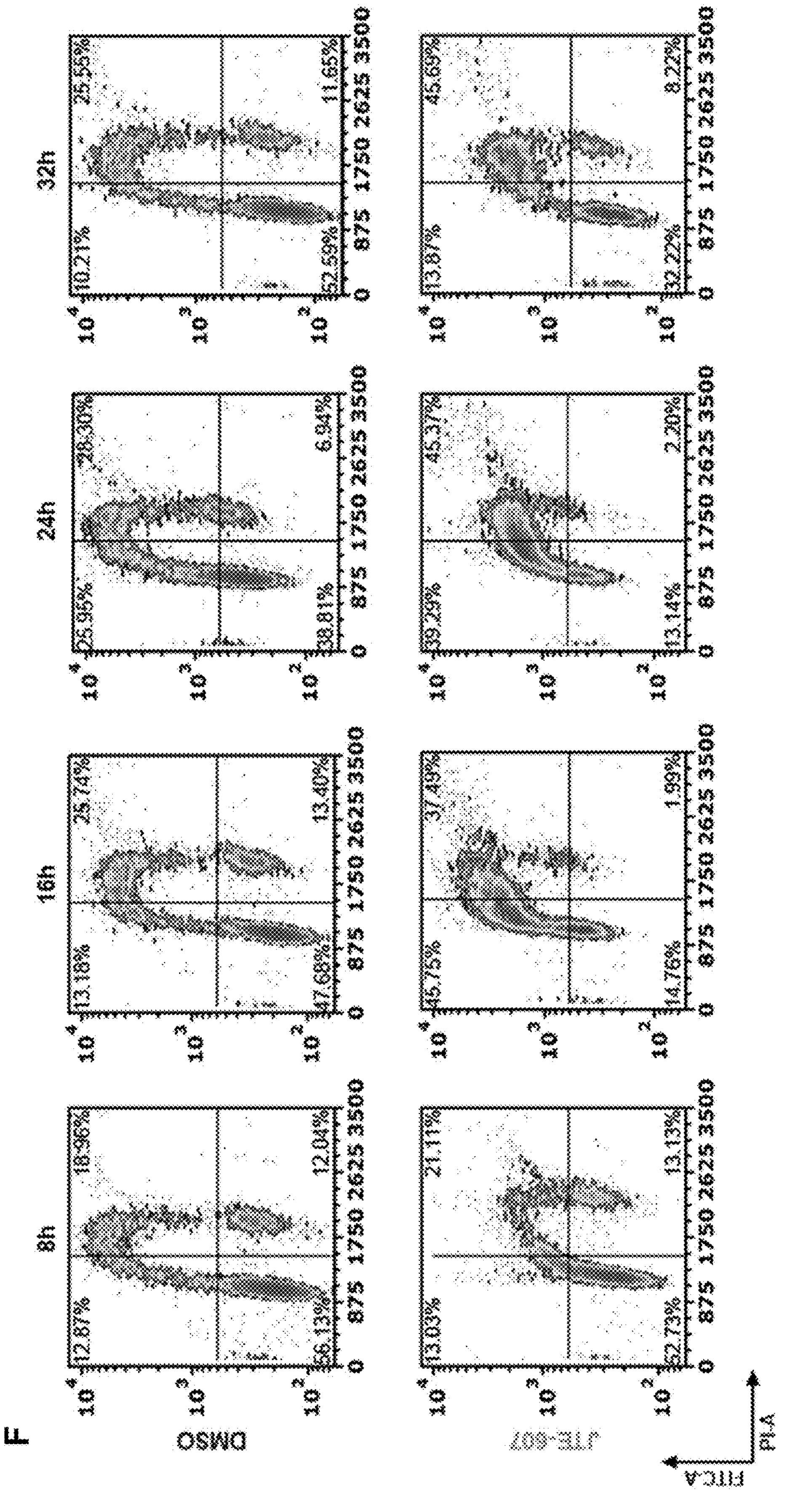

Finally, we sought to determine how JTE-607-mediated depletion of RD histones led to defects in cell viability. As RD histones are required for cell cycle progression, we assessed the effects of JTE-607 on cell cycle distribution. In non-transformed HPNE cells, JTE-607 had no impact on cell cycle distribution (FIGS. 7A and 7B). In contrast, JTE-607 arrested Panc1 and MiaPaCa2 PDAC cells in S-phase of the cell cycle within 24 hours (FIGS. 7A and 7B). To corroborate the impact of CPSF3 knockdown on cell cycle, CPSF3 was transiently knocked-down with siRNA in Panc1 and HPNE cells (FIGS. 13D, 7C). CPSF3 knockdown induced cell cycle arrest in Panc1 cells with minimal effect on HPNE cells (FIGS. 7D and 7E). However, unlike CPSF3 inhibition-induced cell cycle arrest at S-phase, CPSF3 knockdown cells arrested at G2. This pattern of cell cycle arrest is different from that induced by JTE-607 and does not resemble cell cycle arrest induced by histone defects in previous studies. This indicates that CPSF3 knockdown-induced phenotype is indeed distinct from CPSF3 inhibition. To more specifically investigate the timing and extent of S-phase arrest upon JTE-607 treatment, BrdU incorporation was examined in a time-dependent manner (FIG. 7F). It was found that JTE-607 arrests cells in early to mid S-phase of the cell cycle within 8 hours. This is in support of previous reports where histone defects slow the progression of cells during S-phase. Therefore, JTE-607 destabilizes chromatin and attenuates PDAC cell proliferation through S-phase cell cycle arrest.

Dysregulation of gene expression is a fundamental driver of cancer. This dysregulation can be driven by non-mutational epigenetic reprogramming, a mechanism that is now recognized as a hallmark of cancer. Emerging evidence has implicated dysregulation of one such non-mutational gene regulatory process, mRNA processing, in cancer. For example, pan-cancer analyses have revealed global changes in APA across the cancer landscape, and mechanistic studies have characterized how these alterations promote oncogenesis. Recently, the first large-scale, single cancer study of APA was reported and it was discovered that widespread alterations in 3'-UTR length across the PDAC landscape. Many of these APA alterations were associated with expression changes in growth-promoting genes, highlighting the importance of APA in driving PDAC pathogenesis. With regards to non-polyadenylated mRNA processing, several studies have shown that disruption of histone mRNA processing impairs cell cycle progression in multiple models. Therefore, it was hypothesized that therapeutically targeting common mRNA processing effectors in both APA and histone machineries would alleviate the aggressive proliferative state, thus normalizing the expression of growth-promoting genes and attenuating tumor growth. To directly test this hypothesis, CPSF3, an enzymatic component of the APA and histone-processing machineries that catalyzes the endonucleolytic cleavage of the pre-mRNA, was focused on. While CPSF3 has known roles in the regulation of APA and histone mRNA processing, this study defines the first roles of CPSF3 activity in an epithelial cancer, with implications for therapeutic intervention in intractable pancreatic cancer. It was demonstrate that high CPSF3 expression is a predictor of poor patient outcome and uncover the requirement for CPSF3 in PDAC cell proliferation in vitro and tumor growth in vivo. The global APA and histone read-through alterations driven by loss and inhibition of CPSF3 was characterized, revealing distinct dysregulation of both processes depending on the mode of disruption. It was then determine the direct connection between CPSF3 inhibition-mediated histone dysregulation and chromatin destabilization. Finally, it was reveal dysregulation of cell cycle progression upon CPSF3 inhibition preferentially in PDAC cells. These results demonstrate the potential for targeting CPSF3 as a novel therapeutic approach in PDAC.

This disclosure demonstrated several clinical implications. First, it was shown that CPSF3 expression is dysregulated in PDAC and high expression correlates with poor prognosis. This is consistent with similar findings across the cancer landscape, where CPSF3 has been reported to be a predictor of unfavorable prognosis in lung and liver cancers. While several studies have experimentally manipulated various mRNA processing factors and determined the phenotypic impacts, little is known about the function of CPSF3 in disease, particularly cancer. This is noteworthy for several reasons. First, CPSF3 is the enzymatic component of the APA and histone mRNA processing machineries, and is thus a potentially druggable target. Second, despite acting in the same complex, knockdown of other APA and histone mRNA processing factors can have opposing impacts on APA and histones as well as cellular phenotypes. Therefore, understanding the role of CPSF3 specifically in PDAC cell proliferation is critical for elucidating its potential as a novel therapeutic target. Recently, homozygosity in CPSF3 missense variants was found to cause intellectual disability and embryonic lethality in humans. However, these phenotypes were completely absent in the heterozygous carriers. In cancer cell line models, CPSF3 is essential for cell proliferation when knocked out completely by CRISPR; however, CPSF3 is not an essential gene upon shRNA-mediated partial knockdown (www.depmap.org). This suggests that pharmacological targeting of such an essential gene may be biologically feasible. In support of this hypothesis, it was shown that knockdown of CPSF3 blocks PDAC cell proliferation and tumor growth, and that the efficiency of knockdown is a determinant of phenotypic strength. Furthermore, CPSF3 inhibition does not impair cell cycle progression or proliferation of non-transformed pancreatic epithelial cells, and the CPSF3 inhibitor JTE-607 is non-toxic in humans. Therefore, inhibition of CPSF3 may preferentially target transformed cells.

Recently, two groups independently demonstrated that CPSF3 is the target of the small molecule JTE-607. JTE-607 was first identified over 20 years ago as a cytokine synthesis inhibitor; however, the direct molecular target remained elusive. Despite the lack of a defined mechanism, JTE-607 was tested in a Phase I dose-escalation trial in healthy human volunteers, with no serious adverse effects. Therefore, despite inhibiting an essential enzyme responsible for processing pre-mRNAs, JTE-607 is not uniformly toxic in humans. This property, coupled with the data demonstrating JTE-607's anti-proliferative effects on cancer cells, supports the contention that targeting CPSF3 is a feasible prospect in PDAC. In humans, endotoxin-induced production of C-reactive protein, IL-10 and IL-1ra was inhibited by JTE-607. In animal models, JTE-607 inhibited the production of proinflammatory cytokines, prevented endotoxin shock and attenuated artificially induced lung and heart injury. JTE-607 has also been used in models of acute myeloid leukemia (AML) and Ewing's sarcoma and showed growth inhibitory activity both in vitro and in vivo (xenograft models). However, these studies were limited to leukemia and sarcoma models, with no efficacy shown for epithelial-derived tumors. As shown herein, JTE-607 preferentially blocks proliferation of PDAC cell lines, sparing non-transformed cell lines, including epithelial cells and fibroblasts. The mechanisms underlying this difference in sensitivity are currently unknown, but may relate to variability in basal proliferation rate. This hypothesis was tested and showed that sensitivity to JTE-607 is associated with cells' proliferative state. Finally, even though JTE-607 was first described as an inhibitor of cytokine synthesis, our RNA-seq analysis did not show an enrichment of such pathways. One possible explanation is that JTE-607 action is cell type dependent. Many of the studies assessing cytokine levels were performed using measurements from blood, and therefore the cell type responsible for the changes in cytokine secretion is unknown. It is possible that the effect of JTE-607 on proliferating epithelial cells is distinct from its effect on cells within the circulation, many of which are non-proliferative when terminally differentiated. The effects of JTE-607 in different cellular contexts and cell states warrants further investigation.

No study has mechanistically connected CPSF3 to APA dysregulation. Genetic manipulation of APA factors has been shown to alter APA patterns, dysregulate gene and protein expression and drive cancer phenotypes. However, APA dynamics upon inhibition of CPSF3 activity has not been investigated. It was demonstrate that both CPSF3 knockdown and inhibition dysregulate APA in PDAC cells. Strikingly, CPSF3 influences APA in distinct patterns based on the mode of disruption. DAGs upon CPSF3 knockdown and inhibition are different with only two genes commonly altered in both conditions. Additionally, it was found that CPSF3 inhibition induces more lengthening events than CPSF3 loss. The mechanistic differences underlying the CPSF3 knockdown and inhibition effects raises several important questions. As CPSF3 is an integral subunit of the APA complex, the effect of CPSF3 knockdown and inhibition on proper recruitment of other complex components was not previously known. It was demonstrated that neither CPSF3 knockdown nor inhibition significantly alters the recruitment of other complex components. Importantly, however, the discrepancies between CPSF3 knockdown and inhibition extends to the expression of APA factors at the protein, but not gene level. CPSF3 knockdown, but not inhibition, dysregulates protein expression of APA factors. The fact that basal protein levels of APA factors are dysregulated may explain the divergence in APA patterns and gene expression alterations. Furthermore, whether CPSF3 knockdown and inhibition distinctly influence PAS selection has not been previously studied. Here, it was demonstrated that DAGs upon CPSF3 knockdown and inhibition possess different motifs surrounding the PAS. Such differences have been shown to influence PAS selection thus inducing distinct APA patterns. Therefore, these results support the development of CPSF3 targeting agents, including those that can specifically degrade CPSF3.

A previous report demonstrated that JTE-607 attenuates cell proliferation in AML and Ewing's sarcoma through increasing R-loop formation and downregulating the expression of DNA damage response genes. R-loops are DNA:RNA hybrids that form as a result of aberrant transcription, a characteristic of cancers with genetic rearrangements such as AML and Ewing's sarcoma. Of note, R-loops increase in models with mRNA cleavage and polyadenylation defects, suggesting that sensitivity of AML and Ewing's sarcoma to JTE-607 may be a consequence of high basal levels of R-loops, which eventually accumulate leading to DNA damage and genomic instability. In this study, gene set enrichment analysis did not reveal changes in DNA damage response pathways upon CPSF3 knockdown or inhibition in PDAC cells. Therefore, we propose that CPSF3 regulates cell proliferation through distinct mechanisms in AML and Ewing's sarcoma relative to PDAC. In PDAC cells, it was found that JTE-607 impairs processing of proliferation-dependent (RD) histone mRNAs. This is consistent with the role of CPSF3 in the HCC. Defects in the HCC have been shown to reduce the availability of RD histones. However, prior to now, no studies have described the effect of CPSF3 inhibition on HCC activity. Depletion of many HCC genes led to an accumulation of histone read-through transcripts in the nucleus. Similarly, it was found that extensive transcript read-through in RD histone mRNAs, but not RI histone mRNAs upon JTE-607 treatment in PDAC cells. In accordance with a previous study, however, CPSF3 knockdown did not induce RD transcriptional read-through. Importantly, neither CPSF3 loss nor inhibition induced histone transcriptional read-through in non-transformed cells. This is consistent with the notion that slowly proliferating cells do not have high levels of RD histone transcription. Histone read-through transcripts accumulate in the nucleus, thus failing to be exported into the cytoplasm and translated into protein. In accordance with this model, it was found that JTE-607 decreases gene and protein levels of core histones in PDAC cells. Limited histone supplies destabilize chromatin integrity through disruption of nucleosome assembly. It was that JTE-607 destabilizes chromatin stability in PDAC but not non-transformed cells, as demonstrated by increased sensitivity to MNase digestion, and derepression of heterochromatin-mediated gene expression silencing. These findings reveal a novel mechanism of JTE-607 activity: dysregulation of RD histone mRNA processing.

Expression of RD histones increases ~30-50 fold during DNA synthesis. The life cycle of these core histone genes starts late in G1 through mid S phase of the cell cycle and degradation occurs at late S phase. Silencing of the HCC core component FLASH induces S phase arrest in HeLa cells. It was found that JTE-607 arrests cells in the S phase of the cell cycle, with cells slowly cycling through early-mid S phase but failing to progress through late S phase. This s consistent with a previous study where depletion of the histone chaperone ASF1, an important gene for historic deposition during DNA replication, disrupts progression through mid to late S-phase. Importantly, silencing of MBLAC1, a recently identified endonuclease selective for 3' processing of RD histone pre-mRNAs, significantly impairs cell cycle progression during S-phase. In addition, knockdown of CSTF2, a gene with dual functions in APA and histone pre-mRNA processing, delays progression through S phase, but its expression is highly dependent on cell cycle stage. The same study showed that CPSF3 expression is not cell cycle regulated, suggesting that the histone phenotype was observed is driven by CPSF3 inhibition and not merely a consequence of cell cycle arrest. Although CPSF3 knockdown induced cell cycle arrest, this pattern of cell cycle arrest is distinct from that induced by JTE-607 in our study and by histone disruption in previous reports. These findings strongly suggest that ITE-607 mediates its growth attenuating phenotype by reducing histone supplies during S phase, thereby blocking cell cycle progression.

JTE-607-mediated cell cycle arrest may promote synergism with cell cycle check-point inhibitors. For instance, the chromatin remodeling histone deacetylase (HDAC) inhibitors have shown synergistic effect when combined with checkpoint kinase 1 (Chk1) inhibitors in lung cancer models. Histone disruption by JTE-607 may also promote synergism with chromatin modifying drugs. For example, CBL0137 has shown synergistic effect when combined with HDAC inhibitors by exacerbating chromatin destabilization. These discoveries may improve the efficacy of approved chromatin remodeling agents and suggest a path forward for use of JTE-607 in the clinic.

In conclusion, the present disclosure has revealed the role of CPSF3 in pancreatic cancer and uncovered a new mechanism by which CPSF3 mediates cell proliferation. The mode of CPSF3 disruption induces distinct mRNA processing changes on both APA and histone processing levels. CPSF3 inhibition disrupts the processing of RD histones, destabilizing chromatin structure and inhibiting cell cycle progression. Our findings reveal novel insight into how CPSF3 inhibition blocks cell proliferation and provides a new therapeutic target in pancreatic cancer.

KEY RESOURCES TABLE

| REAGENT or RESOURCE | SOURCE | IDENTIFIER |
|---|---|---|
| Animal and Cell Line models | | |
| HEK293T | ATCC | CRL-3261 |
| MiaPaCa2 | ATCC | CRL-1420 |
| Panc1 | ATCC | CRL-1469 |
| Suit2 | Dr. David Tuveson | N/A |
| HeLa-TI | Dr. Katrina Gurova | N/A |
| HPNE | Dr. Ethan Abel | N/A |
| HPDE | Dr. Ethan Abel | N/A |
| C7 CAFs | Dr. Edna Cukierman | N/A |
| PancPat | Dr. Edna Cukierman | N/A |
| NOD/SCID/ IL2Rγ−/−(NSG) mice | RPCC | N/A |
| Culture media and chemicals | | |
| DMEM | Corning | Catalog # MT 10-013-CV |
| Medium M3 Base | Incell Corp. | Catalog # M300F-500 |
| Keratinocyte SFM | Thermo Scientific | Catalog # 17005042 |
| FluoroBrite DMEM | Thermo Scientific | Catalog # 1896701 |
| Fetal bovine serum | Corning | Catalog # MT 35-011-CV |
| Penicillin-streptomycin | Thermo Scientific | Catalog # 15140163 |
| GlutaMAX | Thermo Scientific | Catalog # 35050061 |
| Sodium bicarbonate | Corning | Catalog # MT 25-035-CI |
| Matrigel | Corning | Catalog # 356231 |
| BrdU | Sigma-Aldrich | Catalog # B5002 |
| TRIzol reagent | Thermo Scientific | Catalog # 15596026 |
| Pierce ECL Substrate | Thermo Scientific | Catalog # 32106 |
| Supersignal West Femto substrate | Thermo Scientific | Catalog # 34094 |
| Nitrocellulose membranes | Bio-rad | Catalog # 1620112 |
| Kits and commercial assays | | |
| Direct-zol RNA Miniprep Kit | Zymo Research | Catalog # R2050 |
| iScript cDNA Synthesis Kit | Bio-rad | Catalog # 1708891 |
| iTaq Universal SYBR Green mix | Bio-rad | Catalog # 1725120 |
| CellTiter-Glo Cell Viability Assay | Promega | Catalog # G7571 |

-continued

KEY RESOURCES TABLE

| REAGENT or RESOURCE | SOURCE | IDENTIFIER |
|---|---|---|
| Dynabeads ™ Protein G IP Kit | Thermo Scientific | Catalog # 10007D |
| Short-hairpin RNAs | | |
| sh1 RNA against CPSF3 | Sigma-Aldrich | Clone ID: NM_016207.2-219s1c1 |
| sh2 RNA against CPSF3 | Sigma-Aldrich | Clone ID: NM_016207.2-1240s1c1 |
| Small-interfering RNAs | | |
| siGENOME non-targeting control | Horizon Discovery | Catalog # D-001206-13-05 |
| siCPSF3 Smartpool | Horizon Discovery | Catalog # M-006365-00-0005 |
| PCR primers | | |
| CPSF3 | Bio-rad | Unique Assay ID: qHsaCID0007422 |
| ACTB | Bio-rad | Unique Assay ID: qHsaCED0036269 |
| HIST1H3B | Bio-rad | Unique Assay ID: qHsaCED0007746 |
| HIST1H2BC | Bio-rad | Unique Assay ID: qHsaCED0007746 |
| Histone read-through primers | | |
| See Tables 1-8 for list of primers | This paper | Ordered from IDT |
| Antibodies | | |
| CPSF3 antibody (WB) | Abcepta | Catalog # AT1610a |
| CPSF3 antibody (IHC) | Atlas Antibodies | Product # HPA034657 |
| Ki-67 antibody (IHC) | Novus Biologicals | Catalog # NB600-1209 |
| Histone H2B antibody | Cell Signaling | Catalog # 8135S |
| Histone H3 antibody | Cell Signaling | Catalog # 9715S |
| CSTF64 antibody | Bethyl Laboratories | Catalog # A301-092A |
| CPSF68 antibody | Bethyl Laboratories | Catalog # A301-358A |
| CPSF1 antibody | Bethyl Laboratories | Catalog # A301-580A |
| CPSF2 antibody | Novus Biologicals | Catalog # NB100-79823 |
| CPSF4 antibody | Novus Biologicals | Catalog # NB100-79826 |
| NUDT21 antibody | Santa Cruz | Catalog # SC-81109 |
| CSTF77 antibody | Santa Cruz | Catalog # SC-376575 |
| Mouse IgG isotype | GeneTex | Catalog # GTX35009 |
| Rabbit IgG isotype | GeneTex | Catalog # GTX35035 |
| Donkey anti-rabbit | Fisher Scientific | Catalog # 45-000-682 |
| Goat anti-mouse | Sigma-Aldrich | Catalog # A4416 |
| GAPDH antibody | Proteintech | Catalog # 60004-1-Ig |
| Anti-BrdU-FITC | BioLegend | Catalog # 364104 |
| Software and algorithms | | |
| Real-Time PCR Detection System | CFX connect system | Catalog #1855201 |
| Image analysis | ImageJ | https://imagej.nih.gov/ij |
| Image acquisition | ChemiDoc XRS+ | Catalog # 1708265 |
| Image analysis | Image Lab Software | Image Lab; Bio-rad |
| Data analysis | Graphpad prism v9 | https://www.graphpad.com/ |

-continued

KEY RESOURCES TABLE

| REAGENT or RESOURCE | SOURCE | IDENTIFIER |
|---|---|---|
| Data analysis | FCS express | https://denovosoftware.com/ |
| DNA visualization | Tape Station 4200 | Genomic Shared Recourses, RPCC |
| APA analysis | Poly Aminer-Bulk | https://github.com/venkatajonnakuti/PolyAMiner-Bulk |
| Read-through analysis | ARTDeco | https://github.com/sjroth/ARTDeco |
| RD histone survival analysis | GEPIA2[80] | http://gepia2.cancer-pku.cn/#index |
| Drugs | | |
| JTE-607 dihydrochloride | Tocris | Catalog # 5185 |
| Curaxin (CBL0137) | Dr. Katerina Gurova | N/A |
| Digestion enzymes | | |
| Micrococcal nuclease | NEB | Catalog # MO247S |

Cell lines and in vitro culture. HEK293T, MiaPaCa2, Panc1, Suit2, Human immortalized C7 CAFs and PancPat CAFs cells were cultured in DMEM (DMEM [+] 4.5 g/L glucose, L-glutamine, sodium pyruvate) supplemented with 10% fetal bovine serum (FBS) and 1% penicillin-streptomycin. Non-transformed pancreatic cell line HPNE cells were cultured in 75% DMEM+25% Medium M3 Base supplemented with 2 mM L-glut, 1.5 g/L sodium bicarbonate, 5% FBS, 10 ng/mL hEGF and 5.5 mM D-glucose. Non-transformed pancreatic cell line HPDE cells were cultured in Keratinocyte SFM (serum-free media) supplemented with 25 mg BPE, 2.5 μg EGF, 1×anti-anti and 50 μg/mL Gentamicin. HeLa-TI cells were cultured in phenol red-free FluoroBrite DMEM complete Media. All cell lines were cultured at 37° C. with 5% $CO_2$ and tested negative for *Mycoplasma.*

Generation of stable and transient CPSF3 knockdown cells. For stable knockdown, two vectors expressing short-hairpin RNA (shRNA) targeting CPSF3 were purchased from Sigma-Aldrich. Cells were infected with lentivirus harboring pLKO.1-shNTC (non-targeting control) and pLKO.1-shCPSF3 at 40% confluency. Polybrene was used to increase the efficacy of infection. After 72 hours, cells were selected with 2.5 μg/ml puromycin. Knockdown was confirmed by qPCR and immunoblotting. For transient knockdown, cells were plated at ~$1.5\times10^5$-$2.5\times10^5$ cells per well in a 6-well plate one day prior to transfection. The next day cells were transfected with 60 nM of siRNA against CPSF3 and a non-targeting control. Transfection media were replaced with complete media 6 h after transfection. After 24 h and 48 h of transfection, cells were collected for subsequent experiments.

RNA isolation and quantitative PCR. Cells were lysed with TRIzol reagent. RNA was isolated using Direct-zol RNA Miniprep. cDNA was synthesized using iScript cDNA Synthesis Kit. qPCR was conducted with SYBR Green PCR primers mixed with iTaq Universal SYBR Green Supermix and run on CFX connect systems (Bio-Rad). Data were analyzed in Microsoft Excel and graphed using GraphPad Prism (v 9.3.0).

RNA-sequencing. Cells were trypsinized, washed with 1×PBS and sent frozen (−80° C.) for RNA sequencing (RNA-seq). 500 ng total RNA was used to prepare the sequencing libraries using KAPA RNA HyperPrep Kit with RiboErase (HMR) (Roche Sequencing Solutions) following manufacturer's protocol. Briefly, ribosomal RNA (rRNA) was depleted from total RNA and DNase-digested to remove gDNA contamination. RNA was purified, fragmented and first strand cDNA was synthesized using random primers. cDNA:RNA hybrids were converted into double-stranded cDNA (dscDNA) using dUTP incorporation. Adapters were added to the 3' ends, ligated to library insert fragments and the library amplified in a strand-specific manner. Data were analyzed by the Bioinformatics Shared Resource (Roswell Park Comprehensive Cancer Center).

Nuclear isolation. Cells were grown and collected at 80-90% confluence for nuclei isolation. Briefly, Cells were washed with cold 1×PBS and then incubated with hypotonic buffer (10 mM Tris pH 8, 1.5 mM $MgCl_2$, 2 mM KCl) for 15 minutes. Cells were scraped and nuclei release was assessed under the microscope using trypan blue staining. Cell suspension was centrifuged at 2000 rpm for 5 minutes at 4° C. Pellets were washed with hypotonic buffer and centrifuged at 700×g for 5 minutes at 4° C. Pellets (nuclei) were lysed using NP40 lysis buffer for 1 hour while rotating at 4° C. and sonicated once at the end. Nuclear lysate was centrifuged at max speed for 10 minutes at 4° C. Supernatant was collected as the final nuclear lysate.

Immunoprecipitation. Immunoprecipitation was performed using protein G beads. Briefly, beads were mixed thoroughly and washed twice with 1×TBS-T buffer (25 mM Tris, 0.15 M NaCl, 0.05% Tween-20 Detergent) containing protease and phosphatase inhibitors. Beads were collected using magnetic stand to remove wash buffer. To preclear the samples, 1 mg of sample was added to the beads and incubated with rotation for 1 hour at 4° C. Beads were separated from the lysate using magnetic stand, and precleared samples were transferred to a clean tube. New magnetic beads (~25 μL/1 mL lysate) were washed twice, and precleared samples were added to the beads. Antibodies (IgG control or target antibody) were added to lysates and incubated overnight on rotator at 4° C. Beads were collected using magnetic stand and supernatant (unbound proteins) was discarded. Magnetic beads were washed twice with cold 1×TBS-T buffer and once with ultrapure water then collected on magnetic stand. Finally, beads were incubated with 100 μL of SDS-PAGE Sample Buffer containing reducing agent at 95° C. for 5-10 minutes. Magnetic beads were separated, and the supernatant was used for western blot analysis.

Immunoblotting. For whole cell lysates, samples were lysed using RIPA lysis buffer (50 mM Tris. HCl pH 7.5, 150 mM NaCl, 5 mM EDTA pH 8, 1% Triton X-100, 0.5% NP-40) in the presence of 10 μg/mL protease inhibitors (Aprotinin, Leupeptin, PMSF), boiled at 95° C. for 5 min and resolved by SDS-PAGE. Proteins were transferred to nitrocellulose membranes at a constant voltage of 100V for 70 minutes at 4° C. using Mini Trans-Blot® Cell (Bio-Rad). Membranes were blocked in TBST (Tris-buffered saline (TBS) with 0.1% v/v TWEEN-20) and 5% w/v nonfat dry milk. Primary antibodies were diluted in 3% BSA in TBST and incubated overnight at 4° C. Membranes were incubated with horseradish peroxidase-conjugated secondary antibodies at 1:2,000 for 1 hour at room temperature. Pierce ECL Western Blotting Substrate or Supersignal West Femto Maximum Sensitivity substrate were used for chemiluminescent detection. Signals were visualized and imaged using the ChemiDoc XRS+ System and Image Lab Software (Bio-Rad).

Proliferation and clonogenicity assays. For proliferation experiments, cells were seeded at a density of 250 cells/well (MiaPaCa2 and Panc1 cells) or 1000 cells/well (HPNE cells) into a white 96-well plate in triplicate. Cell proliferation was measured using CellTiter-Glo Luminescent Cell Viability Assay Kit at days 0, 2, 4 and 6. For clonogenicity assays, cells were seeded at a density of 500 cells/well into a 6-well plate in triplicate. After 11 days, cells were fixed with 4% formalin, stained with 0.2% Crystal Violet and images were obtained for analysis. Colony area was measured using ImageJ software. Data were normalized to control data points.

Cell cycle analysis. Cells were trypsinized and resuspended in 1×PBS, then fixed with ice-cold 70% ethanol for 1 hour at −20° C. Cells were then washed with cold 1×PBS and incubated with RNaseA (200 μg/ml) at 37° C. for 1 hour. Propidium iodide (40 μg/ml) was then added, incubated for 1 hour in the dark and analyzed by FACS at 488 nm. Data were analyzed by FCS express software (v7.06.0015).

BrdU incorporation assay. Cells were cultured under optimum conditions and incubated with 50 μM BrdU (5-Bromo-2'-deoxyuridine; Sigma-Aldrich; B5002) for 4 hours. Cells were then rinsed with 1×PBS, trypsinized, permeabilized in 70% ice cold ethanol with gentle vortexing and stored at −20° C. overnight. Next, cells were pelleted and DNA was hydrolyzed by incubating with 500 μL of 2N HCl, 0.5% Triton X-100 in 1×PBS, incubated for 30 minutes at room temperature and then neutralized by adding 1.5 mL of 0.1 M sodium tetraborate (pH 8.5) for 2 minutes. Cells were then pelleted, washed once with 1% BSA in 1×PBS and resuspended in 50 μL 0.5% Tween 20, 1% BSA in 1×PBS. Next, $10^6$ cells were incubated with 1 μg Anti-BrdU-FITC for 1 hour at room temperature. Cell pellets were washed once with 150 μL 1% BSA in 1×PBS, resuspended in 500 μL 1×PBS with RNaseA (200 μg/ml) and PI (40 μg/ml) and incubated at room temperature for 30 minutes in the dark. Cells were analyzed by flow cytometry immediately and a compensation step was performed. Data were analyzed by FCS Express software (v7.06.0015).

Xenograft experiments. Animal experiments were approved by the Roswell Park Institutional Animal Care and Use Committee. MiaPaCa2 cells infected with shNTC and sh1 CPSF3 constructs were trypsinized, washed with 1×PBS and counted. $5 \times 10^5$ cells were resuspended in 50 μl of 1×PBS/Matrigel in a 1:1 ratio and injected subcutaneously into the flanks of 8-week old NOD/SCID/IL2Ry−/−(NSG) mice. When palpable, tumor volume was determined by caliper measurements obtained in 2 dimensions and calculated as $width^2 \times length/2$ twice a week. Mice were euthanized when the first tumor reached 1400 $mm^3$, tumors were dissected, and tumor volumes were measured.

Histology and Immunohistochemistry. Freshly dissected tumors were fixed in 10% neutral buffered formalin solution (Sigma-Aldrich, Cat. #HT501128) for 24 hours prior to processing. Tumor processing was performed by the Experimental Tumor Model (ETM) Shared Resource team at RPCC. Briefly, Formalin-fixed paraffin embedded (FFPE) blocks were sectioned (5 μm), rehydrated, stained with hematoxylin and eosin, dehydrated, dried, and mounted. For immunohistochemistry, after deparaffinization and rehydration, antigen unmasking was performed using Retriever 2100 pressure cooker (Aptum). Slides were then immunostained overnight at 4° C., washed, treated with ImmPRESS Polymer reagent (Vector Laboratories) and counterstained. Slides were visualized using OLYMPUS BX41 microscope, imaged using CellSens Standard software and analyzed using ImageJ.

JTE-607 studies. For dose-response measurements, cells were seeded at a density of 1000 cells per well in a 96-well white plate. The next day, JTE-607 was titrated over a range of concentrations using the Tecan D300e Digital Dispenser and cell viability was measured 72 hours post drug titration using a CellTiter-Glo Luminescent Cell Viability Assay Kit (Promega). For cell proliferation experiments, cells were seeded at a density of 250 cells per well in a 96-well white plate. DMSO control or JTE-607 was dispensed at varying concentrations and proliferation was measured using Cell-Titer-Glo Assay at days 0, 2, 4 and 6. For clonogenicity experiments, cells were seeded at a concentration of 500 cells per well and treated with different concentrations of JTE-607. Cells were allowed to grow over a period of 11-14 days after which they were fixed in 10% formalin, stained with 0.2% Crystal Violet and images were obtained for analysis. Colony area was measured using ImageJ software. Data were normalized to DMSO control data points.

Micrococcal digestion. Micrococcal Nuclease (MNase) was performed as previously described. Briefly, cells were trypsinized, washed with 1×RSB buffer (10 mM Tris HCL, pH 7.6; 15 mM NaCl; 1.5 mM $MgCl_2$) and pelleted at 1000 rpm for 4 minutes at room temperature. Cell pellets were resuspended in 1×RSB buffer with 1% TritonX-100, homogenized with a loose pestle (5 strokes) and centrifuged for 5 minutes at 2000 rpm at 4° C. Pellets were washed two times with 1 ml of buffer A (10 mM Tris HCL, pH 7.6; 15 mM NaCl; 60 mM KCl; 0.34 M Sucrose; 0.1% B-mercaptoethanol; 0.15 mM Spermine; 0.5 mM Spermidine; 0.25 mM PMSF) and nuclei were pelleted at 160 g for 10 minutes at 4° C. Nuclei were resuspended in 1.5 mL of buffer A supplemented with 1 mM of $CaCl_2$). Nuclear suspensions (500 μL) were digested with 200 U/mL Micrococcal nuclease at 37° C. at different time points. Digestion was inactivated by 15 mM EDTA. 10% SDS and 1 M NaCl were added to extract genomic DNA. DNA was run and visualized using TapeStation 4200 system.

Differential gene expression analysis. Raw sequencing reads passed quality filter from Illumina RTA were first pre-processed by using FASTQC (v0.11.8) for sequencing base quality control. The reads were mapped to GRCh38 human reference genome and GENCODE (v38) annotation database using STAR (v2.7.9a). Alignment files are indexed using samtools (v1.14). A Second pass QC was done using alignment output with RSeQC (v4.0.0) to examine abundances of genomic features, splicing junction saturation and gene-body coverage. Gene expression was quantified using featureCounts (v2.0.0) with—fracOverlap 1 option and then formatted in a raw counts data matrix. Differential expression analyses were performed with DESeq2 (v1.36.0), a variance-analysis package developed to infer statistically significant differences in RNA-seq data using a Negative Binomial GLM. Genes are called differentially expressed (DE) when having a Fold-Change (FC)>1.5 and FDR<0.05 (using Benjamini-Hochberg method to control false discovery rate). Downstream and visualization plots were done using regularized-log 2 transformation implemented by DESeq2. Heatmaps were generated using the pheatmap (v1.0.8) R package.

3'UTR alternative polyadenylation analysis. APA analysis was done using PolyAMiner-Bulk. For each sample, PCR duplicates were identified using UMI bar codes. UMI tools extract was used to extract the UMI nucleotides from the reads and append them to the read names. Initial quality control was performed using fastp. Reference human genome and annotations of the build GRCh38 release 33 were downloaded from the GENCODE portal. UMI marked and trimmed reads were aligned to respective reference genomes using STAR version 2.7.3a. Sample-wise alignments were saved as Sequence Alignment Map (SAM) files. SAMtools V0.1.19 'view', 'sort' and 'index' modules were used to convert the SAM files to Binary Alignment Maps (BAM) files, sort by chromosomal coordinates, and index respectively. Mapped reads are deduplicated using UMI tools dedup based on the UMI marked read names and the mapping coordinates. Alternative polyadenylation (APA) analysis was performed using PolyAMiner-Bulk. Samples were processed with the following parameters: -a 0.65 -pa_p 1 -pa_a 5 -pa_m 5 -outPrefix 3UTROnly -expNovel 1 -s 2 -ignore UTRS,CDS,Intron,UN -apriori annotations -modelOrganism human. APA analysis focusing only on 3'UTR regions was performed by excluding the polyA sites mapped to other genomic regions with the parameter -ignore UTRS, CDS,Intron,UN. Total reads per feature were computed by adding all individual C/PAS site counts mapped to respective features and total gene counts were computed as the sum of all individual feature C/PAS counts. A beta-binomial test was performed using the proportions of individual feature counts to the total gene counts to infer differential C/PAS usage changes.

Motif enrichment analysis. To discover novel, ungapped motifs of recurring, fixed-length patterns in our sequence datasets, the STREME methodology was employed. STREME (Simple, Thorough, Rapid, Enriched Motif Elicitation) discovers ungapped motifs that are enriched in our sequence datasets. For the input, the unique sets of shortening and lengthening 3'UTR sequences for each condition were used, all 100 bp in length, referencing the sequence database Human hg38 (UCSCMammal/hg38.fna). The program shuffles each set to create a corresponding control set and uses a Fisher's Exact Test to determine significance of each motif found in the positive set as compared with its representation in the control set, using an adjusted p-value significance threshold of 0.05.

Global Read-through analysis. ARTDeco (v0.4) was used to detect and quantify read-through transcripts. Briefly, ARTDeco preprocesses data using RNA-seq alignment BAM files and transcript regions based on GENCODE GRCh38 (v38) annotation. Read-in genes (aberrantly transcribed due to failed termination of upstream genes) and read-through genes (genes failed to terminate) are then quantified. After performing gene expression deconvolution, Downstream of Gene (DoG) transcripts, within intergenic regions, are then detected. Finally, DoG transcript differential expression is carried out using DESeq2. Differential expression results of DoG are reported as read-through events. Read-through results are reported in Table S2 (attached as a Large Table).

Image analysis. Raw images were obtained and processed using ImageJ, CellSens Standard and Image Lab software.

Statistical analyses. Experimental findings were obtained from three independent experiments unless stated otherwise. Statistics were performed in GraphPad Prism 9. In general, P<0.05 was considered statistically significant. All statistical methods and P-values are provided in the figure legends. Asterisks in graphs denote statistically significant differences as described in figure legends.

TABLE 1

Primers for H1-5(HIST1H1B).

| | Sequence (5'->3') | Template strand | Length | Start | Stop | Tm | GC % | Self comple-mentar-ity | Self 3' comple-mentar-ity |
|---|---|---|---|---|---|---|---|---|---|
| Forward primer (H1-5 Fw' P1) | TGTTGCGGTTTTCACACGC (SEQ ID NO: 1) | Plus | 19 | 31 | 49 | 60.23 | 52.63 | 3 | 2 |
| Reverse primer (H1-5 Rev' P1) | CTAAAGCTGCAAAGGCCAAGAA (SEQ ID NO: 2) | Minus | 22 | 100 | 79 | 59.7 | 45.45 | 4 | 0 |
| Forward primer (H1-5 Fw' P2) | AGACCCCATCTTGAAACTTGC (SEQ ID NO: 3) | Plus | 21 | 78 | 98 | 58.48 | 47.62 | 3 | 3 |
| Reverse primer (H1-5 Rev' P2) | AGCCATTTAGGCACCAGCTA (SEQ ID NO: 4) | Minus | 20 | 183 | 164 | 59.08 | 50 | 4 | 2 |
| Forward primer (H1-5 Fw' P3) | AGAGCTGGGCCACTGGTTA (SEQ ID NO: 5) | Plus | 19 | 14 | 32 | 60.54 | 57.89 | 5 | 2 |
| Reverse primer (H1-5 Rev' P3) | TTCCTAAAAGTCATTCCTAAGCTCT (SEQ ID NO: 6) | Minus | 25 | 102 | 78 | 57.74 | 36 | 4 | 2 |

TABLE 2

Primer Sets for H1-5(HIST1H1B).

| Primer set | Location | Product length |
|---|---|---|
| P1 | CDS and 3'UTR | 70 bp |
| P2 | 500 bp dowstream | 106 bp |
| P3 | 1 kb downstream | 89 bp |

TABLE 3

Primers for H4C5 (HIST1H4E).

| | Sequence (5'->3') | Template strand | Length | Start | Stop | Tm | GC % | Self comple-mentar-ity | Self 3' comple-mentar-ity |
|---|---|---|---|---|---|---|---|---|---|
| Forward primer (H4C5 Fw' P1) | ACAGGGACGCACTCTTTACG (SEQ ID NO: 7) | Plus | 20 | 13 | 32 | 60.04 | 55 | 2 | 2 |
| Reverse primer (H4C5 Rev' P1) | TGGGAAGTCGAGATGCTGAG (SEQ ID NO: 8) | Minus | 20 | 83 | 64 | 59.18 | 55 | 4 | 3 |
| Forward primer (H4C5 Fw' P2) | GCTCACGCAAGGAGAGGTT (SEQ ID NO: 9) | Plus | 19 | 37 | 55 | 60 | 57.89 | 3 | 0 |
| Reverse primer (H4C5 Rev' P2) | ACTTCTAAGGGACAACTGGGT (SEQ ID NO: 10) | Minus | 21 | 108 | 88 | 58.3 | 47.62 | 4 | 1 |

TABLE 3-continued

| Primers for H4C5 (HIST1H4E). | | | | | | | | | |
|---|---|---|---|---|---|---|---|---|---|
| | Sequence (5'->3') | Template strand | Length | Start | Stop | Tm | GC % | Self complementarity | Self 3' complementarity |
| Forward primer (H4C5 Fw' P3) | TCCACAGTTATGCCCCAGATG (SEQ ID NO: 11) | Plus | 21 | 93 | 113 | 59.79 | 52.38 | 3 | 2 |
| Reverse primer (H4C5 Rev' P3) | CACAACGGAAGTTATGGCTGG (SEQ ID NO: 12) | Minus | 21 | 165 | 145 | 59.53 | 52.38 | 4 | 0 |

TABLE 4

| Primer set for H4C5 (HIST1H4E). | | |
|---|---|---|
| Primer set | Location | Product length |
| P1 | CDS and 3'UTR | 71 bp |
| P2 | 500 bp dowstream | 72 bp |
| P3 | 1 kb downstream | 73 bp |

TABLE 5

| Primers for H2AFZ (H2AZ1). | | | | | | | | | |
|---|---|---|---|---|---|---|---|---|---|
| | Sequence (5'->3') | Template strand | Length | Start | Stop | Tm | GC % | Self complementarity | Self 3' complementarity |
| Forward primer (H2AFZ Fw' P1) | ACTGGAATCACCAACACTGGA (SEQ ID NO: 13) | Plus | 21 | 98 | 118 | 59.23 | 47.62 | 3 | 0 |
| Reverse primer (H2AFZ Rev' P1) | ACTGTCTAAAGGATGCCTGGA (SEQ ID NO: 14) | Minus | 21 | 178 | 158 | 58.45 | 47.62 | 4 | 2 |
| Forward primer (H2AFZ Fw' P2) | ATTTCACCTTTTCCGTCCCA (SEQ ID NO: 15) | Plus | 20 | 2 | 21 | 57.33 | 45 | 2 | 0 |
| Reverse primer (H2AFZ Rev' P2) | CCGCGAAGACTAACAAGACAC (SEQ ID NO: 16) | Minus | 21 | 71 | 51 | 59.28 | 52.38 | 4 | 0 |
| Forward primer (H2AFZ Fw' P3) | GAAGGGGACACTCGTTTTCA (SEQ ID NO: 17) | Plus | 20 | 99 | 118 | 57.75 | 50 | 3 | 1 |
| Reverse primer (H2AFZ Rev' P3) | CGCATCCTCCCTCGCTTG (SEQ ID NO: 18) | Minus | 18 | 177 | 160 | 60.59 | 66.67 | 2 | 0 |

TABLE 6

| Primer set for H2AFZ (H2AZ1). | | |
|---|---|---|
| Primer set | Location | Product length |
| P1 | CDS and 3'UTR | 81 bp |
| P2 | 600 bp dowstream | 70 bp |
| P3 | 900 bp-1 kb downstream | 79 bp |

TABLE 7

Primers for H3F3A (H3-3A).

| | Sequence (5'->3') | Template strand | Length | Start | Stop | Tm | GC % | Self complementarity | Self 3' complementarity |
|---|---|---|---|---|---|---|---|---|---|
| Forward primer (H3F3A Fw' P1) | AGAATCCACTATGATGGGAAACA (SEQ ID NO: 19) | Plus | 23 | 9 | 31 | 57.28 | 39.13 | 4 | 0 |
| Reverse primer (H3F3A Rev' P1) | TCCCCTATTTTTCCACTCGC (SEQ ID NO: 20) | Minus | 20 | 160 | 141 | 57.59 | 50 | 2 | 2 |
| Forward primer (H3F3A Fw' P2) | AACTGCCCTAGAAGTGATACGA (SEQ ID NO: 21) | Plus | 22 | 79 | 100 | 58.64 | 45.45 | 4 | 0 |
| Reverse primer (H3F3A Rev' P2) | GCAGTAAGAATGCAAGCCCA (SEQ ID NO: 22) | Minus | 20 | 170 | 151 | 58.82 | 50 | 4 | 0 |
| Forward primer (H3F3A Fw' P3) | ACTATGTGCTCACTGTCCAGGT (SEQ ID NO: 23) | Plus | 22 | 9 | 30 | 61.09 | 50 | 4 | 2 |
| Reverse primer (H3F3A Rev' P3) | GTACATACGTTGAGTGCCAAGT (SEQ ID NO: 24) | Minus | 22 | 110 | 89 | 58.68 | 45.45 | 4 | 2 |

TABLE 8

| Primer set for H3F3A (H3-3A). | | |
|---|---|---|
| Primer set | Location | Product length |
| P1 | CDS and 3'UTR | |
| P2 | 500 bp dowstream | 92 bp |
| P3 | 900 bp-1.1 kb downstream | 102 bp |

Although the present disclosure has been described with respect to one or more particular embodiments and/or examples, it will be understood that other embodiments and/or examples of the present disclosure may be made without departing from the scope of the present disclosure.

The invention claimed is:

1. A method for treating an individual for pancreatic ductal adenocarcinoma (PDAC) consisting of administering to the individual (JTE-607)

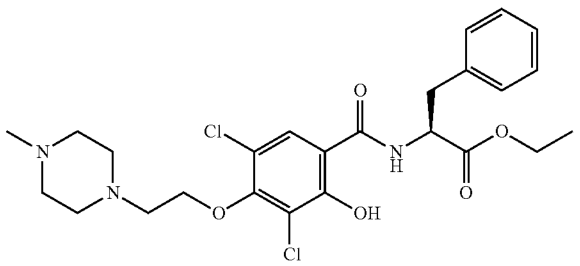

or a pharmaceutically acceptable salt thereof, and afatinib or Osimertinib, and wherein the JTE-607 and the afatinib or Osimertinib synergistically inhibits growth of the PDAC.

2. The method of claim 1, wherein the JTE-607 and the afatinib are administered.

3. The method of claim 1, wherein the JTE-607 and the Osimertinib are administered.

* * * * *

SEQUENCE LISTING

```
Sequence total quantity: 24
SEQ ID NO: 1            moltype = DNA  length = 19
FEATURE                 Location/Qualifiers
source                  1..19
                        mol_type = other DNA
                        organism = synthetic construct
```

-continued

```
SEQUENCE: 1
tgttgcggtt ttcacacgc                                               19

SEQ ID NO: 2           moltype = DNA  length = 22
FEATURE                Location/Qualifiers
source                 1..22
                       mol_type = other DNA
                       organism = synthetic construct
SEQUENCE: 2
ctaaagctgc aaaggccaag aa                                           22

SEQ ID NO: 3           moltype = DNA  length = 21
FEATURE                Location/Qualifiers
source                 1..21
                       mol_type = other DNA
                       organism = synthetic construct
SEQUENCE: 3
agaccccatc ttgaaacttg c                                            21

SEQ ID NO: 4           moltype = DNA  length = 20
FEATURE                Location/Qualifiers
source                 1..20
                       mol_type = other DNA
                       organism = synthetic construct
SEQUENCE: 4
agccatttag gcaccagcta                                              20

SEQ ID NO: 5           moltype = DNA  length = 19
FEATURE                Location/Qualifiers
source                 1..19
                       mol_type = other DNA
                       organism = synthetic construct
SEQUENCE: 5
agagctgggc cactggtta                                               19

SEQ ID NO: 6           moltype = DNA  length = 25
FEATURE                Location/Qualifiers
source                 1..25
                       mol_type = other DNA
                       organism = synthetic construct
SEQUENCE: 6
ttcctaaaag tcattcctaa gctct                                        25

SEQ ID NO: 7           moltype = DNA  length = 20
FEATURE                Location/Qualifiers
source                 1..20
                       mol_type = other DNA
                       organism = synthetic construct
SEQUENCE: 7
acagggacgc actctttacg                                              20

SEQ ID NO: 8           moltype = DNA  length = 20
FEATURE                Location/Qualifiers
source                 1..20
                       mol_type = other DNA
                       organism = synthetic construct
SEQUENCE: 8
tgggaagtcg agatgctgag                                              20

SEQ ID NO: 9           moltype = DNA  length = 19
FEATURE                Location/Qualifiers
source                 1..19
                       mol_type = other DNA
                       organism = synthetic construct
SEQUENCE: 9
gctcacgcaa ggagaggtt                                               19

SEQ ID NO: 10          moltype = DNA  length = 21
FEATURE                Location/Qualifiers
source                 1..21
                       mol_type = other DNA
                       organism = synthetic construct
SEQUENCE: 10
acttctaagg gacaactggg t                                            21

SEQ ID NO: 11          moltype = DNA  length = 21
FEATURE                Location/Qualifiers
source                 1..21
                       mol_type = other DNA
```

-continued

```
                       organism = synthetic construct
SEQUENCE: 11
tccacagtta tgccccagat g                                                21

SEQ ID NO: 12          moltype = DNA  length = 21
FEATURE                Location/Qualifiers
source                 1..21
                       mol_type = other DNA
                       organism = synthetic construct
SEQUENCE: 12
cacaacggaa gttatggctg g                                                21

SEQ ID NO: 13          moltype = DNA  length = 21
FEATURE                Location/Qualifiers
source                 1..21
                       mol_type = other DNA
                       organism = synthetic construct
SEQUENCE: 13
actggaatca ccaacactgg a                                                21

SEQ ID NO: 14          moltype = DNA  length = 21
FEATURE                Location/Qualifiers
source                 1..21
                       mol_type = other DNA
                       organism = synthetic construct
SEQUENCE: 14
actgtctaaa ggatgcctgg a                                                21

SEQ ID NO: 15          moltype = DNA  length = 20
FEATURE                Location/Qualifiers
source                 1..20
                       mol_type = other DNA
                       organism = synthetic construct
SEQUENCE: 15
atttcacctt ttccgtccca                                                  20

SEQ ID NO: 16          moltype = DNA  length = 21
FEATURE                Location/Qualifiers
source                 1..21
                       mol_type = other DNA
                       organism = synthetic construct
SEQUENCE: 16
ccgcgaagac taacaagaca c                                                21

SEQ ID NO: 17          moltype = DNA  length = 20
FEATURE                Location/Qualifiers
source                 1..20
                       mol_type = other DNA
                       organism = synthetic construct
SEQUENCE: 17
gaaggggaca ctcgttttca                                                  20

SEQ ID NO: 18          moltype = DNA  length = 18
FEATURE                Location/Qualifiers
source                 1..18
                       mol_type = other DNA
                       organism = synthetic construct
SEQUENCE: 18
cgcatcctcc ctcgcttg                                                    18

SEQ ID NO: 19          moltype = DNA  length = 23
FEATURE                Location/Qualifiers
source                 1..23
                       mol_type = other DNA
                       organism = synthetic construct
SEQUENCE: 19
agaatccact atgatgggaa aca                                              23

SEQ ID NO: 20          moltype = DNA  length = 20
FEATURE                Location/Qualifiers
source                 1..20
                       mol_type = other DNA
                       organism = synthetic construct
SEQUENCE: 20
tcccctattt ttccactcgc                                                  20

SEQ ID NO: 21          moltype = DNA  length = 22
FEATURE                Location/Qualifiers
source                 1..22
```

-continued

```
                       mol_type = other DNA
                       organism = synthetic construct
SEQUENCE: 21
aactgcccta gaagtgatac ga                                            22

SEQ ID NO: 22          moltype = DNA  length = 20
FEATURE                Location/Qualifiers
source                 1..20
                       mol_type = other DNA
                       organism = synthetic construct
SEQUENCE: 22
gcagtaagaa tgcaagccca                                               20

SEQ ID NO: 23          moltype = DNA  length = 22
FEATURE                Location/Qualifiers
source                 1..22
                       mol_type = other DNA
                       organism = synthetic construct
SEQUENCE: 23
actatgtgct cactgtccag gt                                            22

SEQ ID NO: 24          moltype = DNA  length = 22
FEATURE                Location/Qualifiers
source                 1..22
                       mol_type = other DNA
                       organism = synthetic construct
SEQUENCE: 24
gtacatacgt tgagtgccaa gt                                            22
```